US010385084B2

(12) United States Patent
Morris et al.

(10) Patent No.: US 10,385,084 B2
(45) Date of Patent: Aug. 20, 2019

(54) IRON(II) CATALYSTS CONTAINING TRIDENTATE PNP LIGANDS, THEIR SYNTHESIS, AND USE THEREOF

(71) Applicant: The Governing Council of the University of Toronto, Toronto (CA)

(72) Inventors: Robert H. Morris, Toronto (CA); Paraskevi Olympia Lagaditis, Richmond (CA); Jessica Sonnenberg, Burlington (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 15/110,312

(22) PCT Filed: Jan. 8, 2015

(86) PCT No.: PCT/CA2015/050008
§ 371 (c)(1),
(2) Date: Jul. 7, 2016

(87) PCT Pub. No.: WO2015/103703
PCT Pub. Date: Jul. 16, 2015

(65) Prior Publication Data
US 2016/0326202 A1  Nov. 10, 2016

Related U.S. Application Data

(60) Provisional application No. 61/925,021, filed on Jan. 8, 2014.

(51) Int. Cl.
*C07F 9/46* (2006.01)
*C07F 15/02* (2006.01)
*B01J 31/18* (2006.01)
*B01J 31/24* (2006.01)
*C07C 29/141* (2006.01)
*C07C 29/145* (2006.01)
*C07D 213/30* (2006.01)
*C07D 307/42* (2006.01)
*C07D 333/16* (2006.01)

(52) U.S. Cl.
CPC ............ *C07F 15/02* (2013.01); *B01J 31/189* (2013.01); *B01J 31/2409* (2013.01); *C07C 29/141* (2013.01); *C07C 29/145* (2013.01); *C07D 213/30* (2013.01); *C07D 307/42* (2013.01); *C07D 333/16* (2013.01); *C07F 9/46* (2013.01); *B01J 2231/643* (2013.01); *B01J 2531/0258* (2013.01); *B01J 2531/842* (2013.01); *C07C 2601/14* (2017.05)

(58) Field of Classification Search
None
See application file for complete search history.

(56) References Cited

U.S. PATENT DOCUMENTS

2010/0145087 A1  6/2010  Mikhailine et al.

FOREIGN PATENT DOCUMENTS

WO   2013173930 A1   11/2013
WO   2015091158 A1    6/2015

OTHER PUBLICATIONS

Langer et al., Angew. Chem. Int. Ed., 2011, 50(9):2120-2124. (Year: 2011).*
International Search Report issued in corresponding application No. PCT/CA2015/050008 dated May 1, 2015 (2 pages).
Written Opinion of the International Searching Authority issued in corresponding application No. PCT/CA2015/050008 dated May 1, 2015 (5 pages).
Langer et al, "Efficient Hydrogenation of Ketones Catalyzed by an Iron Pincer Complex"; Angewandte Chemie International Edition, vol. 50, issue 9, pp. 2120-2124; Jan. 5, 2011 (5 pages).
J.R. Ares et al., "Thermal and mechanically activated decomposition of LiAlH4"; Materials Research Bulletin, vol. 43; No. 5, pp. 1263-1275; May 24, 2007 (13 pages).
Bing Luo et al., "Hydrido and chloro gallium and aluminium complexes with the tridentate bis(2-dimethylaminoethyl) amide ligand"; Dalton Transactions; vol. 37, pp. 4491-4498; Jul. 24, 2006 (8 pages).
Sean E. Clapham et al., "Probing the Effect of the Ligand X on the Properties and Catalytic Activity of the Complexes RuHX(diamine)(PPh3)2 (X=OPh, 4-SC6H4OCH3, OPPh2, Op(OEt)2, CCPh, NCCHCN, CH(COOMe)2; diamine ) 2,3-Diamino-2,3-dimethylbutane, (R,R)-1,2-Diaminocyclohexane)"; Organometallics, vol. 25; No. 22, pp. 5477-5486; Jul. 21, 2006 (10 pages).
Walter Baratta et al., "Role of the NH2 Functionality and Solvent in Terdentate CNN Alkoxide Ruthenium Complexes for the Fast Transfer Hydrogenation of Ketones in 2-Propanol"; Chem. Eur. J., vol. 14; No. 18, pp. 5588-5595; Apr. 2, 2008 (8 pages).
Jing Zhang et al., "Electron-Rich, Bulky Ruthenium PNP-Type Complexes. Acceptorless Catalytic Alcohol Dehydrogenation"; Organometallics, vol. 23; No. 17, pp. 4026-4033; Apr. 19, 2004 (8 pages).
Susan M. Kloek et al., "Stereoselective Decarbonylation of Methanol to Form a Stable Iridium(III) trans-Dihydride Complex"; Organometallics, vol. 25; No. 12, pp. 3007-3011; Dec. 28, 2005 (5 pages).
Michael W. Schmidt et al., "General Atomic and Molecular Electronic Structure System"; Journal of Computational Chemistry, vol. 14, No. 11; pp. 1347-1363; May 28, 1993 (17 pages).
P. Jeffrey Hay et al., "Ab initio effective core potentials for molecular calculations. Potentials for the transition metal atoms Sc to Hg"; Journal of Chemical Physics, vol. 82, No. 1; pp. 270-283; Jan. 1, 1985 (13 pages).
Willard R. Wadt et al., "Ab initio effective core potentials for molecular calculations. Potentials for main group elements Na to Bi"; Journal of Chemical Physics, vol. 82, No. 1; pp. 284-298; Jan. 1, 1985 (13 pages).
P. Jeffrey Hay et al., "Ab initio effective core potentials for molecular calculations. Potentials for K to Au including the outermost core orbitals"; Journal of Chemical Physics, vol. 82, No. 1; pp. 299-310; Jan. 1, 1985 (13 pages).

(Continued)

*Primary Examiner* — Clinton A Brooks
*Assistant Examiner* — Kofi Adzamli
(74) *Attorney, Agent, or Firm* — Ferguson Braswell Fraser Kubasta PC

(57) ABSTRACT

The application describes catalytic materials for hydrogenation or asymmetric hydrogenation. In particular, the application describes iron(II) complexes containing tridentate diphosphine PNP ligands useful for catalytic hydrogenation.

20 Claims, 28 Drawing Sheets

(56) References Cited

OTHER PUBLICATIONS

Roberto Peverati et al., "M11-L: A Local Density Functional That Provides Improved Accuracy for Electronic Structure Calculations in Chemistry and Physics"; Journal of Physical Chemistry Letters, vol. 3, No. 1; pp. 117-124; Dec. 12, 2011 (8 pages).
Anant D. Kulkarni et al., "Performance of Density Functional Theory and Møller-Plesset Second-Order Perturbation Theory for Structural Parameters in Complexes of Ru"; Journal of Chemical Theory and Computation, vol. 7, No. 7; pp. 2325-2332; May 27, 2011 (8 pages).
Yan Zhao et al., "A new local density functional for main-group thermochemistry, transition metal bonding, thermochemical kinetics, and noncovalent interactions"; The Journal of Chemical Physics, vol. 125, No. 19; pp. 194101.1-194101.18; Nov. 15, 2006 (19 pages).
Timothy Clark et al., "Efficient Diffuse Function-Augmented Basis Sets for Anion Calculations. III.* The 3-21 +G Basis Set for First-Row Elements, Li-F"; Journal of Computational Chemistry, vol. 4, No. 3; pp. 294-301; Nov. 22, 1982 (8 pages).
Benjamin J. Lynch et al., "Effectiveness of Diffuse Basis Functions for Calculating Relative Energies by Density Functional Theory"; J. Phys. Chem. A, vol. 107, No. 9; pp. 1384-1388; Sep. 9, 2002 (5 pages).
Michael J. Frisch et al., "Self-consistent molecular orbital methods 25. Supplementary functions for Gaussian basis sets"; The Journal of Chemical Physics, vol. 80, No. 7; pp. 3265-3269; Apr. 1, 1984 (6 pages).
Jacopo Tomasi et al., "Quantum Mechanical Continuum Solvation Models"; Chemical Reviews, vol. 105, No. 8; pp. 2999-3093; Jan. 6, 2005 (96 pages).
J. Tomasi et al., "The IEF version of the PCM solvation method: an overview of a new method addressed to study molecular solutes at the QM ab initio level"; Journal of Molecular Structure (Theochem), vol. 464, Nos. 1-3; pp. 211-226; May 1999 (16 pages).
Kenichi Fukui et al., "The Path of Chemical Reactions—The IRC Approach"; Accounts of Chemical Research, vol. 14, No. 12; pp. 363-368; Dec. 1981 (6 pages).
Maria T. Bautista et al., "Stereochemical Control of the Exchange of Hydrogen Atoms between Hydride and Dihydrogen Ligands in the Complexes [M('n2-H2)(H)(meso- or rac-tetraphos-1)]+, M = Fe, Os"; Journal of the American Chemical Society, vol. 110, No. 12; pp. 4056-4057; Dec. 23, 1987 (2 pages).
Maria Teresa Bautista et al., "New dihydrogen complexes: the synthesis and spectroscopic properties of iron(II), ruthenium(II), and osmium(II) complexes containing the meso-tetraphos-1 ligand"; Can. J. Chem., vol. 72, No. 3; pp. 547-560; Jul. 19, 1993 (14 pages).
Paraskevi O. Lagaditis et al., "Iron(II) Complexes Containing Unsymmetrical P-N-P' Pincer Ligands for the Catalytic Asymmetric Hydrogenation of Ketones and Imines"; Journal of the American Chemical Society, vol. 136, No. 4; pp. 1367-1380; Jan. 21, 2014 (14 pages).
Ryan J. Trovitch et al., "Bis(diisopropylphosphino)pyridine Iron Dicarbonyl, Dihydride, and Silyl Hydride Complexes"; Inorganic Chemistry, vol. 45, No. 18; pp. 7252-7260; May 18, 2006 (9 pages).
Dmitry G. Gusev et al., "Synthesis, Structural Diversity, Dynamics, and Acidity of the M(II) and M(IV) Complexes [MH3 (PR3)4]+ (M ) Fe, Ru, Os; R = Me, Et)"; Journal of the American Chemical Society, vol. 119, No. 16; pp. 3716-3731; Oct. 23, 1996 (16 pages).
Danièle Schott et al., "The reaction of M(CO)3(Ph2PCH2CH2PPh2) (M = Fe, Ru) with parahydrogen: probing the electronic structure of reaction intermediates and the internal rearrangement mechanism for the dihydride products"; Dalton Transactions; vol. 20, No. 20; pp. 3218-3224; Aug. 25, 2004 (7 pages).
Elizabeth A. Bielinksi et al., "Lewis Acid-Assisted Formic Acid Dehydrogenation Using a Pincer-Supported Iron Catalyst"; Journal of the American Chemical Society, vol. 136, No. 29; pp. 10234-10237; Jul. 7, 2014 (4 pages).

D. H. Gerlach et al., "Stereochemically Nonrigid Six-Coordinate Molecules.1 III. Preparations and Reactions of Tetrakis (organophosphorus) Metal Dihydride Complexes"; Journal of the American Chemical Society, vol. 94, No. 13; pp. 4545-4549; Nov. 24, 1971 (5 pages).
P. Meakin et al., "Stereochemically Nonrigid Six-Coordinate Molecules. 1 III. The Temperature-Dependent 1H and 31P Nuclear Magnetic Resonance Spectra of Some Iron and Ruthenium Dihydrides"; Journal of the American Chemical Society, vol. 95, No. 1; pp. 75-88; Jun. 20, 1972 (14 pages).
Rudolf Hartmann et al., "Noyori's Hydrogenation Catalyst Needs a Lewis Acid Cocatalyst for High Activity"; Angew. Chem. Ind. Ed., vol. 40, No. 19; pp. 3581-3585; May 17, 2001 (5 pages).
Jeremy M. John et al., "Base-Catalyzed Bifunctional Addition to Amides and Imides at Low Temperature. A New Pathway for Carbonyl Hydrogenation"; Journal of the American Chemical Society, vol. 135, No. 23; pp. 8578-8584; May 20, 2013 (7 pages).
Pavel A. Dub et al., "Unravelling the Mechanism of the Asymmetric Hydrogenation of Acetophenone by [RuX2 (diphosphine)(1,2-diamine)] Catalysts"; Journal of the American Chemical Society, vol. 136, No. 9; pp. 3505-3521; Feb. 13, 2014 (17 pages).
Elisabetta Alberico et al., "Selective Hydrogen Production from Methanol with a Defined Iron Pincer Catalyst under Mild Conditions"; Angew. Chem., vol. 125; Dec. 2013; pp. 14412-14416 (5 pages).
Sumit Chakraborty et al., "Iron-Based Catalysts for the Hydrogenation of Esters to Alcohols"; Journal of the American Chemical Society, vol. 136, No. 22; pp. 7869-7872; May 20, 2014 (4 pages).
Kamaluddin Abdur-Rashid et al., "Mechanism of the Hydrogenation of Ketones Catalyzed by trans-Dihydrido(diamine) ruthenium(II) Complexes"; Journal of the American Chemical Society, vol. 124, No. 50; pp. 15104-15118; Aug. 10, 2001 (15 pages).
Kamaluddin Abdur-Rashid et al., "Ruthenium Dihydride RuH2(PPh3)2((R,R)-cyclohexyldiamine) and Ruthenium Monohydride RuHCl(PPh3)2((R,R)-cyclohexyldiamine): Active Catalyst and Catalyst Precursor for the Hydrogenation of Ketones and Imines"; Organometallics, vol. 19, No. 14; pp. 2655-2657; Mar. 16, 2000 (3 pages).
Alen Hadzovic et al., "A Mechanism Displaying Autocatalysis: The Hydrogenation of Acetophenone Catalyzed by RuH (S-binap)(app) Where app is the Amido Ligand Derived from 2-Amino-2-(2-pyridyl)propane"; Organometallics, vol. 26, vol. 24; pp. 5987-5999; Aug. 23, 2007 (13 pages).
Ryoji Noyori, "Asymmetric Catalysis: Science and Opportunities (Nobel Lecture)"; Angew. Chem. Ind. Ed., vol. 41, No. 12; pp. 2008-2022; Jun. 12, 2002 (15 pages).
Marcello Bertoli et al., "Osmium and Ruthenium Catalysts for Dehydrogenation of Alcohols"; Organometallics, vol. 30, No. 13; pp. 3479-3482; Published Jun. 6, 2011 (4 pages).
Robert Abbel et al., "A Succession of Isomers of Ruthenium Dihydride Complexes. Which One is the Ketone Hydrogenation Catalyst?"; Journal of the American Chemical Society, vol. 127, No. 6; pp. 1870-1882; Published Jan. 21, 2005 (13 pages).
Robert J. Hamilton et al., "Direct Observations of the Metal-Ligand Bifunctional Addition Step in an Enantioselective Ketone Hydrogenation"; Journal of the American Chemical Society, vol. 130, No. 36; pp. 11979-11987; Published Aug. 15, 2008 (9 pages).
Satoshi Takebayashi et al., "Facile Bifunctional Addition of Lactones and Esters at Low Temperatures. The First Intermediates in Lactone/Ester Hydrogenations"; American Chemical Society Communications, vol. 28, No. 8; pp. 2349-2351; Apr. 27, 2009 (3 pages).
Shaolin Zhou et al., "Enantioselective Synthesis of Amines: General, Efficient Iron-Catalyzed Asymmetric Transfer Hydrogenation of Imines"; Angew. Chem. Int. Ed., vol. 49; pp. 8121-8125; Published 2010 (5 pages).
Alexandre Mikhailine et al., "Efficient Asymmetric Transfer Hydrogenation of Ketones Catalyzed by an Iron Complex Containing a P-N-N-P. Tetradentate Ligand Formed by Template Synthesis"; J. Am. Chem. Soc., vol. 131; pp. 1394-1395; Published Jan. 9, 2009 (2 pages).

(56) References Cited

OTHER PUBLICATIONS

Alexandre A. Mikhailine et al., "Effect of the Structure of the Diamine Backbone of P-N-N-P. ligands in Iron(II) Complexes on Catalytic Activity in the Transfer Hydrogenation of Acetophenone"; Inorganic Chemistry, vol. 49; pp. 11039-11044; Published Nov. 10, 2010 (6 pages).
Paraskevi O. Lagaditis et al., "Iron Complexes for the Catalytic Transfer Hydrogenation of Acetophenone: Steric and Electronic Effects Imposed by Alkyl Substituents at Phosphorus"; Inorganic Chemistry, vol. 49; pp. 10057-10066; Published Oct. 6, 2010 (10 pages).
Peter E. Sues et al., "Stereoelectronic Factors in Iron Catalysis: Synthesis and Characterization of Aryl-Substituted Iron(II) Carbonyl P-N-N-P Complexes and Their Use in the Asymmetric Transfer Hydrogenation of Ketones"; Organometallics, vol. 30; pp. 4418-4431; Published Jul. 20, 2011 (14 pages).
Paraskevi O. Lagaditis et al., "Low-Valent Ene-Amido Iron Complexes for the Asymmetric Transfer Hydrogenation of Acetophenone without Base"; Journal of the American Chemical Society, vol. 133; pp. 9662-9665; Published May 31, 2011 (4 pages).
Alexandre A. Mikhailine et al., "The Mechanism of Efficient Asymmetric Transfer Hydrogenation of Acetophenone Using an Iron(II) Complex Containing an (S,S)-Ph2PCH2CH=NCHPhCHPhN=CHCH2PPh2 Ligand: Partial Ligand Reduction is the Key"; Journal of the American Chemical Society, vol. 134; pp. 12266-12280; Published Jul. 13, 2012 (15 pages).
Demyan E. Prokopchuk et al., "Inner-Sphere Activation, Outer-Sphere Catalysis: Theoretical Study on the Mechanism of Transfer Hydrogenation of Ketones Using Iron(II) PNNP Eneamido Complexes"; Organometallics, vol. 31; pp. 7375-7385; Published Oct. 9, 2012 (11 pages).
Alexandre A. Mikhailine et al., "Asymmetric Transfer Hydrogenation of Ketimines Using Well-Defined Iron(II)-Based Precatalysts Containing a PNNP Ligand"; Organic Letters, vol. 14, No. 17; pp. 4638-4641; Published Aug. 27, 2012 (4 pages).
Benito-Garagorri, D. et al., "Striking Differences between the Solution and Solid-State Reactivity of Iron PNP Pincer Complexes with Carbon Monoxide", Organometallics, vol. 28, Issue 24, Dec. 4, 2009, pp. 6902-6914 (13 pages).
Benito-Garagorri, D. et al., "Stereospecific and Reversible CO Binding at Iron Pincer Complexes"; Angewandte, Intl. Edition, vol. 47, Issue 47, Nov. 10, 2008, pp. 9142-9145 (4 pages).
Benito-Garagorri, D. et al., "Kinetically Controlled Formation of Octahedral trans-Dicarbonyl Iron(II) PNP Pincer Complexes: The Decisive Role of Spin-State Changes"; Organometallics, vol. 29, Issue 21, Apr. 29, 2010, pp. 1932-4942 (11 pages).
Langer, R. et al., "Iron Borohydride Pincer Complexes for the Efficient Hydrogenation of Ketones under Mild, Base-Free Conditions: Synthesis and Mechanistic Insight"; Chemistry (A European Journal), vol. 18, Issue 23, Jun. 4, 2012; pp. 7196-7209 (14 pages).
Yang, Xinzheng, "Unexpected Direct Reduction Mechanism for Hydrogenation of Ketones Catalyzed by Iron PNP PincerComplexes"; Inorganic Chemistry, vol. 50, Issue 24; Dec. 19, 2011; pp. 12836-12843 (8 pages).
Gunanathan, C. et al., "Direct Synthesis of Amides from Alcohols and Amines with Liberation of H2"; Science, vol. 317, Issue 5839; Aug. 10, 2007, pp. 790-792 (3 pages).
Gunanathan, C. et al., "Metal Ligand Cooperation by Aromatization-Dearomatization: A New Paradigm in Bond Activation and "Green" Catalysis"; Accounts of Chemical Research, vol. 44, No. 8, Aug. 16, 2011; pp. 588-602 (15 pages).
Casey, C.P. et al., "An Efficient and Chemoselective Iron Catalyst for the Hydrogenation of Ketones"; Journal of American Chemical Society (JACS), vol. 129, Issue 18, Apr. 17, 2007, pp. 5816-5817 (2 pages).
Casey, C.P. et al., "Cyclopentadienone Iron Alcohol Complexes: Synthesis, Reactivity, and Implications for the Mechanism of Iron-Catalyzed Hydrogenation of Aldehydes"; Journal of American Chemical Society (JACS); vol. 131, No. 7, Feb. 4, 2009, pp. 2499-2507 (9 pages).
Berkessel, A. et al., "Light-Induced Enantioselective Hydrogenation Using Chiral Derivatives of Casey's Iron Cyclopentadienone Catalyst"; Organometallics, vol. 30 No. 14, Jun. 30, 2011, pp. 3880-3887 (8 pages).
Zhou, S. et al., "Cooperative Transition-Metal and Chiral Brønsled Acid Catalysis: Enantioselective Hydrogenation of Imines to Form Amines"; Angewandte, Intl. Ed., vol. 50, No. 22, May 23, 2011, pp. 5120-5124 (5 pages).
Fleischer, S. et al., "Consecutive Intermolecular Reductive Hydroamination: Cooperative Transition-Metal and Chiral Brønsted Acid Catalysis"; Chemistry (A European Journal); vol. 18, No. 29, Jul. 16, 2012, pp. 9005-9010 (6 pages).
Lagaditis, P.O. et al., "Template Synthesis of Iron(II) Complexes Containing Tridentate P-N-S, P-N-P, P-N-N, and Tetradentate P-N-N-P. Ligands"; Inorganic Chemistry, vol. 49, No. 3, Dec. 22, 2009, pp. 1094-1102 (9 pages).
Mikhailine, A.A. et al., "New cyclic phosphonium salts derived from the reaction of phosphine-aldehydes with acid", Organometallic Chemistry, vol. 695, No. 14, Jun. 15, 2010, pp. 1824-1830 (7 pages).
Turrell, P.J. et al., "The Third Hydrogenase: A Ferracyclic Carbamoyl with Close Structural Analogy to the Active Site of Hmd"; Angewandte, Intl. Ed., vol. 122, No. 41, Oct. 4, 2010, pp. 7670-7673 (4 pages).
Marco, A. et al., "Assessment of Additives for Nitrogen, Carbon, Hydrogen and Sulfur Determination by Organic Elemental Analysis"; Microchimita Acta, vol. 142, Nos. 1-2, Jun. 2003, pp. 13-19 (7 pages).
Liang, L-C et al., "A terminal nickel(II) anilide complex featuring an unsymmetrically substituted amido pincer ligand: synthesis and reactivity"; Dalton Transactions, vol. 40, No. 35, Jun. 13, 2011, pp. 9004-9011 (8 pages).
Lansing Jr., R.B. et al., "Unsymmetrical RPNPR¢ pincer ligands and their group 10 complexes"; Dalton Transactions, vol. 40, No. 35, May 20, 2011, pp. 8950-8958 (9 pages).
Benito-Garagorri, D. et al., "Iron(II) Complexes Bearing Tridentate PNP Pincer-Type Ligands as Catalysts for the Selective Formation of 3-ydroxyacrylates from Aromatic Aldehydes and Ethyldiazoacetate"; Organometallics, vol. 26, No. 1, Jan. 1, 2007, pp. 217-222 (6 pages).
Zuo, W. et al., "Amine(imine)diphosphine Iron Catalysts for Asymmetric Transfer Hydrogenation of Ketones and Imines"; Science, vol. 342, No. 6162, Nov. 29, 2013, pp. 1080-1083 (4 pages).
Antberg, M. et al., "Oligophosphan-Liganden : XXV. cis-FeH2[P(CH2CH2CH2PMe2)3]: Synthese und Reaktionen"; Organometallic Chemistry, vol. 338, No. 3, Jan. 19, 1988, pp. 319-327 (9 pages).
Antberg, M. et al., "Oligophosphan-Liganden, XII [1] Pseudohalogeno- und Halogenohydridoeisen(II)-Komplexe des tripodal-tetratertiären Phosphanliganden P(CH2CH2CH2PMe2)3"; Z. Naturforsch, Chem. Science, vol. 40b, Jun. 19, 1985, pp. 1485-1489 (5 pages).
Roger, C. et al., "A direct and specific sonochemically assisted preparation of Fe( C,Me,) (dppe)X (X = Cl, H)"; Organometallic Chemistry, vol. 336, No. 1-2, Dec. 8, 1987, pp. C13-C16 (4 pages).
Field, L.D. et al., "Iron Complexes Containing the Tripodal Tetraphosphine Ligand PCH2CH2PMe2)3"; Inorganic Chemistry, vol. 36, No. 13, Jun. 1, 1997, pp. 2884-2892 (9 pages).
Liu, T. et al., "Synthesis, Characterization, and Reactivity of Fe Complexes Containing Cyclic Diazadiphosphine Ligands: The Role of the Pendant Base in Heterolytic Cleavage of H2"; Journal of the American Chemical Society (JACS), vol. 134, No. 14, Apr. 11, 2012, pp. 6257-6272 (16 pages).
Gao, Y. et al., "Reactions of Fe III with LiAlH4 and LiBH4 in the presence of bis(diphenylphosphino)methane (dppm) and CO"; Polyhedron, vol. 16, No. 16, Dec. 1997, pp. 2797-2807 (11 pages).
Ohki, Y. et al., "[{(n5-05Me5)Fe}2(μ-H)4]: A Novel Dinuclear Iron Tetrahydrido Complex"; Angewandte, Intl. Ed., vol. 39, No. 17, Sep. 1, 2000, pp. 3120-3122 (3 pages).
Argouarch, G. et al., "[(n5-05Me5)Fe(Ph2PCH2CH2CH2PPh2)][SO3CF3], a Stable 16-Electron Complex with a Coordinating Counteranion and without Agostic Interaction: The Dramatic Role of a Trivial Methylene Group"; Organometallics, vol. 21, No. 7, Apr. 2002, pp. 1341-1448 (8 pages).

(56) References Cited

OTHER PUBLICATIONS

Jia, G. et al., "Use of the New Ligand P(CH2CH2PCy2)3 in the Synthesis of Dihydrogen Complexes of Iron(I1) and Ruthenium(I1)"; Organometallics, vol. 12, No. 3, Mar. 1, 1993, pop. 906-916 (11 pages).
Fiedleer, A. et al., ""Bare" Iron Methoxide Cation: A Simple Model To Probe the Mechanism of β-Hydrogen Transfer n Organometallic Compounds"; Journal of American Chemical Society (JACS). vol. 118, No. 21, Jan. 1, 1996, pp. 5047-5055 (9 pages).
Noyori, R. et al., "Asymmetric Catalysis by Architectural and Functional Molecular Engineering: Practical Chemo-and Stereoselective Hydrogenation of Ketones"; Angewandte, Intl. Ed., vol. 40, No. 1, Jan. 5, 2001, pp. 40-73 (33 pages).
Abdur-Rashid, K. et al., "Catalytic Cycle for the Asymmetric Hydrogenation of Prochiral Ketones to Chiral Alcohols: Direct Hydride and Proton Transfer from Chiral Catalysts trans-Ru(H)2(diphosphine)(diamine) to Ketones and Direct Addition of Dihydrogen to the Resulting Hydridoamido Complexes"; Journal of American Chemical Society (JACS); vol. 123, No. 30, Aug. 1, 2001, pp. 7473-7474 (2 pages).
Clapham, S.E. et al., "Mechanisms of the H2-hydrogenation and transfer hydrogenation of polar bonds catalyzed by ruthenium hydride complexes"; Coordination Chemistry Reviews, vol. 248, No. 21-24, Dec. 2004, pop. 2201-2237 (37 pages).
Brookhart, M. et al., "The Reaction of Benzylideneacetoneiron Tricarbonyl With DIE-NE& Measurement of Relative Reactivities Using Competition Experiments"; Journal of Organometallic Chemistry, vol. 164, No. 2, Jan. 9, 1979, pp. 193-202 (10 pages).
Benjamin E. Moulton et al., "A Rationale for the Linear Correlation of Aryl Substituent Effects in Iron(0) Tricarbonyl Complexes Containing a,b-Unsaturated Enone (Chalcone) Ligands"; Organometallics, vol. 26, No. 25; pp. 6354-6365; Jun. 26, 2007 (12 pages).
Hans-Joachim Knolker, "Efficient Synthesis of Tricarbonyliron-Diene Complexes—Development of an Asymmetric Catalytic Complexation"; Chemical Reviews, vol. 100; pp. 2941-2961; Mar. 10, 2000 (22 pages).
Sarah K. Russell et al., "Synthesis, Electronic Structure, and Catalytic Activity of Reduced Bis(aldimino)pyridine Iron Compounds: Experimental Evidence for Ligand Participation"; Inorganic Chemistry, vol. 50; pp. 3159-3169; Mar. 11, 2011 (11 pages).
Yan Zhao et al., "The M06 suite of density functionals for main group thermochemistry, thermochemical kinetics, noncovalent interactions, excited states, and transition elements: two new functionals and systematic testing of four M06-class functionals and 12 other functionals"; Theor. Chem. Account, vol. 120; pp. 215-241; Jul. 12, 2007 (27 pages).
Yan Zhao et al., "Density Functionals with Broad Applicability in Chemistry"; Accounts of Chemical Research, vol. 41, No. 2; pp. 157-167; Feb. 2008 (11 pages).
Aleksandr V. Marenich et al., "Universal Solvation Model Based on Solute Electron Density and on a Continuum Model of the Solvent Defined by the Bulk Dielectric Constant and Atomic Surface Tensions"; J. Phys. Chem. B., vol. 113; pp. 3378-6396; Jan. 25, 2009 (19 pages).
Tondreau, A.M. et al., "Enantiopure Pyridine Bis(oxazoline) "Pybox" and Bis(oxazoline) "Box" Iron Dialkyl Complexes: Comparison to Bis(imino)pyridine Compounds and Application to Catalytic Hydrosilylation of Ketones", Published Jun. 9, 2009; Organometalics, pp. 3928-3940 (13 pages).
Monfette, S. et al., "Enantiopure C1-Symmetric Bis(imino)pyridine Cobalt Complexes for Asymmetric Alkene -Hydrogenation"; Published Mar. 6, 2012, Journal of the American Chemical Society (JACS), pp. 4561-4564, (4 pages).
Sylvester, K.T. et al., "Iron-Catalyzed, Hydrogen-Mediated Reductive Cyclization of 1,6-Enynes and Diynes: Evidence for Bis(imino)pyridine Ligand Participation", Journal of the American Chemical Society (JACS) Published Jun. 5, 2009, pp. 8772-8774 (3 pages).

Wu, J.Y. et al., "A Strategy for the Synthesis of Well-Defined Iron Catalysts and Application to Regioselective Diene Hydrosilylation", Journal of the American Chemical Society (JACS) Published Sep. 1, 2010, pp. 13214-13216 (3 pages).
Dong, Z.R. et al., "Asymmetric transfer hydrogenation of ketones catalyzed by nickel complex with new PNO-type ligands", Chinese Chemical Letters, vol. 23, Issue 5, May 2012, pp. 533-536 (4 pages).
Vasudevan, K.V. et al., "Alkene Hydrogenation Catalyzed by Nickel Hydride Complexes of an Aliphatic PNP Pincer Li"; European Journal of Inorganic Chemistry (EurJIC), Published Aug. 31, 2012, pp. 4898-4906 (9 pages).
Zhang, G. et al., "Mild and Homogeneous Cobalt-Catalyzed Hydrogenation of C=C, C=O, and C=N. Bonds"; Published in Angewandte, A Journal of the German Chemical Society, vol. 51, Issue 48, Nov. 26, 2012, pp. 12102-12106 (5 pages).
Harman, W. H. et al., "Reversible H2 Addition across a Nickel-Borane Unit as a Promising Strategy for Catalysis"; Journal of the American Chemical Society (JACS) Published Mar. 1, 2012, pp. 5080-5082 (3 pages).
Federsel, C. et al., "Catalytic Hydrogenation of Carbon Dioxide and Bicarbonates with a Well-Defined Cobalt Dihydrogen Complex", Chemistry (A European Journal) vol. 18, Issue 1, Jan. 2, 2012 pp. 72-75 (4 pages).
Werkmeister, S. et al., "Towards a Zinc-Catalyzed Asymmetric Hydrogenation/Transfer Hydrogenation of Imines"; Chemistry (An Asian Journal), vol. 7, Issue 11, Nov. 2012, pp. 2562-2568 (7 pages).
Huisman, G.W. et al., "Practical chiral alcohol manufacture using ketoreductases"; Current Opinion in Chemical Biology, vol. 14, Issue 2, Apr. 2010, pp. 122-129 (8 pages).
Savile, C.K. et al., "Biocatalytic Asymmetric Synthesis of Chiral Amines from Ketones Applied to Sitagliptin Manufacture"; Published in Science, vol. 329, Issue 5989, Jul. 16, 2010, pp. 305-309 (5 pages).
Ringenberg, M.R. et al., "Merging the best of two worlds: artificial metalloenzymes for enantioselective catalysis", Published in Journal of Chemical Communications (ChemComm), vol. 47, Issue 30, May 20, 2011, pp. 8470-8476 (7 pages).
Matsuda, T. et al., "Recent progress in biocatalysis for asymmetric oxidation and reduction"; Published in Tetrahedron Asymmetry, vol. 20, Issue 5, Mar. 25, 2009, pp. 513-557 (45 pages).
Stephan, D.W. et al., "Metal-Free Catalytic Hydrogenation of Polar Substrates by Frustrated Lewis Pairs", Published in Inorganic Chemistry, vol. 50. Issue 24, May 2, 2011, pp. 12338-12348 (11 pages).
Rueping, M. et al., "Advances in catalytic metal-free reductions: from bio-inspired concepts to applications in the organocatalytic synthesis of pharmaceuticals and natural products"; Published in Green Chemistry, Issue 5, Mar. 31, 2011, pp. 1084-1105 (22 pages).
Sumerin, V. et al., "Highly Active Metal-Free Catalysts for Hydrogenation of Unsaturated Nitrogen-Containing Compounds"; Published in Advanced Synthesis and Catalysis, vol. 353, Issue 11-12, Aug. 10, 2011, pp. 2093-2110 (18 pages).
Farrell, J.M. et al., "Activation of Hydrogen and Hydrogenation Catalysis by a Borenium Cation"; Published in Journal of the American Chemical Society (JACS), vol. 134, Issue 38, Aug. 29, 2012, pp. 15728-15731 (4 pages).
Farrell, J.M. et al., "Metal-Free Transfer Hydrogenation Catalysis by B(C6F5)3"; Published in Organometallics, vol. 30, Issue 17, Aug. 2, 2011, pp. 4497-4500 (4 pages).
Mahdi, T. et al., "Metal-Free Aromatic Hydrogenation: Aniline to Cyclohexyl-amine Derivatives"; Published in Journal of the American Chemical Society (JACS), vol. 134, Issue 9, Feb. 15, 2012, pp. 4088-4091 (4 pages).
Reddy, J.S. et al., "Alkenylborane-Derived Frustrated Lewis Pairs: Metal-Free Catalytic Hydrogenation Reactions of Electron-Deficient Alkenes"; Published in Organometallics, vol. 31, Issue 15, Jul. 17, 2012, pp. 5638-5649 (12 pages).
Morris, Robert H., "Asymmetric hydrogenation, transfer hydrogenation and hydrosilylation of ketones catalyzed by ron complexes"; Published in Chemical Society Reviews (ChemSocRev), vol. 38, Issue 8, May 28, 2009, pp. 2282-2291 (10 pages).

(56) References Cited

OTHER PUBLICATIONS

Junge, K. et al., "Homogeneous catalysis using iron complexes: recent developments in selective reductions"; Published in Journal of Chemical Communications (ChemComm), vol. 47, Issue 17, Mar. 24, 2011, pp. 4849-4859 (11 pages).
Darwish, M. et al., "Asymmetric catalysis using iron complexes—'Ruthenium Lite'?"; Published in Journal of Catalysis Science & Technology, vol. 2, Issue 2, Nov. 15, 2012, pp. 243-255 (13 pages).
Gopalaiah, K., "Chiral Iron Catalysts for Asymmetric Synthesis"; Published in Chemical Reviews, vol. 113, Issue 5, Mar. 5, 2013, pp. 32489-3296 (49 pages).
Lagaditis, P.O. et al., "Template Synthesis of Iron(II) Complexes Containing Tridentate P-N-S, P-N-P, P-N-N, and Tetradentate P-N-N-P. Ligands"; Inorganic Chemistry vol. 49, No. 3; pp. 1094-1102; Feb. 1, 2010 (9 pages).
Feng, R. et al., "Origins of enantioselectivity in asymmetric ketone hydrogenation catalyzed by a RuH2(binap)(cydn) complex: insights from a computational study"; Dalton Transactions, vol. 42; pp. 2130-2145; Published Nov. 7, 2012 (16 pages).
Chen et al., "The effects of ligand variation on enantioselective hydrogenation catalysed by RuH2(diphosphine) . (diamine) complexes"; Dalton Transactions, vol. 41; pp. 1867-1877; Published Dec. 14, 2011 (11 pages).
Evans, W.J. et al., "Synthetic and Structural Studies of Nonametallic tert-Butoxide Mixed-Metal Complexes of Yttrium, Europium, and Sodium: X-ray Crystal Structures of a New Class of LnNa8(OR)10X Complexes (Ln = Y, Eu; R = CMe3; X = CI, OH)"; J. Am. Chem. Soc.; pp. 4120-4127; Sep. 4, 1992 (8 pages).
Song, D. et al., "Cyclometalated Tridentate C-N-N Ligands with an Amine or Amido Donor in Platinum(II) and Palladium(II) Complexes and a Novel Potassium Alkoxide Aggregate"; Organometallics vol. 23; pp. 4406-4413; Published Aug. 20, 2004 (8 pages).
Malcolm H. Chisholm et al., "Synthesis and X-Ray Crystal Structures of the One-Dimensional Ribbon Chains [MOBut · ButOH]00 and the Cubane Species [MOBut]4 (M = K and Rb)"; Polyhedron vol. 10, No. 3; pp. 337-345; Accepted Sep. 27, 1990 (9 pages).
Faraj Hasanayn et al., "Symmetry Aspects of H2 Splitting by Five-Coordinate d6 Ruthenium Amides, and Calculations on Acetophenone Hydrogenation, Ruthenium Alkoxide Formation, and Subsequent Hydrogenolysis in a Model trans-Ru(H)2(diamine)(diphosphine) System"; Inorganic Chemistry vol. 51; pp. 10808-10818; Published Oct. 2, 2012 (11 pages).
Masato Ito et al., "Hydrogenation of Aromatic Ketones Catalyzed by (n5-C5(CH3)5)Ru Complexes Bearing Primary Amines"; American Chemical Society; Organometallics vol. 20; pp. 379-381; Published Jan. 10, 2001 (3 pages).
Yue Chen et al., "Nature of Asynchronous Hydrogen Transfer in Ketone Hydrogenation Catalyzed by Ru Complex"; American Chemical Society; J. Phys. Chem. C, vol. 112, No. 35; pp. 13524-13527; Published Aug. 12, 2008 (4 pages).
Xiaojia Guo et al., "Concerted or Stepwise Hydrogen Transfer in the Transfer Hydrogenation of Acetophenone Catalyzed by Ruthenium?? Acetamido Complex: A Theoretical Mechanistic Investigation"; The Journal of Physical Chemistry A, vol. 115; pp. 12321-12330; Published Oct. 5, 2011 (10 pages).
Marcello Bertoli et al., "PNP pincer osmium polyhydrides for catalytic dehydrogenation of primary alcohols"; Dalton Transactions, vol. 40; pp. 8941-8949; Published Apr. 26, 2011 (10 pages).
Theo Zweifel et al., "Catalyzed Dehydrogenative Coupling of Primary Alcohols with Water, Methanol, or Amines"; Angewandte Chemie International Edition, vol. 48, Issue 3; pp. 559-563; Published Jan. 5, 2009 (5 pages).
Theo Zweifel et al., "Ethanol as Hydrogen Donor: Highly Efficient Transfer Hydrogenations with Rhodium(I) Amides"; Angewandte Chemie International Edition, vol. 47, Issue 17; pp. 3245-3249; Published Apr. 14, 2008 (5 pages).
Lori S. Van Der Sluys et al., "An Attractive Cis-Effect of Hydride on Neighbor Ligands: Experimental and Theoretical Studies on the Structure and Intramolecular Rearrangements of Fe(H)2(n2-H2)(PEtPh2)3"; J. Am. Chem Soc., vol. 112, Issue 12; pp. 4831-4841; Published Jun. 1, 1990 (11 pages).

John S. Ricci et al., "Single-Crystal X-ray and Neutron Diffraction Studies of an n2-Dihydrogen Transition-Metal Complex: trans-[Fe(n2-H2)(H)(PPh2CH2CH2PPh2)2]BPh4"; J. Am. Chem. Soc., vol. 111; pp. 8823-8827; Mar. 14, 1989 (5 pages).
Nam Nhat Ho et al., "Neutron diffraction study of the highly distorted octahedral complex FeH2(CO)2[P(OPh)3]2"; Journal of Organometallic Chemistry, vol. 676; pp. 85-88; Apr. 17, 2003 (4 pages).
Zhenyang Lin et al., "Transition metal polyhydride complexes: a theoretical view"; Coordination Chemistry Reviews, 135/136; pp. 845-879; May 4, 1994 (35 pages).
Boris Rybtchinski et al., "Unexpected Isomerization of a cis- into a trans-Dihydride Complex. A Neutral Late Transition Metal Complex as a Hydride Donor"; Organometallics, vol. 16, No. 17; pp. 3786-3793; Feb. 11, 1997 (8 pages).
Robert Bau et al., "X-ray and Neutron Diffraction Studies of the Polyhydrido Complex FeH6Mg4Br3.5Cl0.5(C4H8O)8: Discussion of Binary Transition-Metal Hydride Anions of the Type [MHx]n-"; Inorganic Chemistry, vol. 23, No. 18; pp. 2823-2829; Published Aug. 1, 1984 (7 pages).
Peter E. Sues et al., "Rational development of iron catalysts for asymmetric transfer hydrogenation"; Dalton Transactions, vol. 43; pp. 7650-7667; Published Apr. 15, 2014 (18 pages).
Satoshi Takebayashi et al., "Desymmetrization of meso-Cyclic Imides via Enantioselective Monohydrogenation"; J. Am. Chem. Soc., vol. 132; pp. 12832-12834; Published Aug. 24, 2010 (3 pages).
Weiwei Zuo et al., "Iron Catalysts Containing Amine(imine)diphosphine P NH-N P Ligands Catalyze both the Asymmetric Hydrogenation and Asymmetric Transfer Hydrogenation of Ketones"; Organometallics, vol. 33, pp. 5791-5801, Published Jun. 13, 2014 (11 pages).
Extended European Search Report dated Sep. 18, 2017, received on corresponding European Patent Application No. 15735026.5 (5 pages).
Bryden A. F. Le Bailly et al., "Iron-catalysed reduction of carbonyls and olefins"; Royal Society of Chemistry; RSC Advances, vol. 1; pp. 1435-1445; Published Oct. 31, 2011 (11 pages).
Christine Sui-Seng et al., "Highly Efficient Catalyst Systems Using Iron Complexes with a Tetradentate PNNP Ligand for the Asymmetric Hydrogenation of Polar Bonds"; Angew. Chem. Int. Ed., vol. 47; pp. 940-943; Published Jan. 11, 2008 (4 pages).
Knolker, H. et al., "Transition Metal-Diene Complexes in Organic Synthesis, Part 14. Regioselective Iron-Mediated (2+ 2 +1) Cycloadditions of Alkynes and Carbon Monoxide: Synthesis of Substituted Cyclopentadienones"; Institut fur Organische Chemie, Universitat Karlsruhe, Richard-Willstatter-Allee, D-7500 Karlsruhe I, Germany, Oct. 14, 1992 (3 pages).
Knolker, H. et al., "Transition Metal-Diene Complexes in Organic Synthesis, Part 18. Iron-Mediated (2+2+1) Cycloadditions of Diynes and Carbon Monoxide: Selective Demetalation Reactions"; Institut fur Organische Chemie, Universitat Karlsruhe, Richard-Willstatter-Allee, D-76131 Karlsruhe I, Germany, Oct. 14, 1993 (3 pages).
Chakraborty, S. et al., "A Molecular Iron Catalyst for the Acceptorless Dehydrogenation and Hydrogenation of N-Heterocycles"; Journal of the American Chemical Society (JACS), May 30, 2014 (4 pages).
Bornschein, C. et al., "Mild and selective hydrogenation of aromatic and aliphatic (di)nitriles with a well-defined iron pincer complex"; Nature Communications, Jun. 27, 2014 (11 pages).
Liang, L. et al., "Phosphorus and Olefin Substituent Effects on the Insertion Chemistry of Nickel(II) Hydride Complexes Containing Amido Diphosphine Ligands", Organometallics, May 29, 2008 (12 pages).
Antberg, M. et al., "Oligophosphine Ligands, XII [1] Pseudohalo and Halohydro Complexes of Iron (II) Containing the Tripod Tetratertiary Phosphine Ligand P(CH2CH2CH2PMe2)3", Zeitschrift far Naturforschung B, A Journal of Chemical Sciences, vol. 40, Issue11, Jun. 19, 1985 (5 pages). Abstract is Concise Statement of Relevance.
Antberg, M. et al., "Oligophosphan-Liganden XXV *. cis-FeH2(P(CH2CH2CH2PMe2)3:Synthese und Reaktionen, Journal of Organometallic Chemistry", 338(3) Jan. 1988, pp. 319-327 (9 pages). Abstract is Concise Statement of Relevance.

(56) References Cited

OTHER PUBLICATIONS

Sellman, D. et al., "Reaktionen an Komplexgebundenen Liganden XXXVIII *. (CpFe(dppe)L]- UND (CpFe(cdpe)L]-KOMPLEXE MIT L = CO-, N2-, NH3-, HN3-, SOWIE N3 —Liganden (dppe = 1,2-Bis (DlPHENYLPHOSPIDNO)Ethan, cdpe = cis-1,2-Bis(Diphenylphosphino)Ethen)", Journal of Organometallic Chemistry, 304(1-2), Apr. 22, 1986, pp. 195-205 (11 pages). Abstract is Concise Statement of Relevance.

* cited by examiner

1 a) R = Cy;  b) R = iPr;  c) R = Ph

1) KO*t*Bu
2) FeBr$_2$
3) Ph$_2$PC$_2$H$_4$NH$_2$

CO (~1 atm)
THF

2 (trans-Br)    3 (cis-Br)

AgBF$_4$    CH$_2$Cl$_2$/THF
CO (~ 1 atm)

4 a) R = Cy;  b) R = *i*Pr;  c) R = Ph

H X = Br
I X = BH$_4$
J X = H

K X = Br
L X = BH$_4$
M X = H

R = iPr or cyclohexyl
N b) R = iPr, R' & R" = H
(S,S)-d) R = Cy, R' = Me, R" = Ph
R''' = Me, tAmyl, tBu

IRON(II) CATALYSTS CONTAINING TRIDENTATE PNP LIGANDS, THEIR SYNTHESIS, AND USE THEREOF

CROSS-REFERENCE TO RELATED APPLICATIONS

This is a national stage application of PCT/CA2015/050008, filed on Jan. 8, 2015, which claims priority to U.S. Patent Application Ser. No. 61/925,021, filed on Jan. 8, 2014. This application claims the benefits and priority of these prior applications and incorporates their disclosures by reference in their entireties.

FIELD OF THE INVENTION

The present application pertains to catalytic materials for hydrogenation or asymmetric hydrogenation. More particularly, the present application relates to iron(II) complexes containing tridentate diphosphine PNP ligands useful for catalytic hydrogenation.

INTRODUCTION

Current research in the field of catalytic hydrogenation has moved towards developing complexes that do not employ platinum group metals given their low abundance and toxicity, which makes them undesirable for some applications [*Catalysis without Precious Metals*; Bullock, R. M., Ed.; Wiley-VCH. Hoboken, N.J., 2010]. Several catalysts based on 3d metals have been shown to be competitive with precious metal based catalysts for asymmetric reduction of unsaturated bonds [Tondreau, A. M.; Darmon, J. M.; Wile, B. M.; Floyd, S. K.; Lobkovsky, E.; Chink, P. J. *Organometallics* 2009, 28, 3928-3940; Monfette, S.; Turner, Z. R.; Semproni, S. P.; Chirik, P. J. *J. Am. Chem. Soc.* 2012, 134, 4561-4564; Sylvester, K. T.; Chirik, P. J. *J. Am. Chem. Soc.* 2009, 131, 8772-8774; Wu, J. Y.; Stanzl, B. N.; Ritter, T. *J. Am. Chem. Soc.* 2010, 132, 13214-13216; Dong, Z. R.; Li, Y. Y.; Yu, S. L.; Sun, G. S.; Gao, J. X. *Chin. Chem. Lett.* 2012, 23, 533-536; Vasudevan, K. V.; Scott, B. L.; Hanson, S. K. *Eur. J. Inorg. Chem.* 2012, 4898-4906; Zhang, G.; Scott, B. L.; Hanson, S. K. *Angew. Chem. Int. Ed.* 2012, 51, 12102-12106; Harman, W. H.; Peters, J. C. *J. Am. Chem. Soc.* 2012, 134, 5080-5082; Federsel, C.; Ziebart, C.; Jackstell, R.; Baumann, W.; Beller, M. *Chem. Eur. J.* 2012, 18, 72-75; Werkmeister, S.; Fleischer, S.; Junge, K.; Beller, M. *Chem.—Asian J.* 2012, 7, 2562-2568]. Other systems based on enzymes [Huisman, G. W.; Liang, J.; Krebber, A. *Curr. Opin. Chem. Biol.* 2010, 14, 122-129; Savile, C. K.; Janey, J. M.; Mundorff, E. C.; Moore, J. C.; Tam, S.; Jarvis, W. R.; Colbeck, J. C.; Krebber, A.; Fleitz, F. J.; Brands, J.; Devine, P. N.; Huisman, G. W.; Hughes, G. J. *Science* 2010, 329, 305-309; Ringenberg, M. R.; Ward, T. R. *Chem. Commun.* 2011, 47, 8470-8476; Matsuda, T.; Yamanaka, R.; Nakamura, K. *Tetrahedron: Asymmetry* 2009, 20, 513-557], or metal-free compounds, have also shown promise [Stephan, D. W.; Greenberg, S.; Graham, T. W.; Chase, P.; Hastie, J. J.; Geier, S. J.; Farrell, J. M.; Brown, C. C.; Heiden, Z. M.; Welch, G. C.; Ullrich, M. *Inorg. Chem.* 2012, 50, 12338-12348; Rueping, M.; Dufour, J.; Schoepke, F. R. *Green Chem.* 2011, 13, 1084-1105; Sumerin, V.; Chernichenko, K.; Nieger, M.; Leskela, M.; Rieger, B.; Repo, T. *Adv. Synth. Catal.* 2011, 353, 2093-2110; Farrell, J. M.; Hatnean, J. A.; Stephan, D. W. *J. Am. Chem. Soc.* 2012, 134, 15728-15731; Farrell, J. M.; Heiden, Z. M.; Stephan, D. W. *Organometallics* 2011, 30, 4497-4500; Mandi, T.; Heiden, Z. M.; Grimme, S.; Stephan, D. W. *J. Am. Chem. Soc.* 2012, 134, 4088-4091; Reddy, J. S.; Xu, B.-H.; Mandi, T.; Fröhlich, R.; Kehr, G.; Stephan, D. W.; Erker, G. *Organometallics* 2012, 31, 5638-5649].

In recent years, a variety of iron-based hydrogenation catalysts have been developed [Morris, R. H. *Chem. Soc. Rev.* 2009, 38, 2282-2291; Junge, K.; Schroder, K.; Beller, M. *Chem. Commun.* 2011, 47, 4849-4859; Darwish, M.; Wills, M. *Catal. Sci. Technol.* 2012, 2, 243-255; Gopalaiah, K. *Chem. Rev.* 2013, 113, 3248-3296; Le Bailly, B. A. F.; Thomas, S. P. *RSC Adv.* 2012, 1, 1435-1445]. Morris et al. reported an iron complex that was moderately active for asymmetric hydrogenation of acetophenone under basic conditions, with a turnover frequency (TOF) of 5 h$^{-1}$ and an enantiomeric excess (ee) of 27% (S) (M1 of FIG. 1). The authors found that a monocarbonyl derivative of M1 was a good asymmetric transfer hydrogenation pre-catalyst for ketones [Sui-Seng, C.; Freutel, F.; Lough, A. J.; Morris, R. H. *Angew. Chem. Int. Ed.* 2008, 47, 940-943], and later, Beller et al. demonstrated that it also worked for activated imines [Zhou, S.; Fleischer, S.; Junge, K.; Das, S.; Addis, D.; Beller, M. *Angew. Chem. Int. Ed.* 2010, 49, 8121-8125].

Morris et al. also developed highly active and enantioselective iron(II) catalysts, [Fe(P—N—N—P)(CO)(Br)][BPh$_4$], where P—N—N—P was tetradentate ligand (S,S)-Ph$_2$PCH$_2$CHNC(H)PhC(H)PhNCHCH$_2$PPh$_2$, formed by condensation of an (S,S)-diamine with phosphine aldehydes templated by iron(II) [Mikhailine, A.; Lough, A. J.; Morris, R. H. *J. Am. Chem. Soc.* 2009, 131, 1394-1395; Mikhailine, A. A.; Morris, R. H. *Inorg. Chem.* 2010, 49, 11039-11044]. Morris et al. modified the ligand by substituting the phenyl substituents on phosphorus with alkyl or substituted phenyl substituents to examine effects on catalytic behavior [Lagaditis, P. O.; Lough, A. J.; Morris, R. H. *Inorg. Chem.* 2010, 49, 10057-10066; Sues, P. E.; Lough, A. J.; Morris, R. H. *Organometallics* 2011, 30, 4418-4431]; the resulting pre-catalysts were activated by base (KOtBu) to form bis-eneamido iron(II) complexes which were half reduced by isopropanol [Lagaditis, P. O.; Lough, A. J.; Morris, R. H. *J. Am. Chem. Soc.* 2011, 133, 9662-9665; Mikhailine, A. A.; Maishan, M. I.; Lough, A. J.; Morris, R. H. *J. Am. Chem. Soc.* 2012, 134, 12266-12280]. The pre-catalyst's ketone reduction was found to involved a bifunctional mechanism where the ligand was directly involved in catalysis [Mikhailine, A. A.; Maishan, M. I.; Lough, A. J.; Morris, R. H. *J. Am. Chem. Soc.* 2012, 134, 12266-12280; Prokopchuk, D. E.; Morris, R. H. *Organometallics* 2012, 31, 7375-7385]. Said catalysts were efficient at reduction of prochiral ketones by transfer hydrogenation with isopropanol, achieving TOFs of up to 55,000 h$^{-1}$, conversions of 98%, and enantioselectivity (ee) upwards of 90% for one enantiomer of the alcohol, at room temperature [Mikhailine, A. A.; Maishan, M. I.; Lough, A. J.; Morris, R. H. *J. Am. Chem. Soc.* 2012, 134, 12266-12280]. The catalysts were also active and enantioselective towards transfer hydrogenation of certain activated imines [Mikhailine, A. A.; Maishan, M. I.; Morris, R. H. *Org. Lett.* 2012, 14, 4638-4641].

Morris et al. determined that said transfer hydrogenation of ketones was occurring as an equilibrium process, sometimes resulting in product racemization. Therefore, a catalytic system was sought that utilized H$_2$ gas, thereby enabling irreversible hydrogenation of substrates with complete conversion to, and no racemization of, the product.

Kirchner et al. developed a synthesis for Fe(P—N—P)(CO)X$_2$ complexes, wherein P—N—P was a tridentate 2,6-(PiPr$_2$NH)$_2$C$_5$H$_3$N ligand, and X was Cl or Br [Benito-Garagorri, D.; Alves, L. G.; Puchberger, M.; Mereiter, K.;

Veiros, L. F.; Calhorda, M. J.; Carvalho, M. D.; Ferreira, L. P.; Godinho, M.; Kirchner, K. *Organometallics* 2009, 28, 6902-6914; Benito-Garagorri, D.; Puchberger, M.; Mereiter, K.; Kirchner, K. *Angew. Chem. Int. Ed.* 2008, 47, 9142-9145]. The authors found that when X was Cl, the cis isomer formed under solvent-free conditions, while the trans isomer formed in solution; however, when X was Br, a mixture of cis and trans isomers was always obtained. Kirchner et al. also reported a selective synthesis of trans-[Fe(P—N—P)(CO)$_2$(Br)][BF$_4$] complexes from a mixture of cis- and trans-Fe(P—N—P)(CO)(Br)$_2$ isomers via use of a halide abstractor (such as AgBF$_4$) [Benito-Garagorri, D.; Alves, L. G.; Veiros, L. F.; Standfest-Hauser, C. M.; Tanaka, S.; Mereiter, K.; Kirchner, K. *Organometallics* 2010, 29, 4932-4942].

Work by Milstein et al. demonstrated that iron(II) complexes comprising an achiral P—N—P ligand can be effective hydrogenation catalysts. The authors' iron(II) complexes, Fe{2,6-(PiPr$_2$CH$_2$)$_2$C$_5$H$_3$N}(H)(CO)(Br) (M2) [Langer, R.; Leitus, G.; Ben-David, Y.; Milstein, D. *Angew. Chem. Int. Ed.* 2011, 50, 2120-2124] and Fe{2,6-PiPr$_2$CH$_2$)$_2$C$_5$H$_3$N}(H)(CO)(HBH$_3$) (M3) [Langer, R.; Iron, M. A.; Konstantinovski, L.; Diskin-Posner, Y.; Leitus, G.; Ben-David, Y.; Milstein, D. *Chem. Eur. J.* 2012, 18, 7196-7209], shown in FIG. 1, were found to be active for catalytic hydrogenation of ketones under 4.1 atm H$_2$. Turnover numbers (TON) of up to 1720 were achieved for acetophenone hydrogenation, with TOF of approximately 430 h$^{-1}$ at 40° C. for M2; and, up to 1980 TON with a TOF of 300 h$^{-1}$ at 40° C. for M3. The latter complex did not require activation by base. A mechanistic investigation using experimental and DFT methods concluded that the catalysts operated by Milstein's established aromatization-dearomatization of P—N—P ligands, which had been previously demonstrated to occur with Ru analogues [Yang, X. *Inorg. Chem.* 2011, 50, 12836-12843; Gunanathan, C.; Ben-David, Y.; Milstein, D. *Science* 2007, 317, 790-792; Gunanathan, C.; Milstein, D. *Acc. Chem. Res.* 2011, 44, 588-602].

Knölker's Fe(II) complex was found by Casey et al. to catalyze ketone hydrogenation via a bifunctional mechanism using H$_2$ gas under mild conditions [Knölker, H.-J.; Heber, J. *Synlett* 1993, 1993, 924-926; Knölker, H.-J.; Heber, J.; Mahler, C. H. *Synlett* 1992, 1992, 1002-1004; Casey, C. P.; Guan, H. *J. Am. Chem. Soc.* 2007, 129, 5816-5817; Casey, C. P.; Guan, H. *J. Am. Chem. Soc.* 2009, 131, 2499-2507]. Berkessel et al. synthesized a chiral analogue of Knölker's complex by replacing a CO ligand with chiral phosphoramidite ligands (B1, FIG. 1) [Berkessel, A.; Reichau, S.; von der Höh, A.; Leconte, N.; Neudörfl, J.-M. *Organometallics* 2011, 30, 3880-3887], while Beller et al. added a chiral phosphoric acid as a co-catalyst (B2, FIG. 1) [Zhou, S.; Fleischer, S.; Junge, K.; Beller, M. *Angew. Chem. Int. Ed.* 2011, 50, 5120-5124; Fleischer, S.; Werkmeister, S.; Zhou, S.; Junge, K.; Beller, M. *Chem. Eur. J.* 2012, 18, 9005-9010]. The Berkessel system hydrogenated acetophenone with UV irradiation under 10 atm H$_2$ at 25° C., with 9 turnovers in 24 h to give 1-phenylethanol in 30% ee; the Beller system produced chiral amines in up to 96% ee under 50 atm H$_2$ at 65° C., with 16 turnovers based on iron in 24 hours.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

It is an object of the present invention to provide catalytic complexes that are useful for hydrogenation or asymmetric hydrogenation. It is another object of the present invention to provide iron (II) complexes containing tridentate phosphorus-nitrogen-phosphorus (P—N—P) ligands useful for the catalytic hydrogenation or asymmetric hydrogenation of ketones, aldehydes and imines.

In accordance with one aspect of the application, there is provided a complex of formula (I)

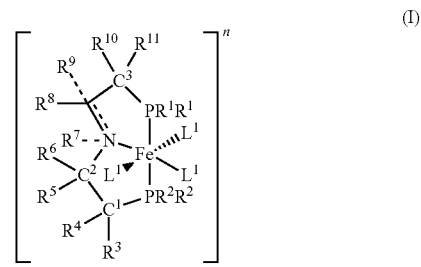

wherein:
a dashed line indicates that a bond may or may not be present;
each R$^1$ is independently C$_1$-C$_{10}$ alkyl, C$_2$-C$_{10}$ alkenyl, C$_1$-C$_8$ alkoxy, C$_3$-C$_{10}$ cycloalkyl, aryl, or heteroaryl, each of which may be optionally substituted; or the two geminal R$^1$ substituents combine to form a C$_2$-C$_4$ linear alkyl diradical or C$_3$-C$_{10}$ branched alkyl diradical, each of which may be optionally substituted, such that the two R$^1$ substituents, together with the phosphorus atom to which they are attached, form a ring;
each R$^2$ is independently aryl, heteroaryl, C$_1$-C$_{10}$ alkyl, C$_2$-C$_{10}$ alkenyl, C$_1$-C$_{10}$ alkoxy, aryloxy, or C$_3$-C$_{10}$ cycloalkyl, each of which may be optionally substituted; or the two geminal R$^2$ groups combine to form a C$_2$-C$_4$ linear alkyl diradical or C$_3$-C$_{10}$ branched alkyl diradical, each of which may be optionally substituted, such that the two R$^2$ substituents, together with the phosphorus atom to which they are attached, form a ring;
R$^3$, R$^4$, R$^5$, R$^6$, R$^8$, R$^9$, R$^{10}$ and R$^{11}$ are each independently H, or C$_1$-C$_{10}$ alkyl, C$_2$-C$_{10}$ alkenyl, aryl, heteroaryl, or C$_3$-C$_{10}$ cycloalkyl, each of which may be optionally substituted; or, R$^3$ and R$^4$, R$^5$ and R$^6$, and/or R$^{10}$ and R$^{11}$, together with the carbon atoms to which they are attached, form a substituted C$_5$-C$_{10}$ cycloalkyl ring;
R$^7$ is absent, H, AlH$_3$, or AlH$_5$;
each L$^1$ is independently H, BH$_4$, AlH$_4$, a halide, CO, an N-heterocyclic carbene, OR$^{12}$, or NCR$^{13}$, wherein R$^{12}$ and R$^{13}$ are independently C$_1$-C$_{10}$ alkyl, C$_2$-C$_{10}$ alkenyl, aryl, heteroaryl, or C$_3$-C$_{10}$ cycloalkyl, each of which may be substituted; or, one of L$^1$ may be absent;
when R$^7$ is AlH$_3$ or AlH$_5$, at least one of the H may bridge with Fe to form a cycle together with the atoms to which they are attached;
n is 0, +1, or −1, wherein, when n is +1, the complex further comprises at least one non-coordinating anion, Y; and, when n is −1, the complex further comprises at least one non-coordinating cation, Z; such that the total charge of the complex is 0;
with the proviso that, when the nitrogen is singly bound to the carbon attached to R$^9$, each of R$^3$ to R$^{11}$ are H, one $L^1$ is CO, and the other two $L^1$ is are Br, or Br and H, or $BH_4$ and H, then the $R^1$ and $R^2$ substituents cannot all be isopropyl; and with the proviso that, when the nitrogen is singly bound to the carbon attached to $R^9$, each of $R^3$ to $R^{11}$ are H, $R^7$ is absent, one $L^1$ is absent, one of $L^1$ is CO, and one of $L^1$ is H, then the $R^1$ and $R^2$ substituents cannot all be isopropyl.

In one embodiment of the complex of formula (I), with the proviso that, when the nitrogen is singly bound to the carbon attached to $R^9$, each of $R^3$ to $R^{11}$ are H, one $L^1$ is CO, and the other two $L^1$'s are Br, or Br and H, or $BH_4$ and H, the $R^1$ and $R^2$ substituents cannot all be cyclohexyl. In another embodiment of the complex of formula (I), with the proviso that, when the nitrogen is singly bound to the carbon attached to $R^9$, each of $R^3$ to $R^{11}$ are H, $R^7$ is absent, one $L^1$ is absent, one of $L^1$ is CO, and one of $L^1$ is H, the $R^1$ and $R^2$ substituents cannot all be cyclohexyl.

In accordance with one embodiment, there is provided a complex having the structure of formula (Ia):

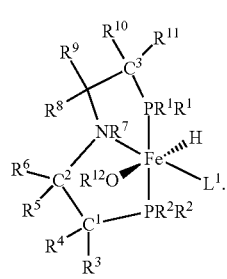

(Ia)

In accordance with another embodiment, there is provided a complex having the structure of formula (Ib) or (Ic):

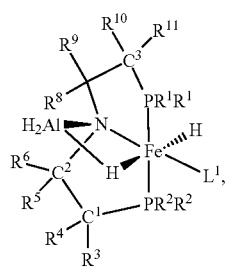

(Ib)

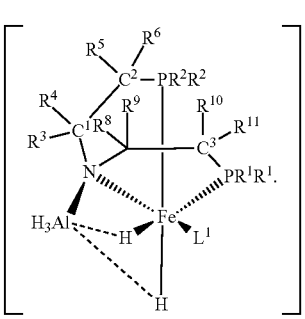

(Ic)

In accordance with another embodiment, there is provided a complex having the structure of formula (Id):

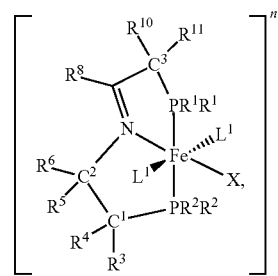

(Id)

wherein X is a halide.

In accordance with another embodiment, there is provided a complex having the structure of formula (Ie) or (If):

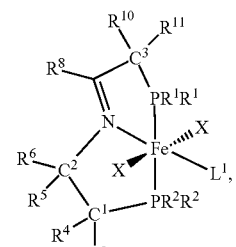

(Ie)

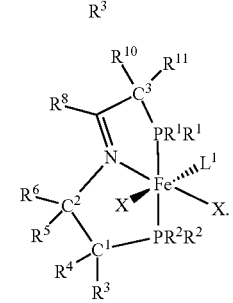

(If)

In accordance with another embodiment, there is provided a complex having the structure of formula (Ig) or (Ih):

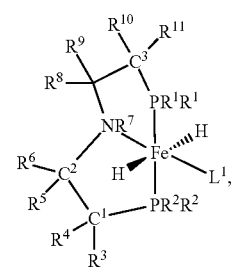

(Ig)

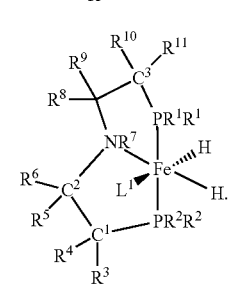

(Ih)

In accordance with another embodiment, there is provided a complex having the structure of formula (Ii):

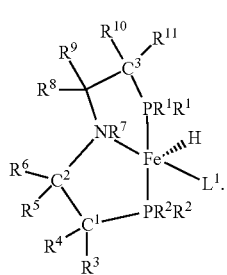

(Ii)

In accordance with another embodiment, there is provided a complex wherein each $R^1$ is independently $C_1$-$C_8$ alkyl or $C_3$-$C_8$ cycloalkyl; or, alternatively $C_1$-$C_4$ alkyl or $C_3$-$C_6$ cycloalkyl; and, each $R^2$ is independently aryl, or heteroaryl. In another embodiment, both of the $R^1$ substituents are either isopropyl or cyclohexyl; and, both of the $R^2$ substituents are phenyl.

In accordance with another embodiment, there is provided a complex wherein $R^3$ and $R^6$ are each independently H, $C_1$-$C_8$ alkyl, aryl, or heteroaryl; or, alternatively H, $C_1$-$C_4$ alkyl, aryl, or heteroaryl; and, each of $R^4$, $R^5$, $R^8$, $R^{10}$ and $R^{11}$ is H. In one embodiment, $R^3$ and $R^6$ are each independently H, methyl, or phenyl.

In accordance with another embodiment, there is provided a complex wherein $R^{12}$ is $C_1$-$C_8$ alkyl, $C_2$-$C_8$ alkenyl, $C_3$-$C_{10}$ cycloalkyl, aryl, or heteroaryl; or, alternatively, $R^{12}$ is $C_1$-$C_4$ alkyl, $C_2$-$C_4$ alkenyl, $C_3$-$C_6$ cycloalkyl, aryl, or heteroaryl. In one embodiment, $R^{12}$ is methyl, ethyl, t-butyl, or t-amyl.

In accordance with another embodiment, there is provided a complex wherein the non-coordinating cation, Z, is an alkali metal cation, such as $K^+$, $Na^+$ or $Li^+$.

In accordance with another embodiment, there is provided a complex wherein the non-coordinating anion, Y, is a conjugate base of a strong acid, such as a halide, $BF_4^-$, $PF_6^-$, $SbF_6^-$, $NO_3^-$, $ClO_4^-$, $CF_3COO^-$, $R^{14}SO_3^-$, $CF_3SO_3^-$, $C_6H_5SO_3^-$, p-$CH_3C_6H_4SO_3^-$, phosphates, TRISPHAT(Δ- or Λ-P(OC$_6$Cl$_4$O)$_3^-$), carboranes, $B(R^{14})_4^-$, or $Al(R^{14})_4^-$, each of which may be substituted, wherein each $R^{14}$ is independently an optionally substituted $C_1$-$C_6$ alkyl, aryl, heteroaryl, $C_6H_3(CF_3)_2$ and $C_6F_5$, halogen, pseudohalogen, $C_1$-$C_8$ alkoxide, or aryloxide. In one embodiment, Y is $BF_4^-$.

In accordance with another embodiment, there is provided a complex having the formula of (I), (Ia), (Ib), (Ic), (Id), (Ie), or (If), wherein carbon $C^1$, $C^2$ or $C^3$, or any combination thereof, is chiral, and the complex is enantiomerically enriched, or a racemate. In another embodiment, there is provided chiral complexes:

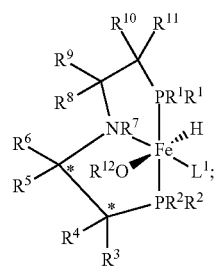

(Ia')

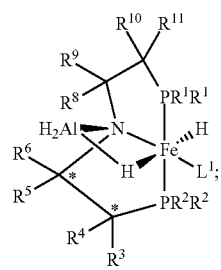

(Ib')

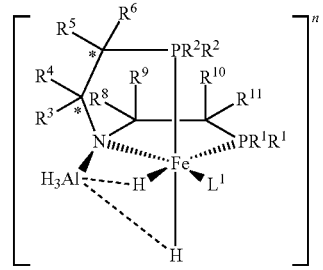

(Ic')

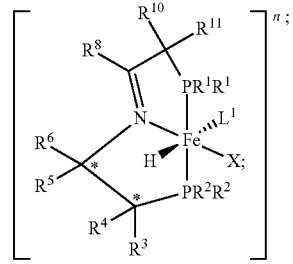

(Id')

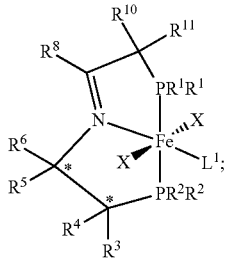

(Ie')

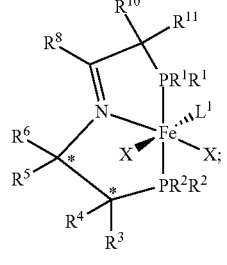

(If')

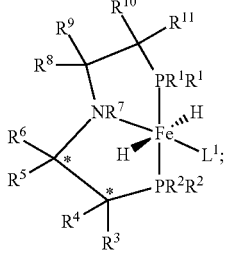

(Ig')

-continued

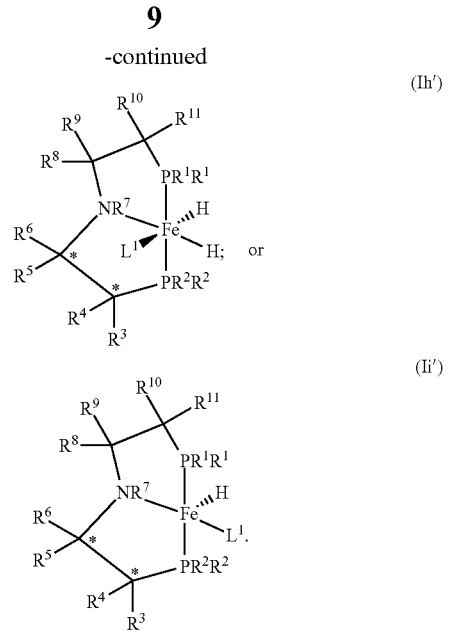

(Ih')

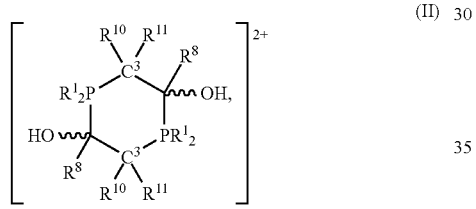

(Ii')

In accordance with another aspect, there is provided a process for preparing any one of the complexes (I), and (Ia)-(If), comprising reacting a phosphine-aldehyde precursor of formula (II)

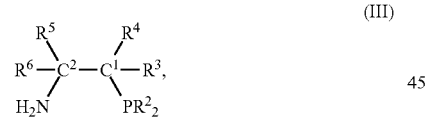

(II)

wherein $R^1$, $R^8$, $R^{10}$, and $R^{11}$ are as defined above, with a phosphine-amine of formula (III)

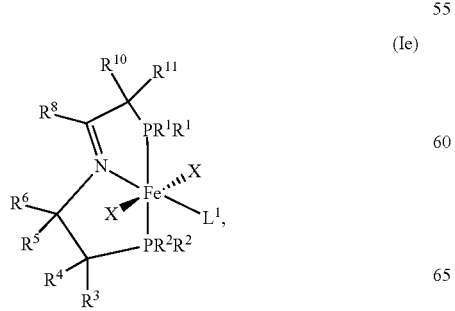

(III)

wherein $R^2$, $R^3$, $R^4$, $R^5$, and $R^6$ are as defined above,
in the presence of
an iron(II) compound,
a CO atmosphere, and
a strong base,
to form a complex of formula (Ie), or to form a mixture of complexes of formula (Ie) and formula (If),

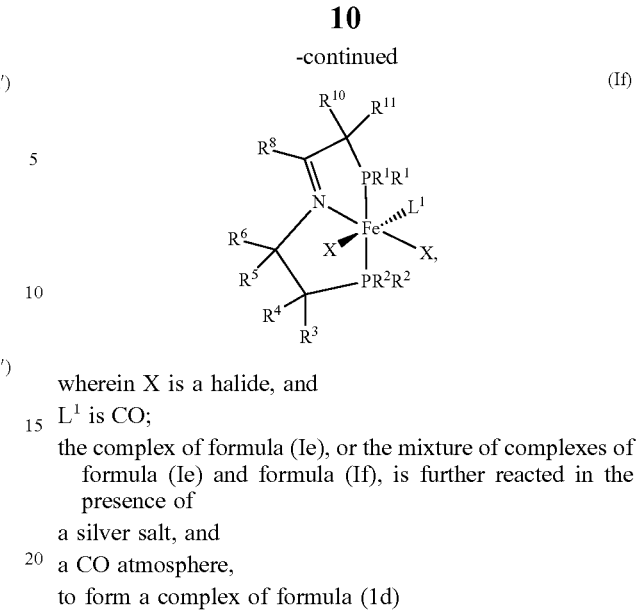

(If)

wherein X is a halide, and
$L^1$ is CO;
the complex of formula (Ie), or the mixture of complexes of formula (Ie) and formula (If), is further reacted in the presence of
a silver salt, and
a CO atmosphere,
to form a complex of formula (1d)

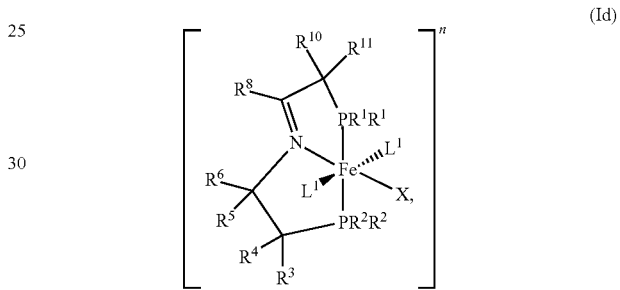

(Id)

which is further reacted in the presence of a reducing agent to form the complex of formula (Ib) and/or (Ic)

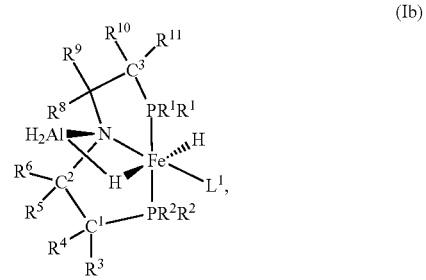

(Ib)

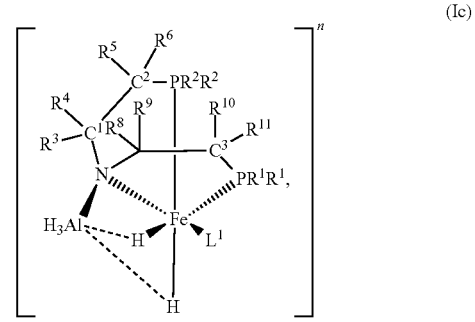

(Ic)

wherein $R^9$ is H,
which are further reacted with an excess of a primary, secondary, or tertiary alcohol, to form the complex of formula (Ia)

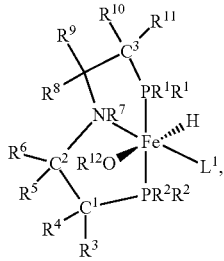

(Ia)

wherein R[7] and R[12] are as defined above.

In accordance with another embodiment, there is provided a process wherein carbon C[1] and/or C[2] of the phosphine-amine of formula (III) is chiral; and/or carbon C[3] of the phosphine-aldehyde precursor of formula (II) is chiral; and, the compound of which they are a part is enantiomerically enriched, or a racemate.

In accordance with another embodiment, there is provided a process wherein the iron(II) compound is an iron(II) salt; or, an iron(II) complex. In another embodiment, the iron(II) salt is $FeBr_2$ or $FeCl_2$; or, the iron(II) complex is $Fe(CO)_4Br_2$, wherein $Fe(CO)_4Br_2$ is additionally reacted in the presence of UV radiation to aid in formation of the complex of formula (Ie); or, to form a mixture of complexes of formula (Ie) and formula (If).

In accordance with another embodiment, there is provided a process wherein the strong base is KO$^t$Bu, the silver salt is AgBF$_4$, the reducing agent is LiAlH$_4$ or NaAlH$_4$, and the alcohol is MeOH, EtOH, $^t$BuOH, or $^t$AmylOH.

In accordance with another aspect, there is provided a process for preparing any one of the complexes (Ig)-(Ih), comprising reacting a complex of formula (Ia)

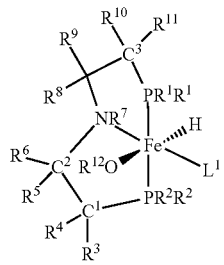

(Ia)

wherein R[1], R[2], R[3], R[4], R[5], R[6], R[7], R[8], R[10], R[11], R[12] and L[1] are as defined above,
in the presence of
a base, and
a H$_2$ atmosphere
to form a complex of formula (Ig) and/or a complex of formula (Ih),

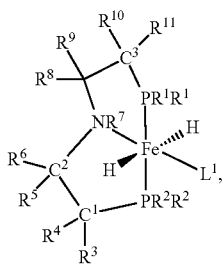

(Ig)

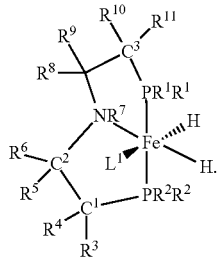

(Ih)

In accordance with another embodiment, there is provided a process wherein carbon C[1], C[2] or C[3], or any combination thereof, of complexes of formula (Ia), (1g), or (1h) is chiral, and the complex is enantiomerically enriched, or a racemate.

In accordance with another embodiment, there is provided a process wherein the base is KOtBu, NaOtBu, Ph-CH(OK)CH$_3$, or NaOMe.

In accordance with another aspect, there is provided a use of any one of the complexes described herein, prepared by the process described herein, as a hydrogenation pre-catalyst or hydrogenation catalyst to hydrogenate a substrate, wherein the substrate is a ketone, aldehyde, or imine.

In accordance with another embodiment, there is provided a use wherein the hydrogenation pre-catalyst or hydrogenation catalyst is chiral and the hydrogenation is an asymmetric hydrogenation.

In accordance with another aspect, there is provided a method for hydrogenation of a substrate comprising contacting the substrate with a hydrogen source in the presence of a complex described herein, under conditions suitable for hydrogenation.

In accordance with another embodiment, there is provided a method for hydrogenation wherein the substrate is a ketone, aldehyde, or imine, and the hydrogen source is hydrogen gas at a pressure >0 atm and less than <70 atm.

BRIEF DESCRIPTION OF THE TABLES AND FIGURES

For a better understanding of the technology as described herein, as well as other aspects and further features thereof, reference is made to the following description which is to be used in conjunction with the accompanying drawings and tables, where:

Table 1 delineates hydrogenation of acetophenone catalyzed by achiral complexes 4a-b once activated by reaction with LiAlH$_4$ and then alcohol;

Table 2 delineates reactivity of various ketones in an asymmetric hydrogenation reaction using an in situ generated catalyst derived from (S,S)-4d;

Table 2a delineates an asymmetric hydrogenation of acetophenone using an in situ generated chiral catalyst; and Table 3 delineates enantio-determining step (EDS) transition state energies calculated using different functionals.

Figure 3:
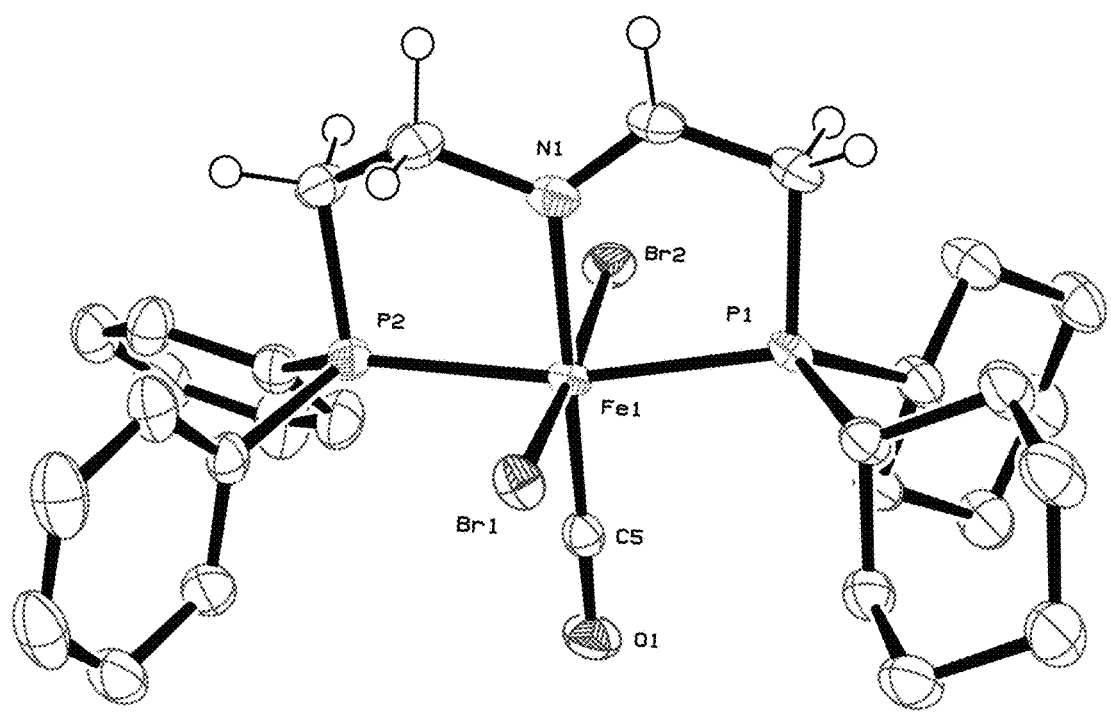
Figure 4A:
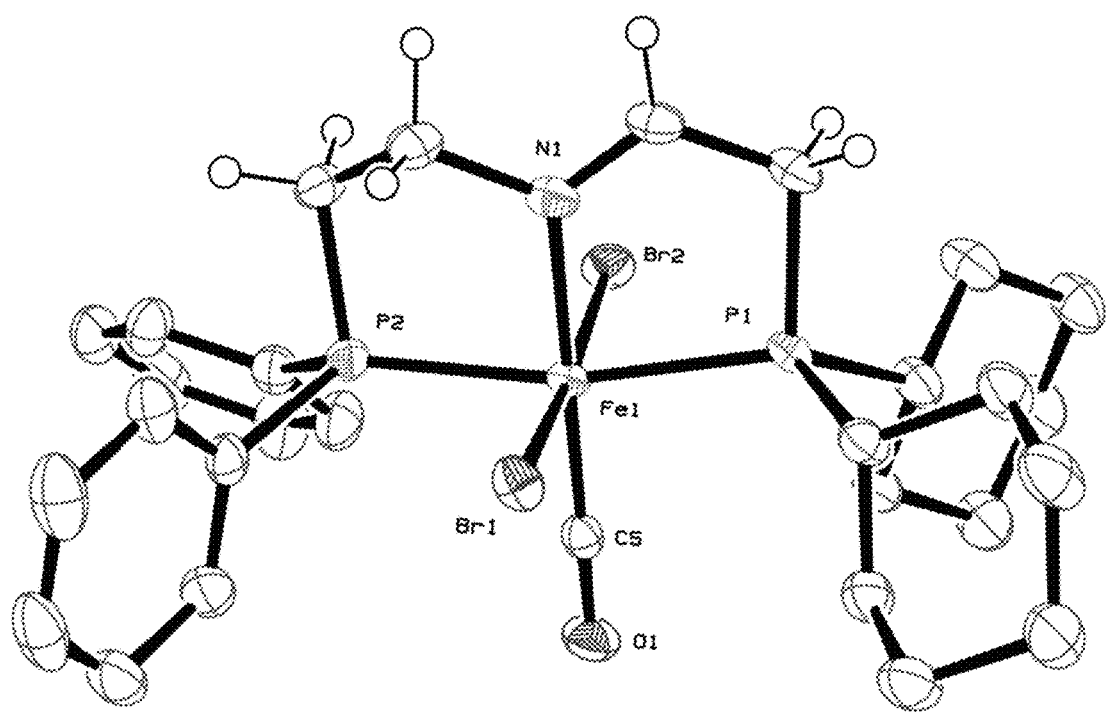
Figure 4B:
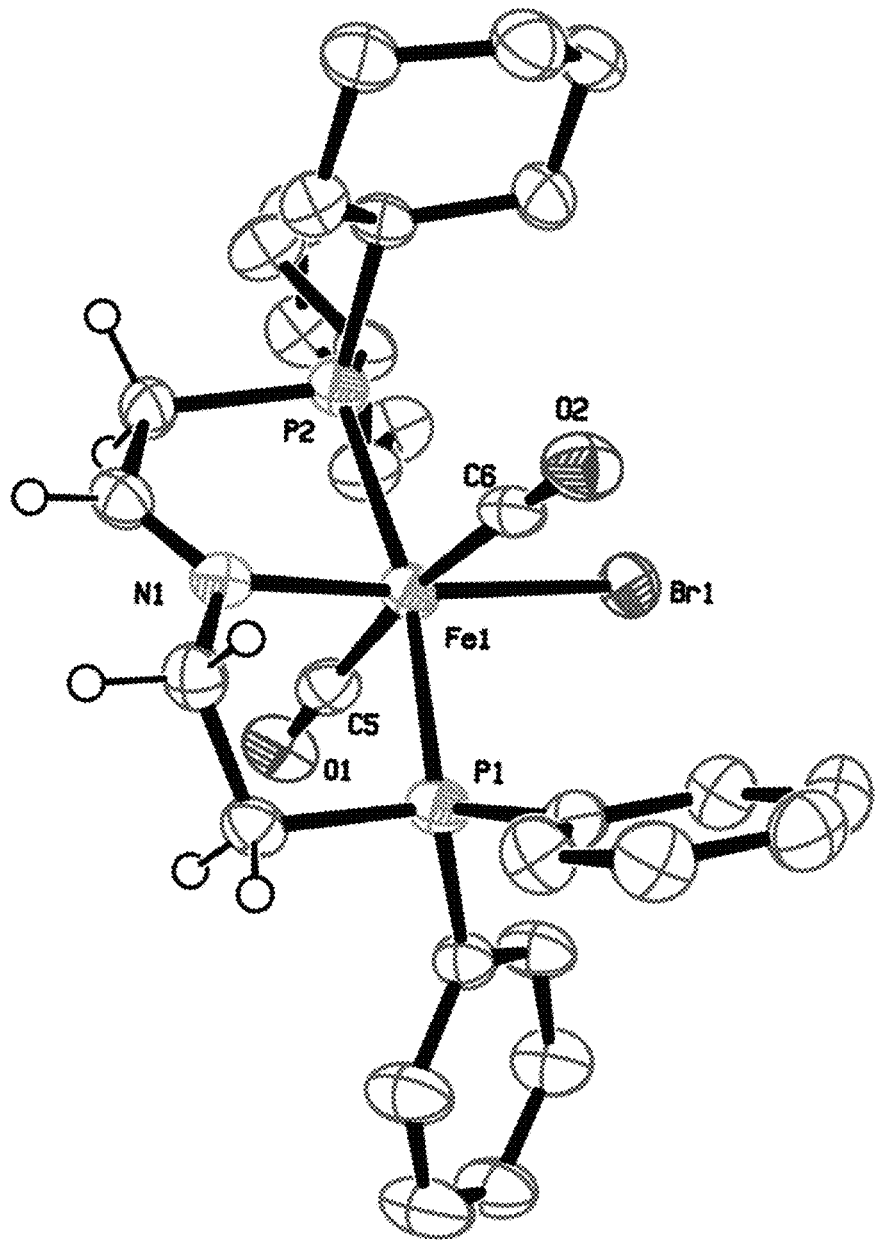
Figure 4C:
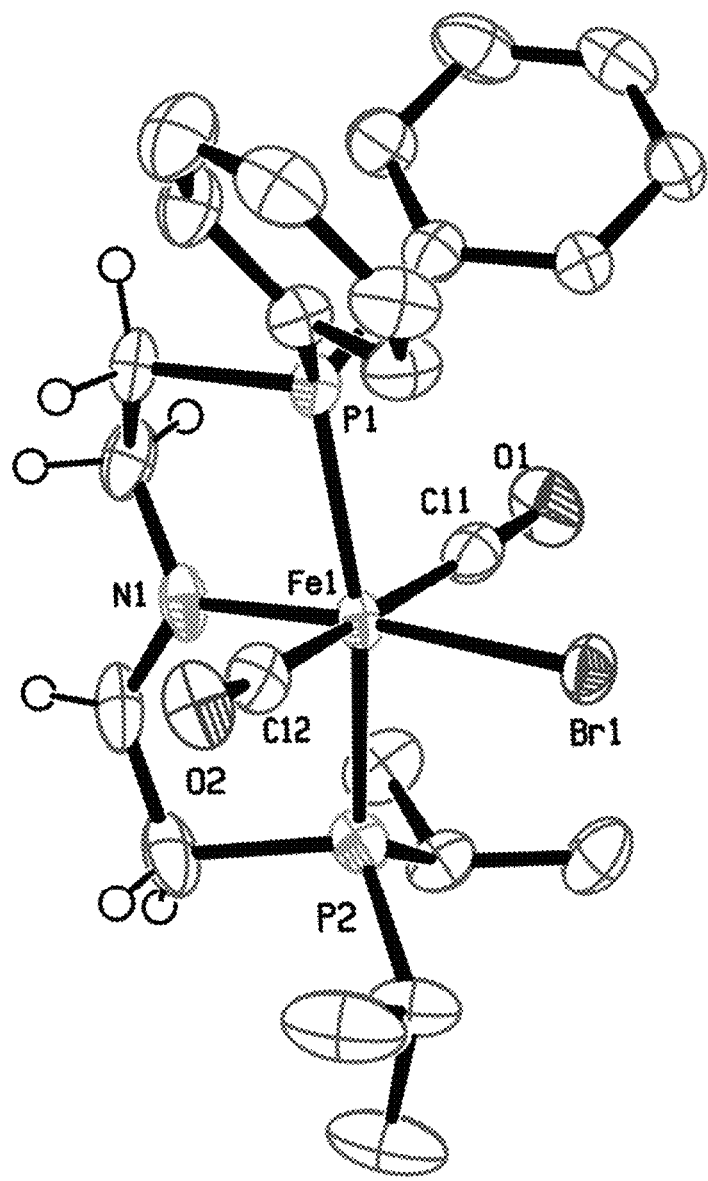
Figure 4D:
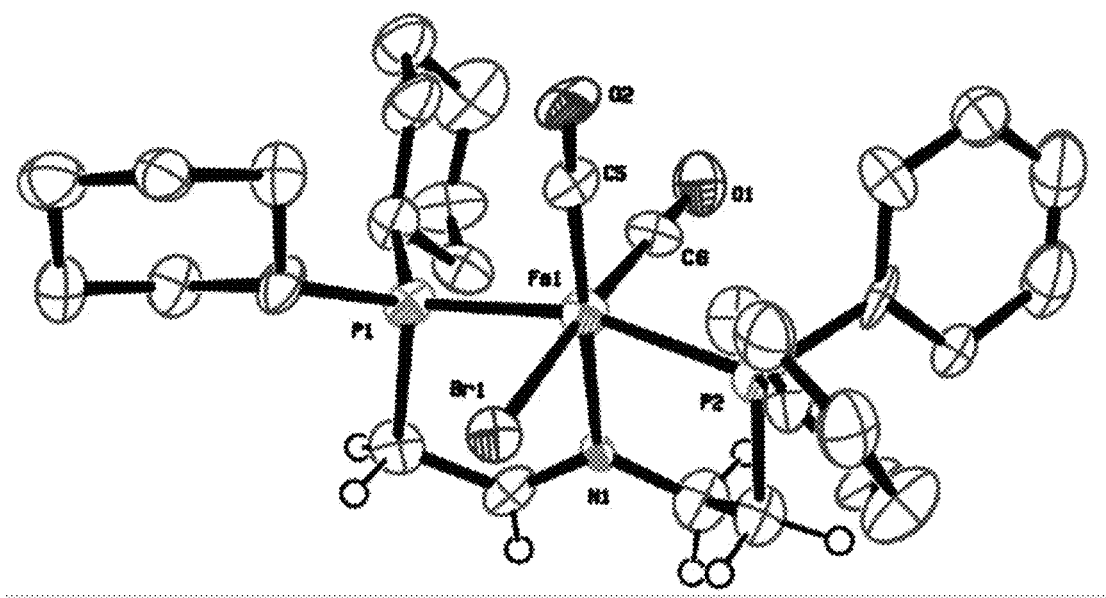
Figure 5:
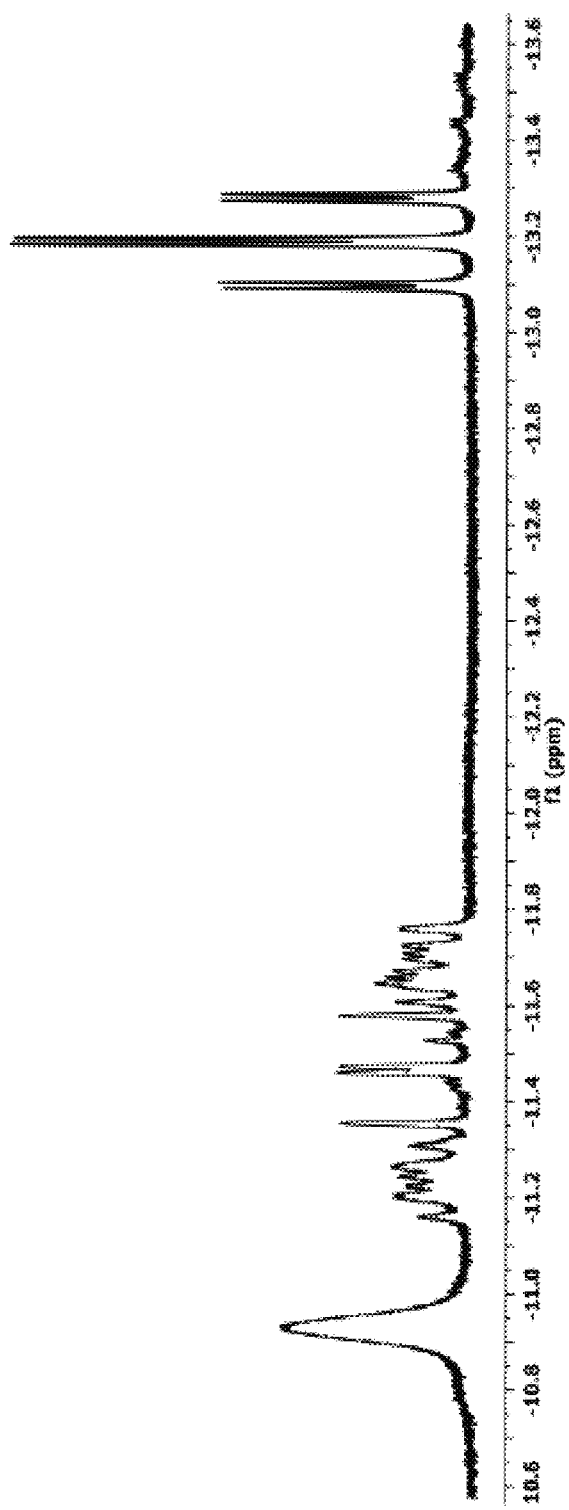
Figure 6:
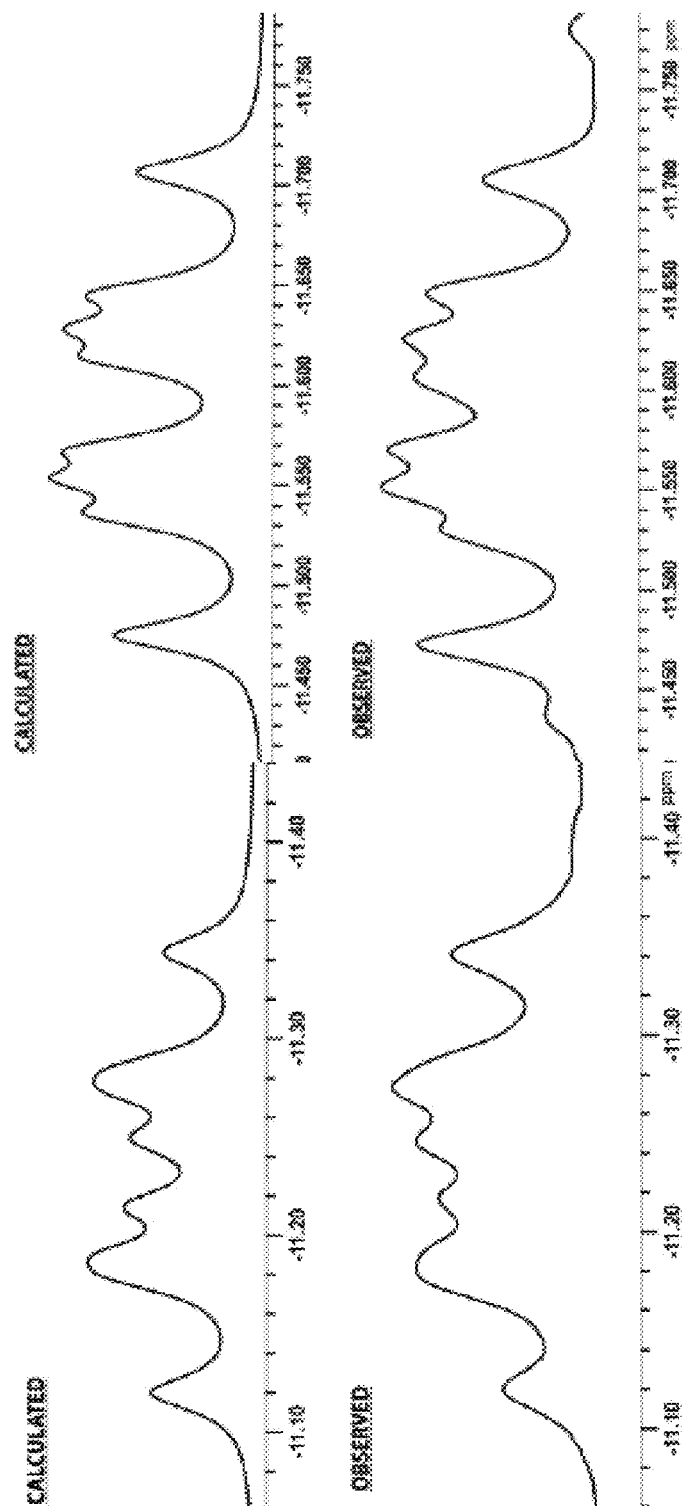
Figure 7:
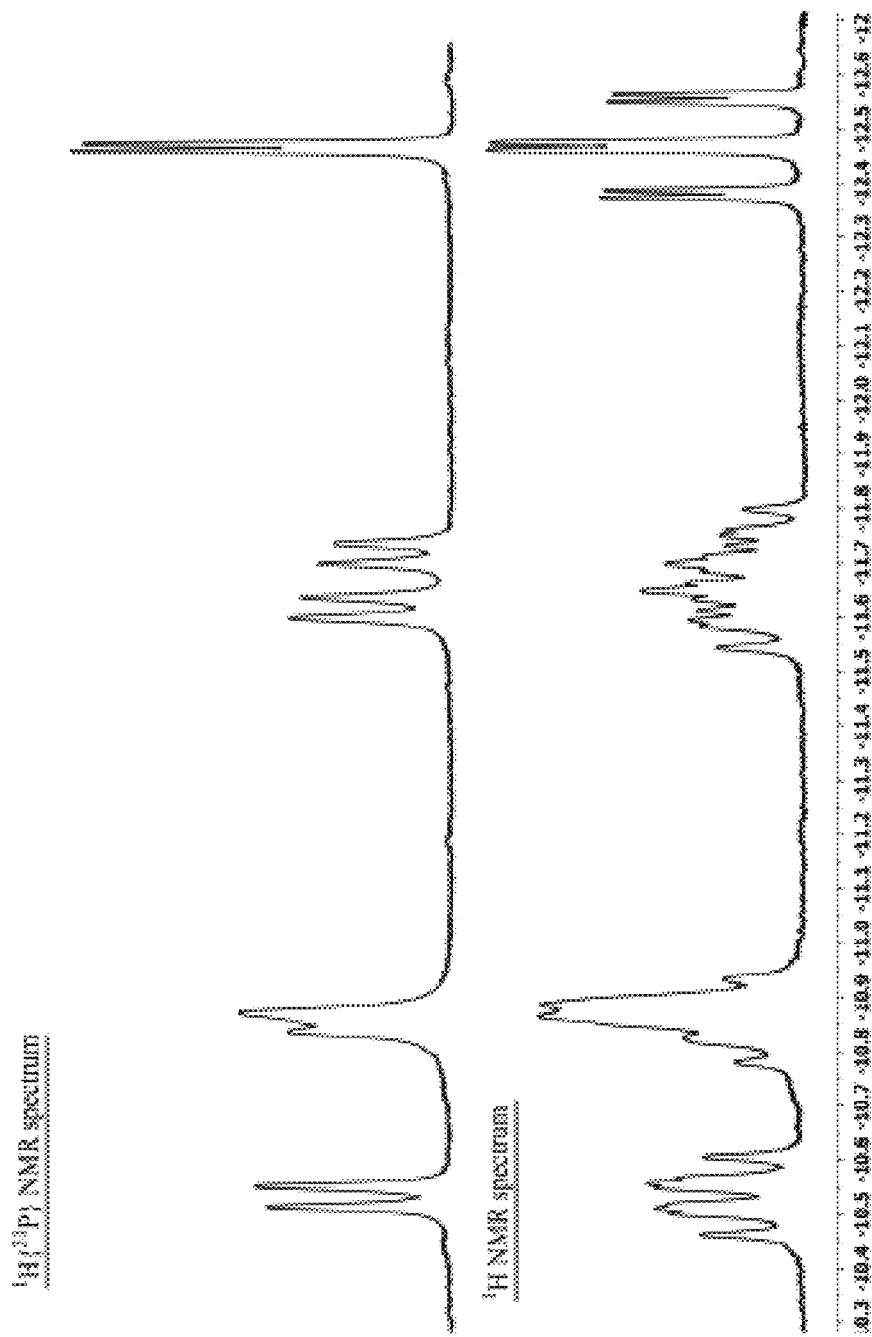
Figure 8:
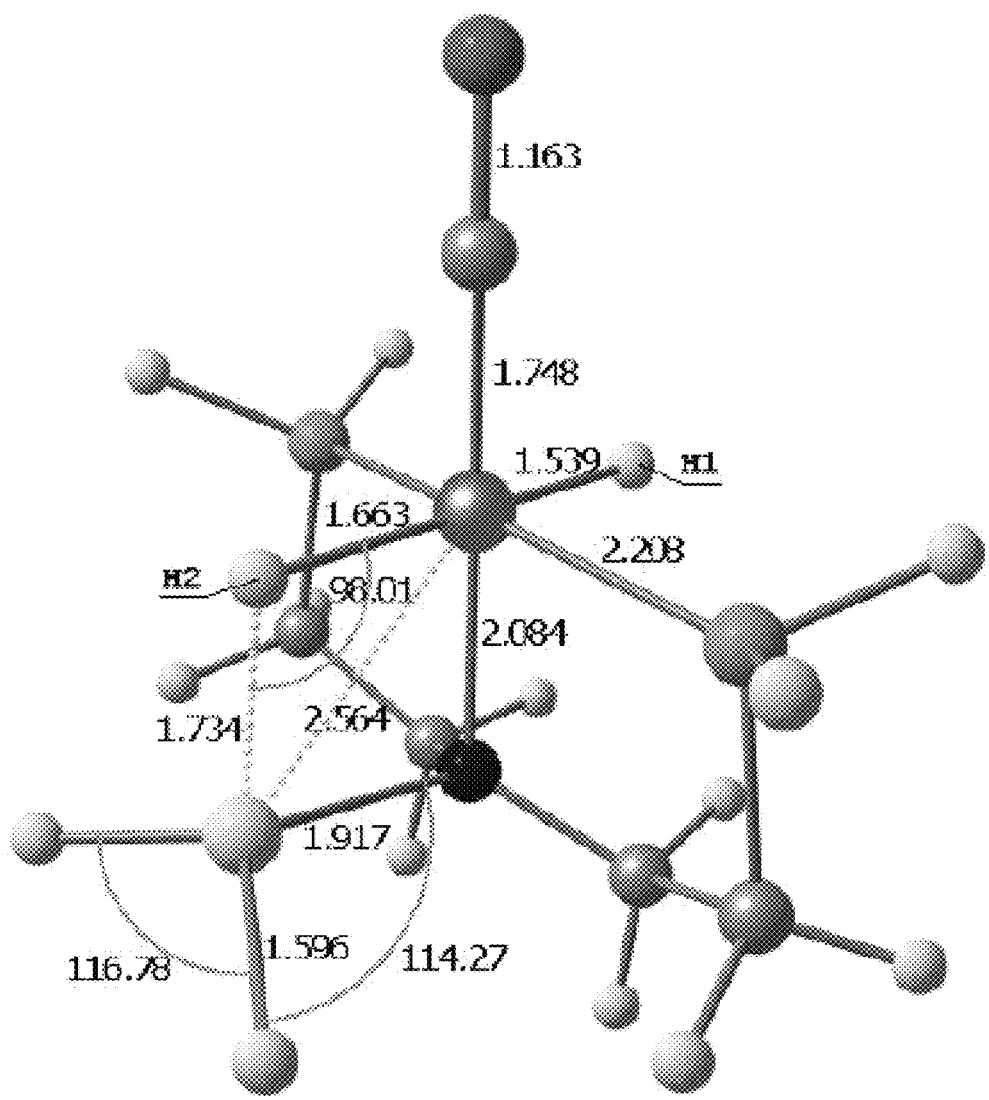
Figure 9A:
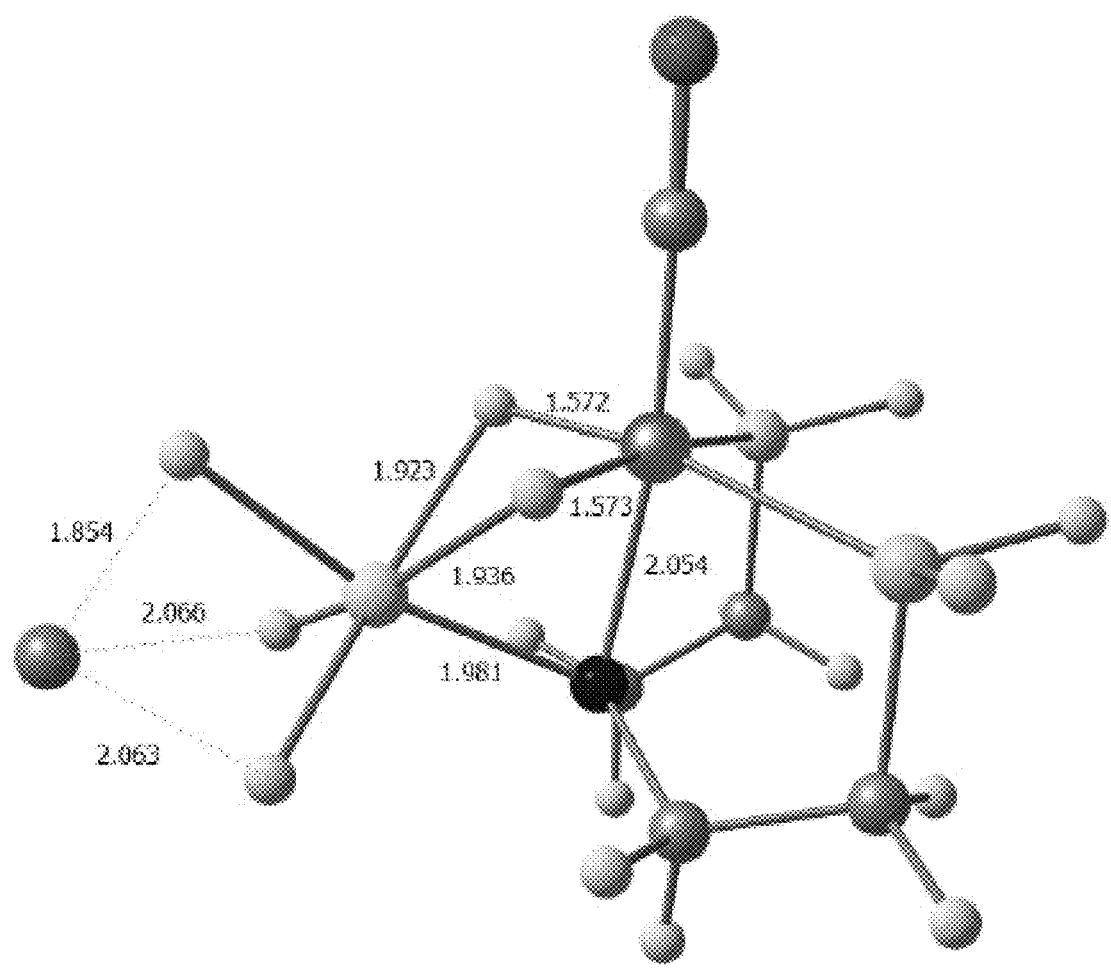
Figure 9B:
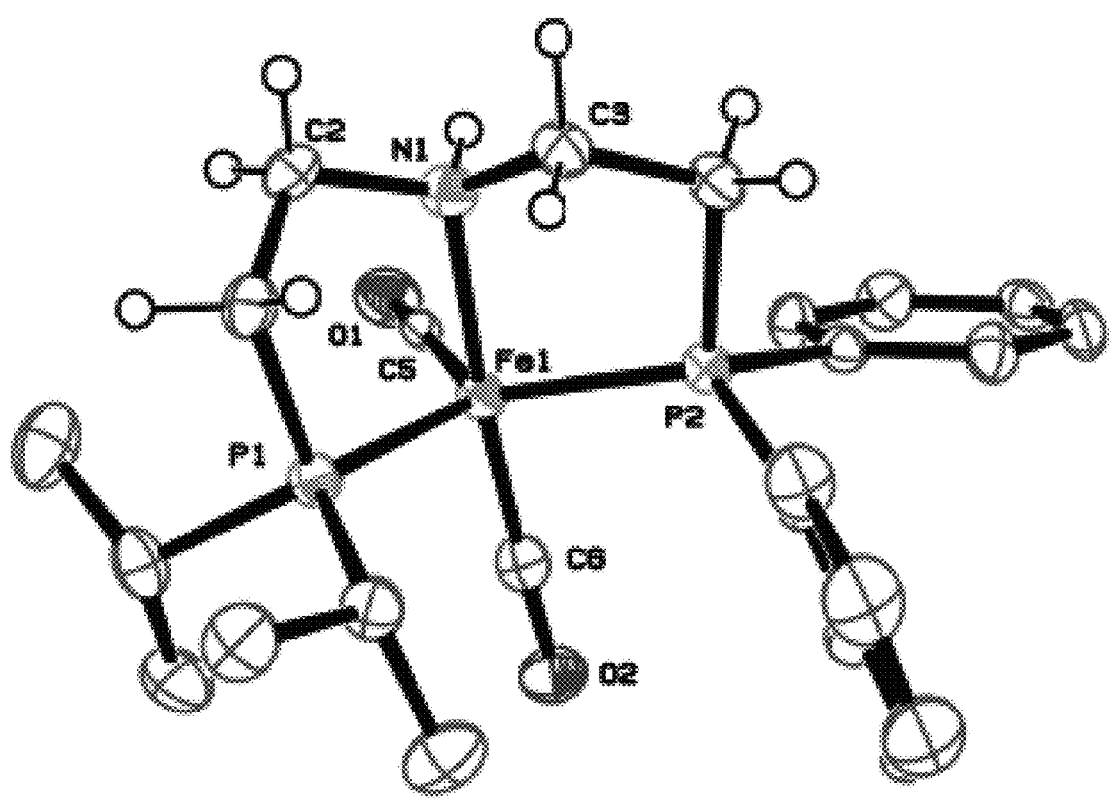
Figure 10A:
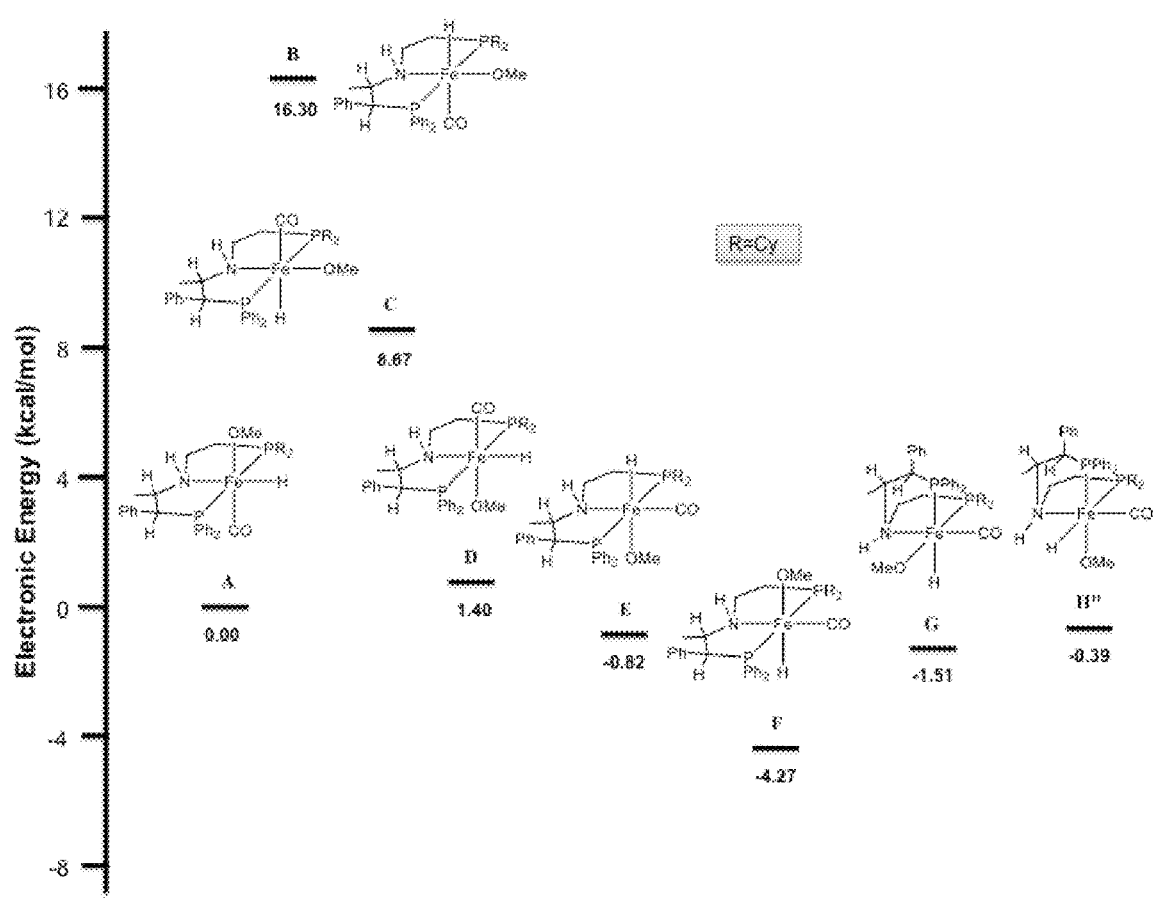
Figure 10B:
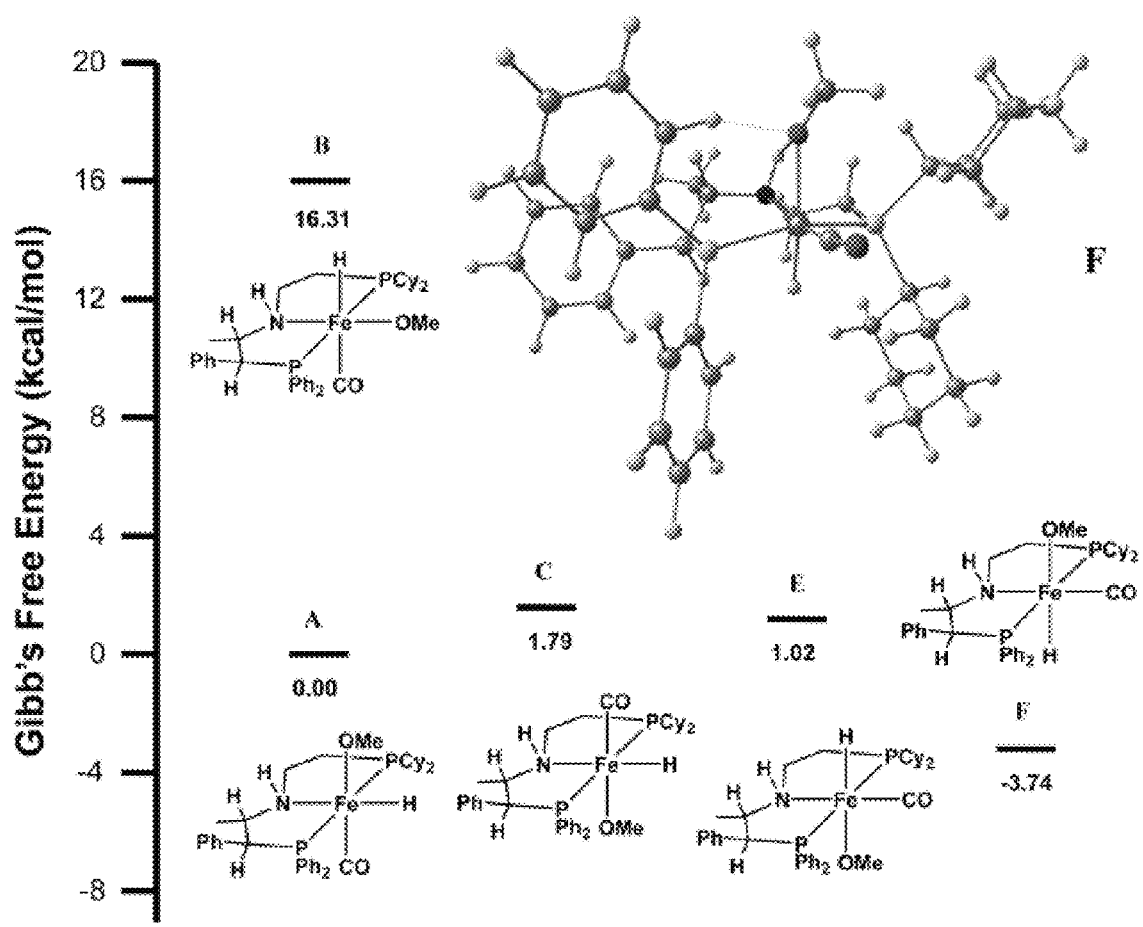
Figure 11:
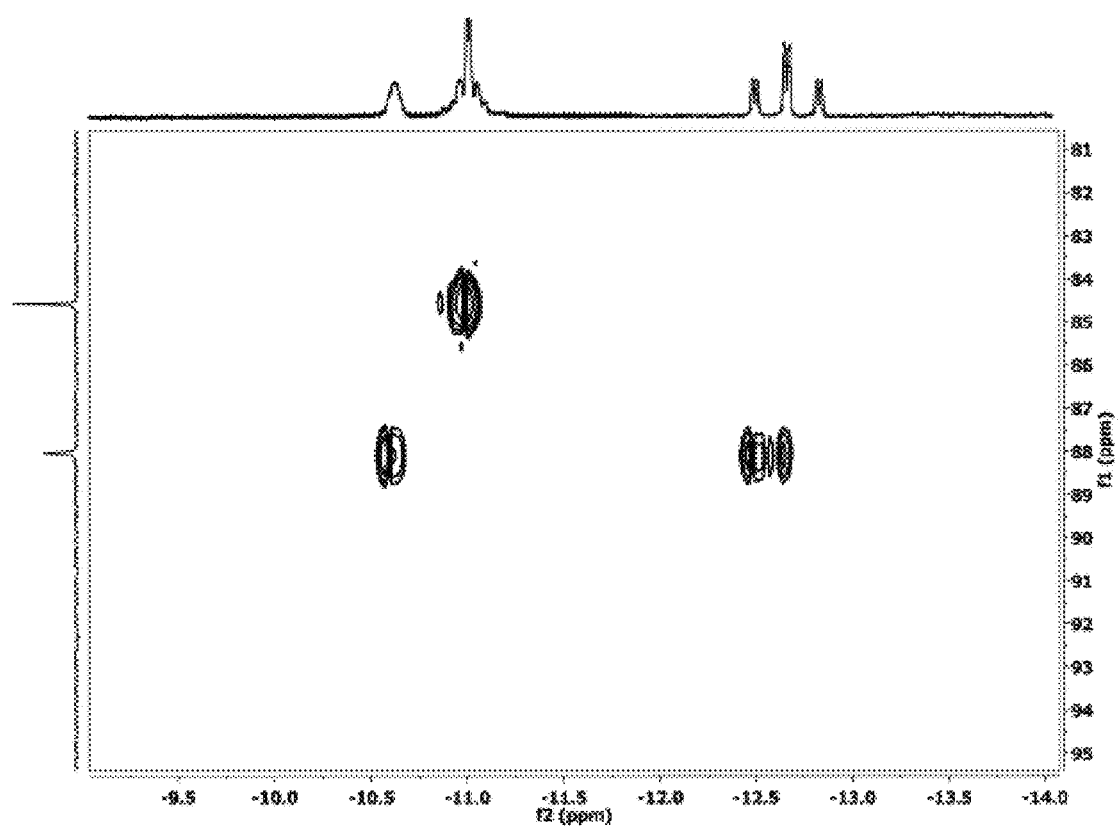
Figure 12A:
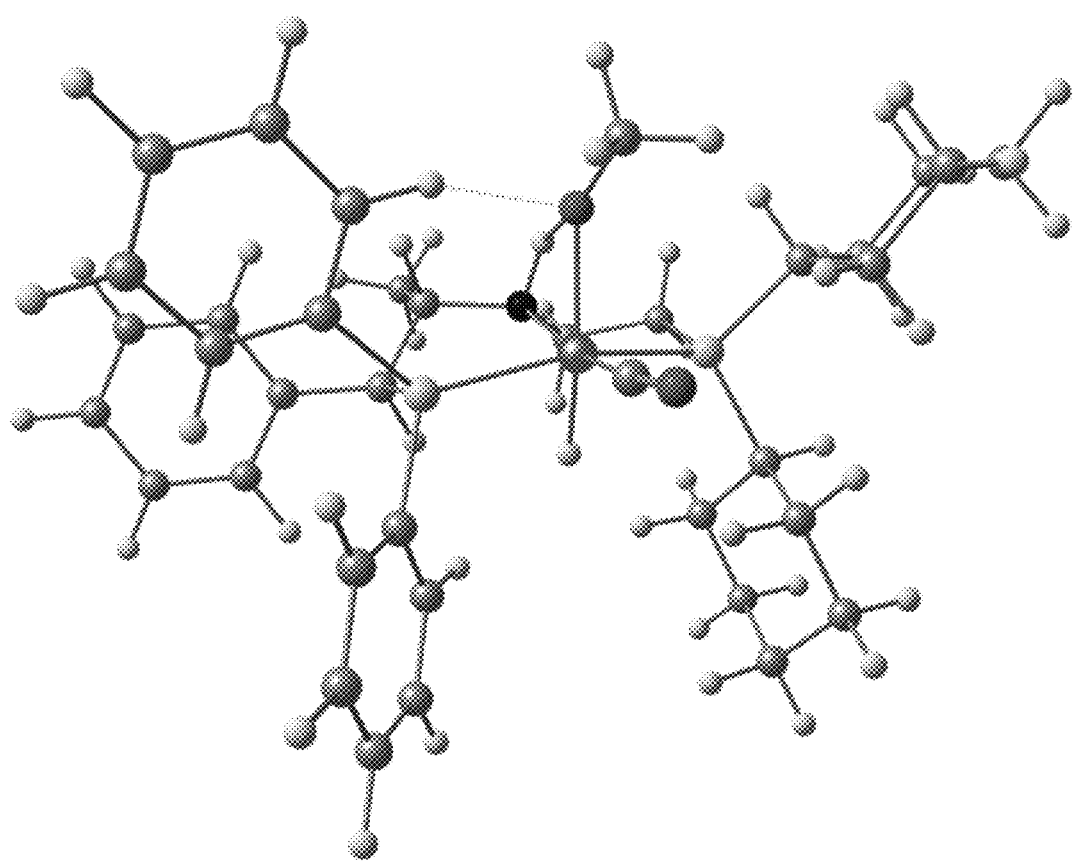
Figure 12B:
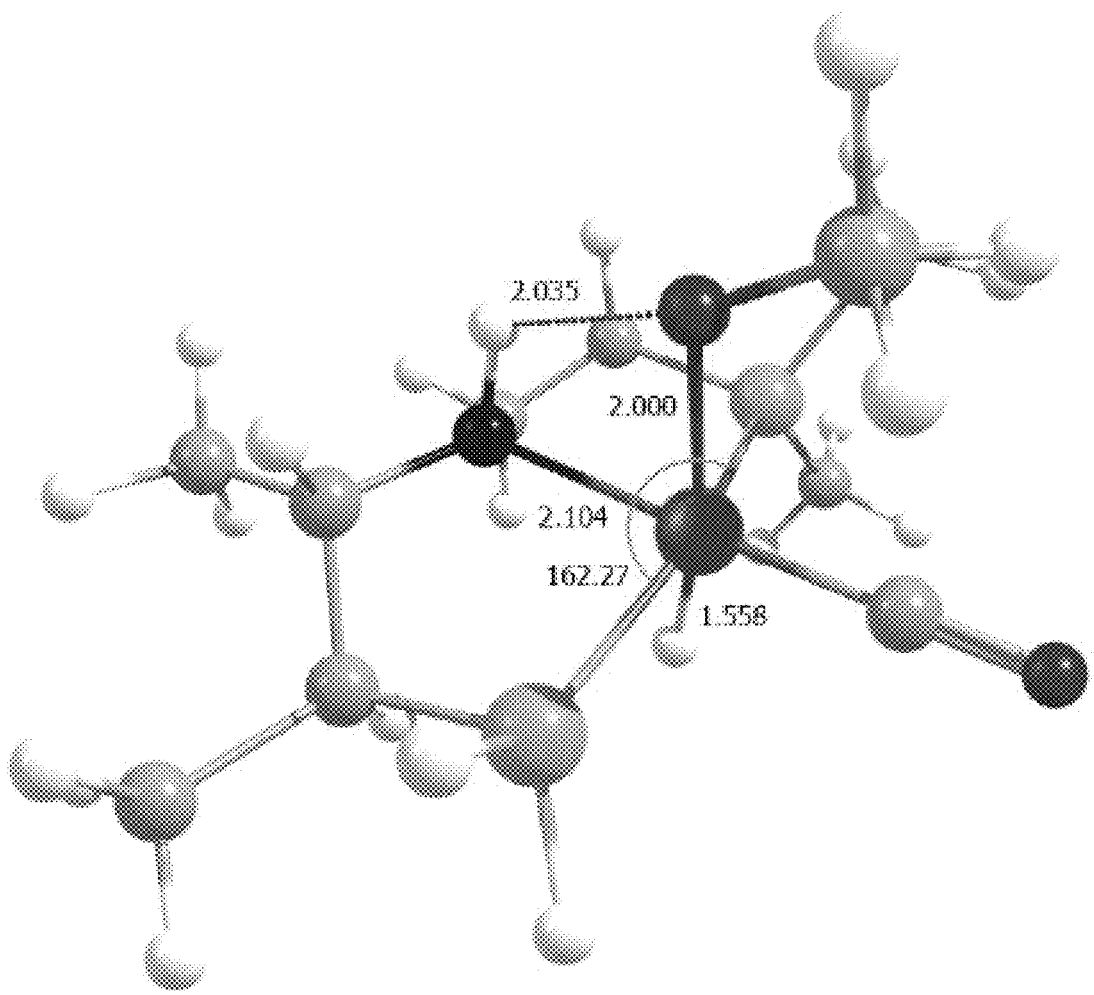
Figure 13:
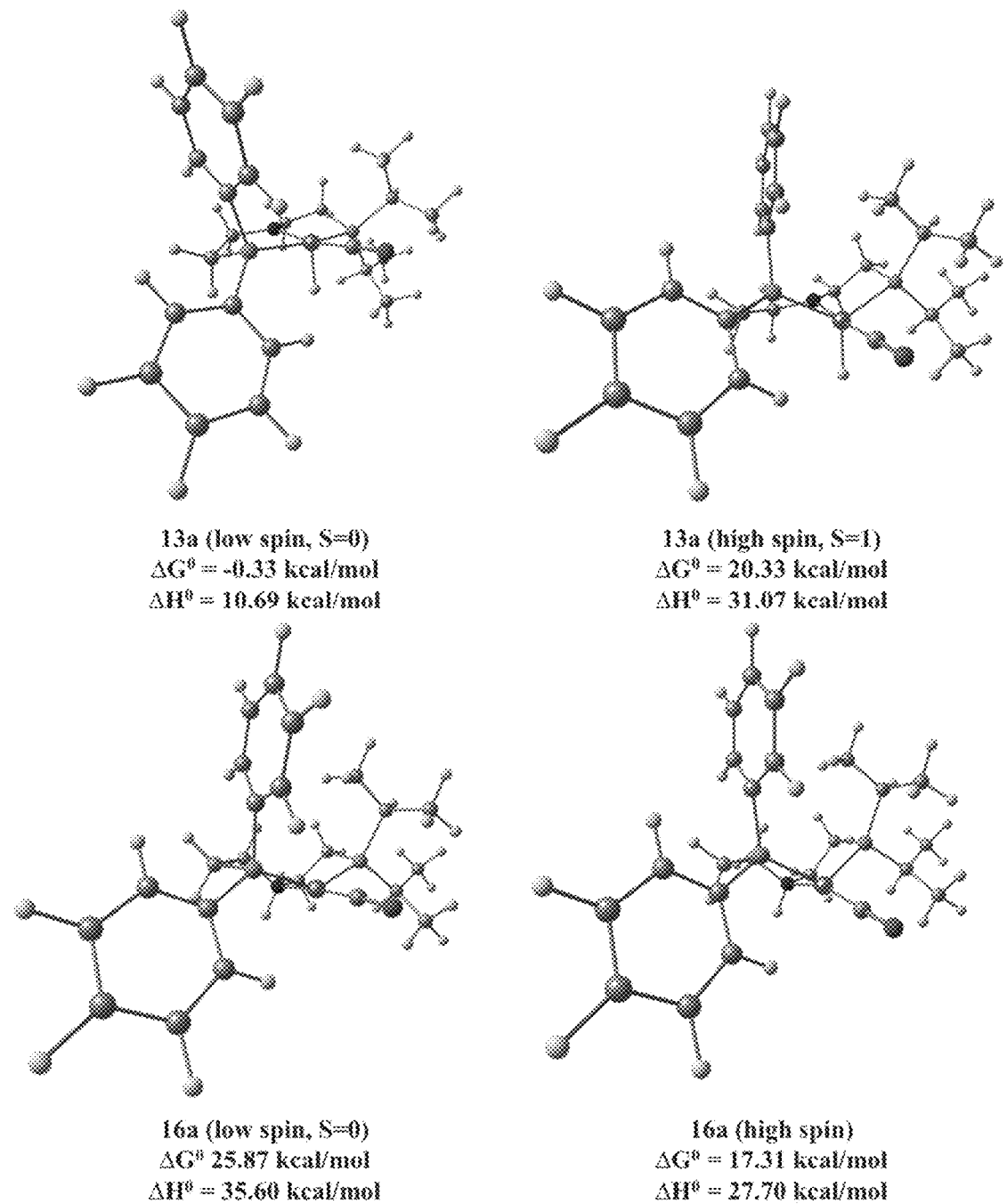
Figure 14:
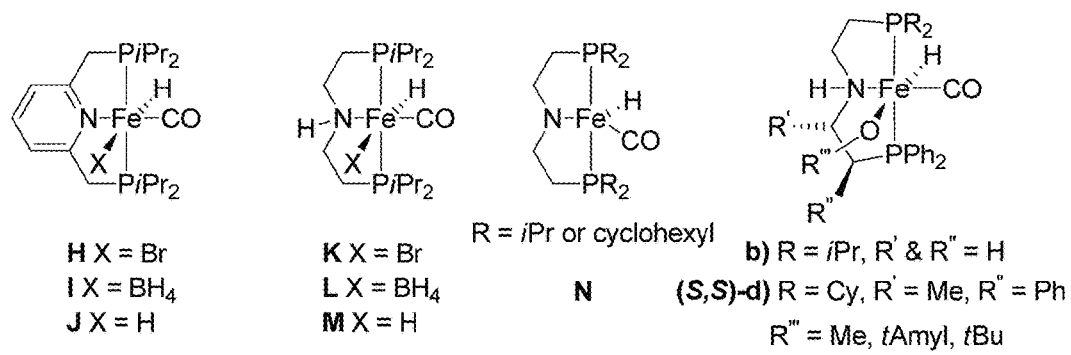
Figure 15:
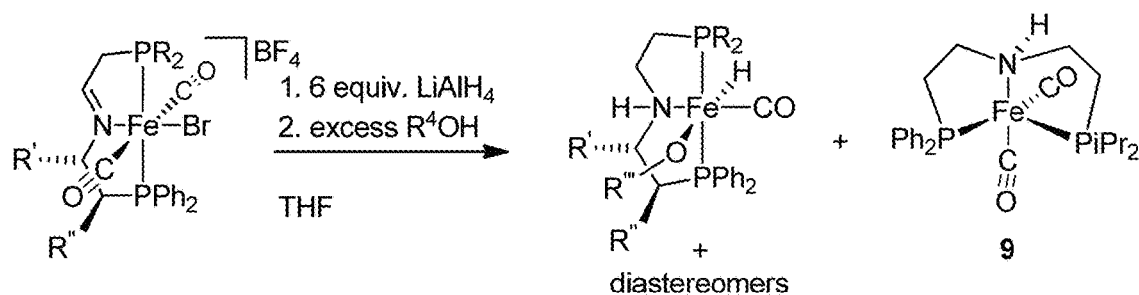
Figure 16:
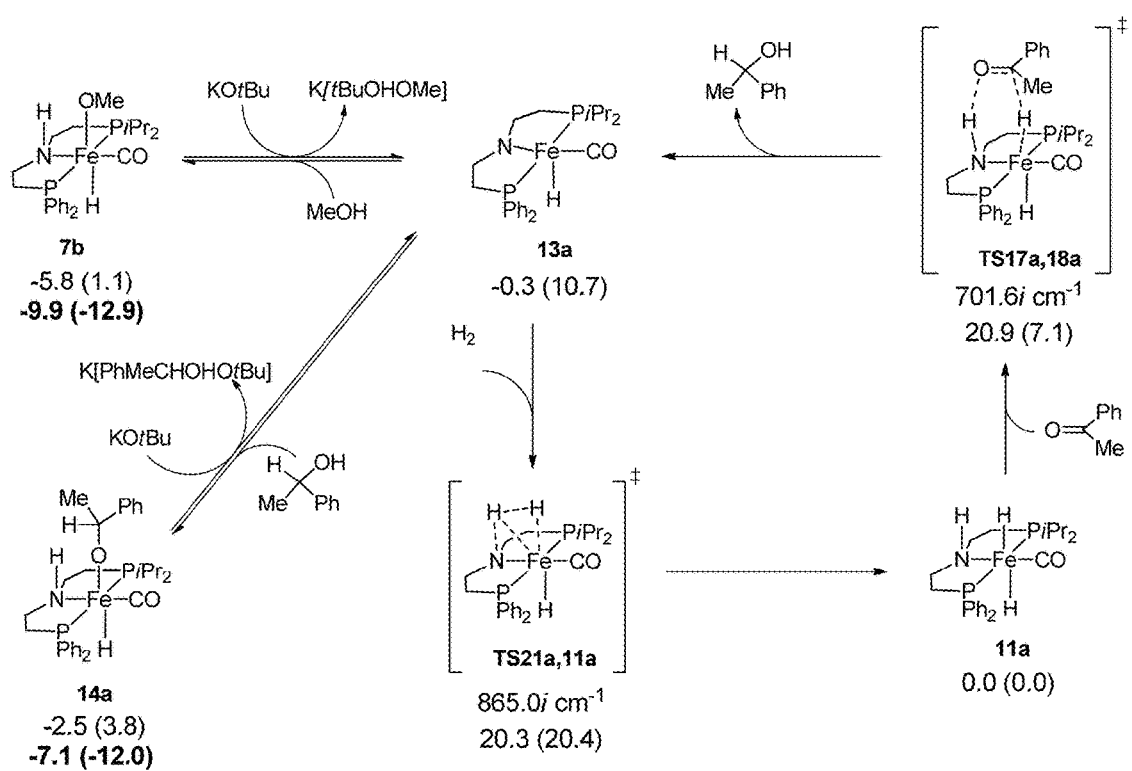
Figure 17:
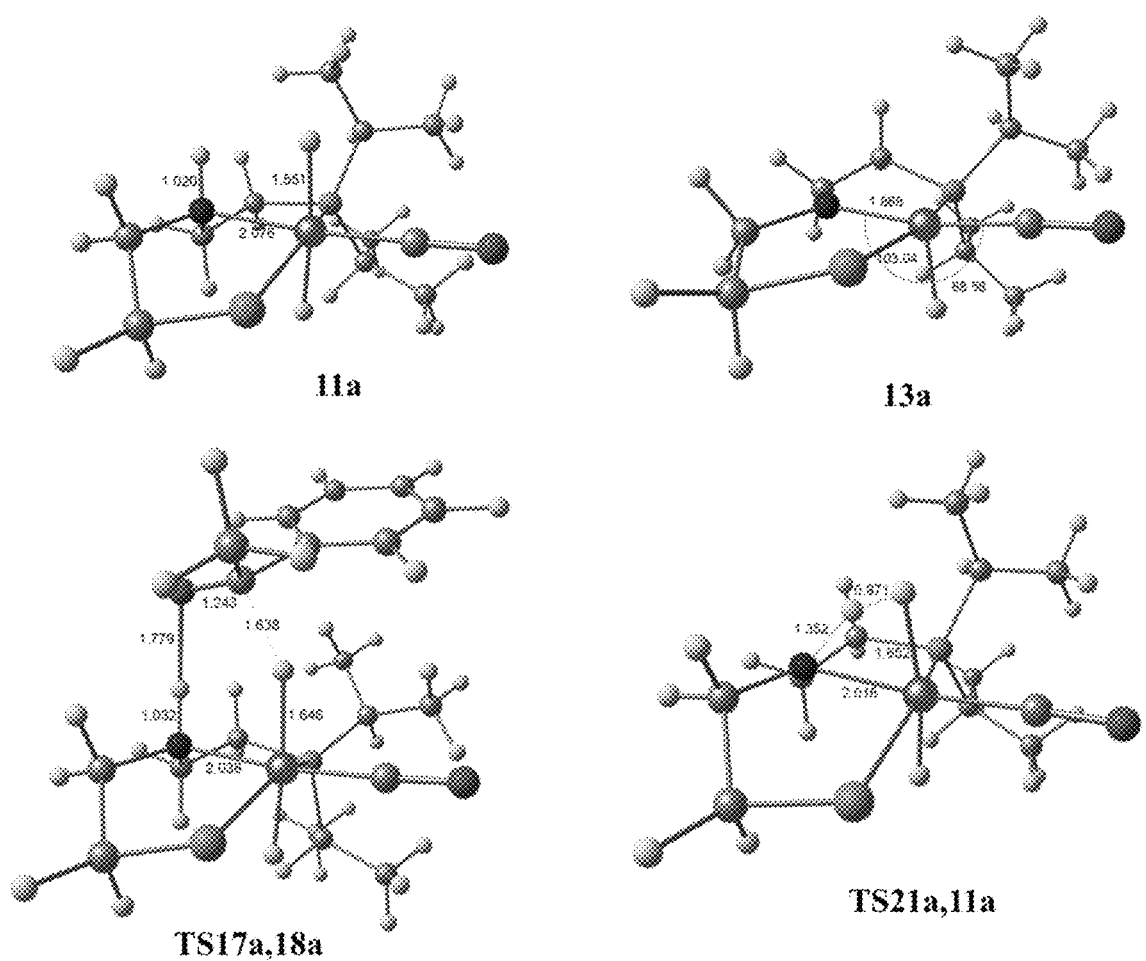
Figure 18:
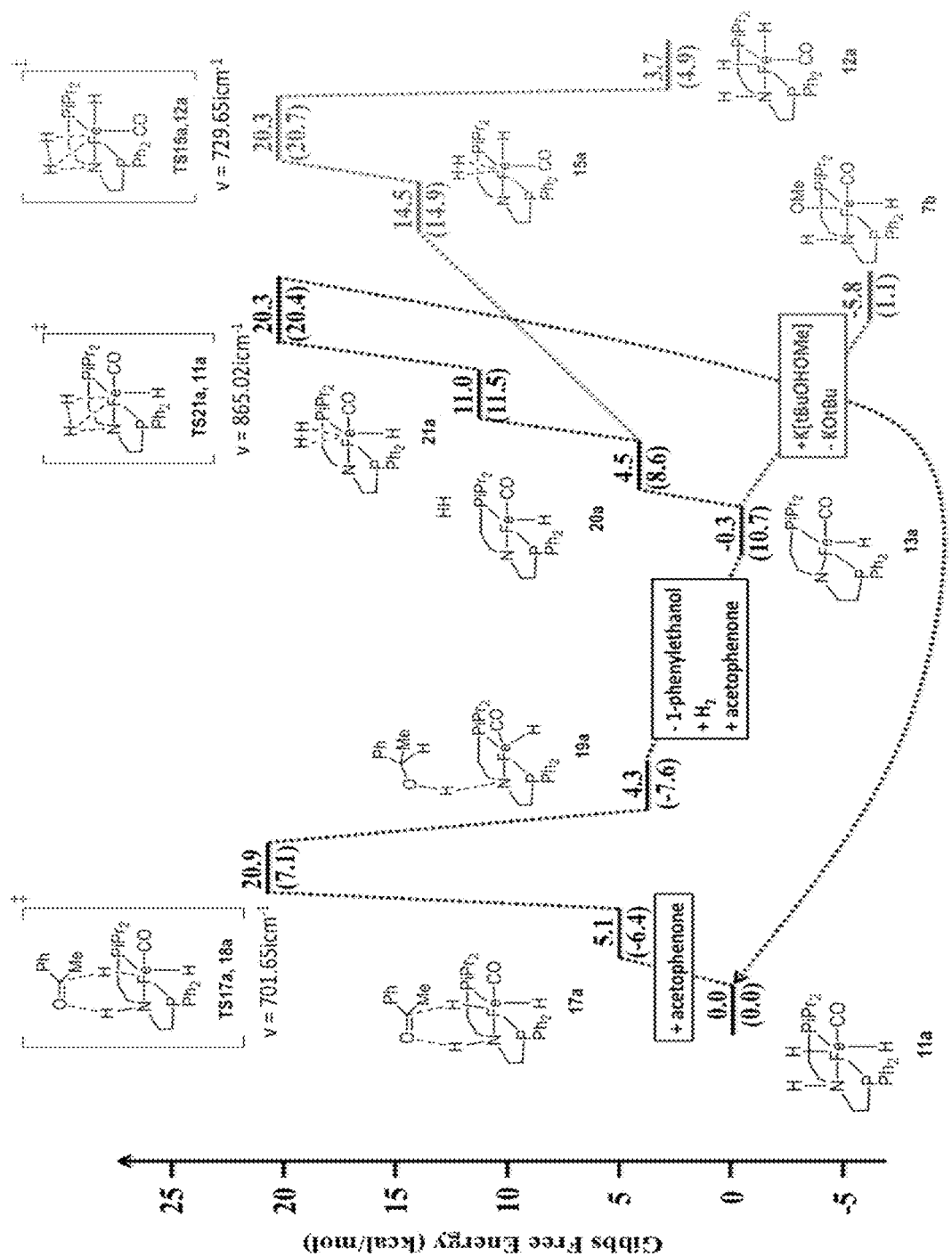
Figure 19:
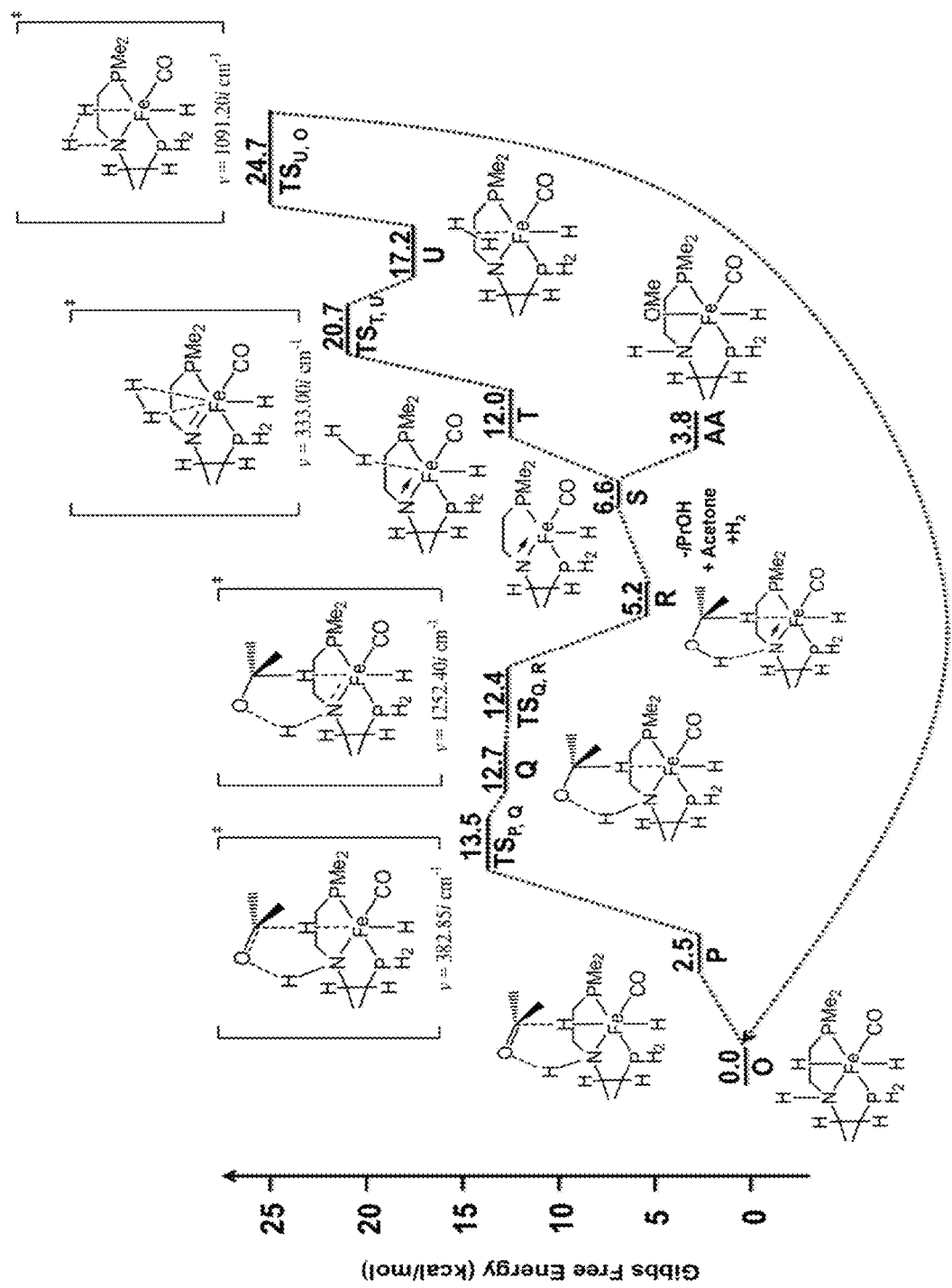
Figure 20:
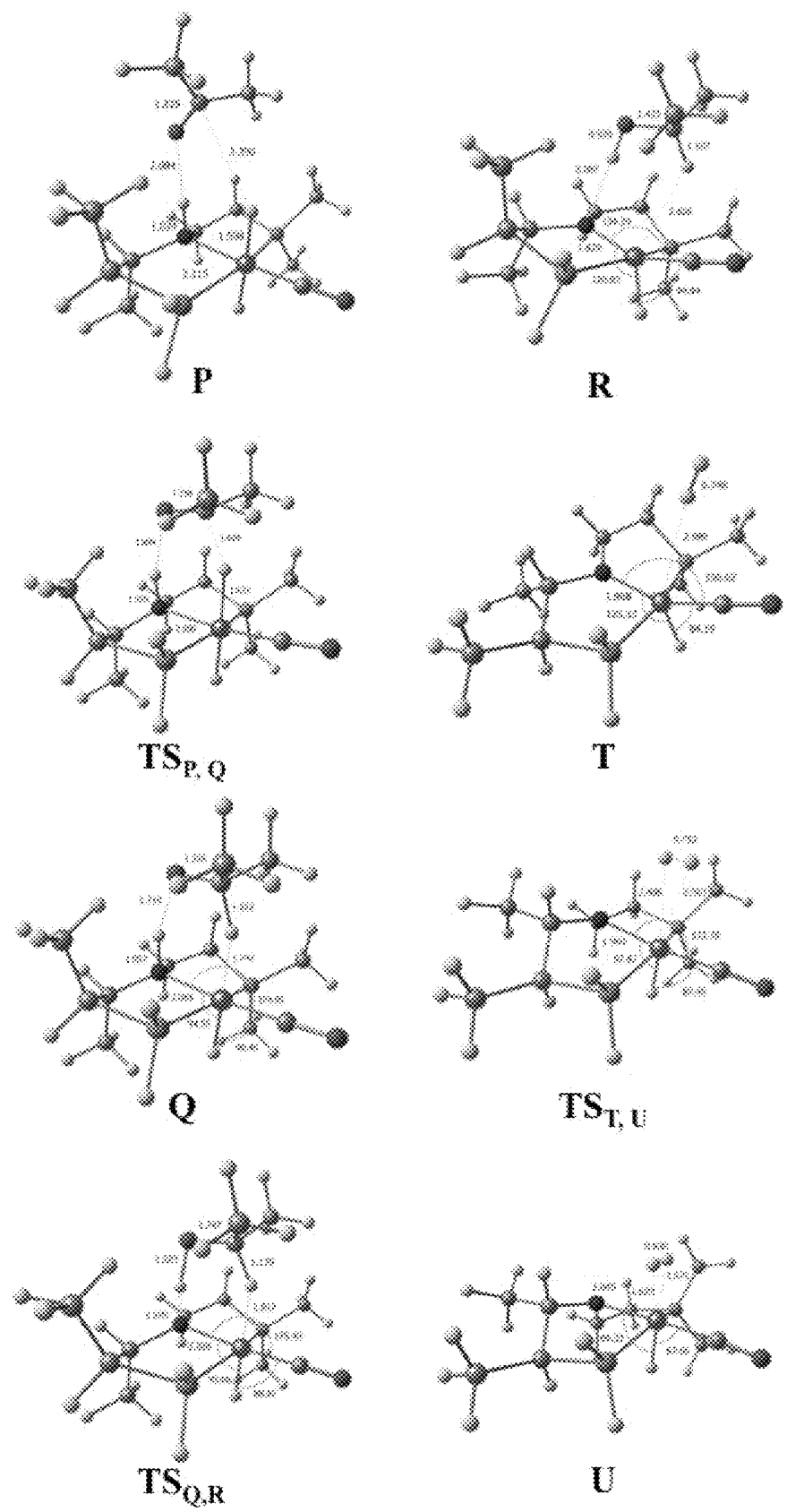
Figure 21:
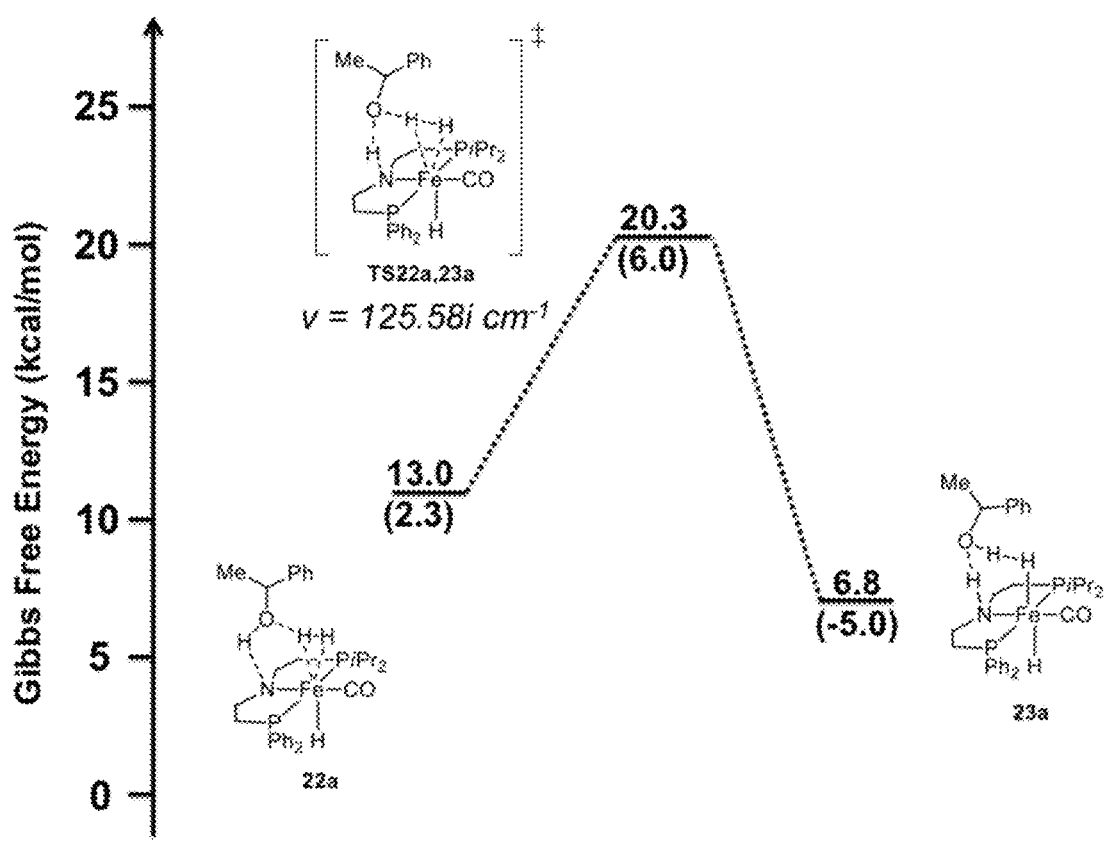
Figure 22:
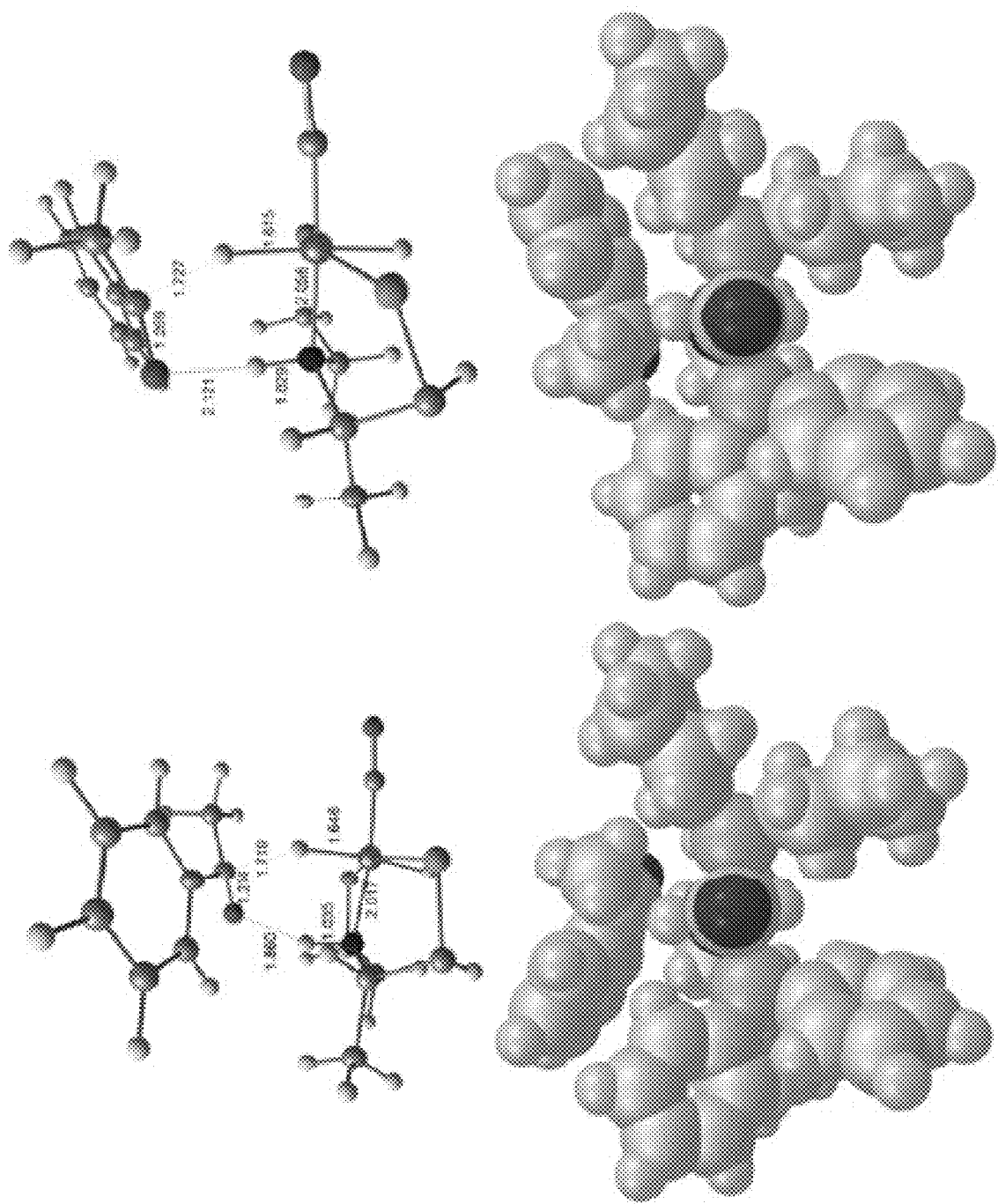
Figure 23:
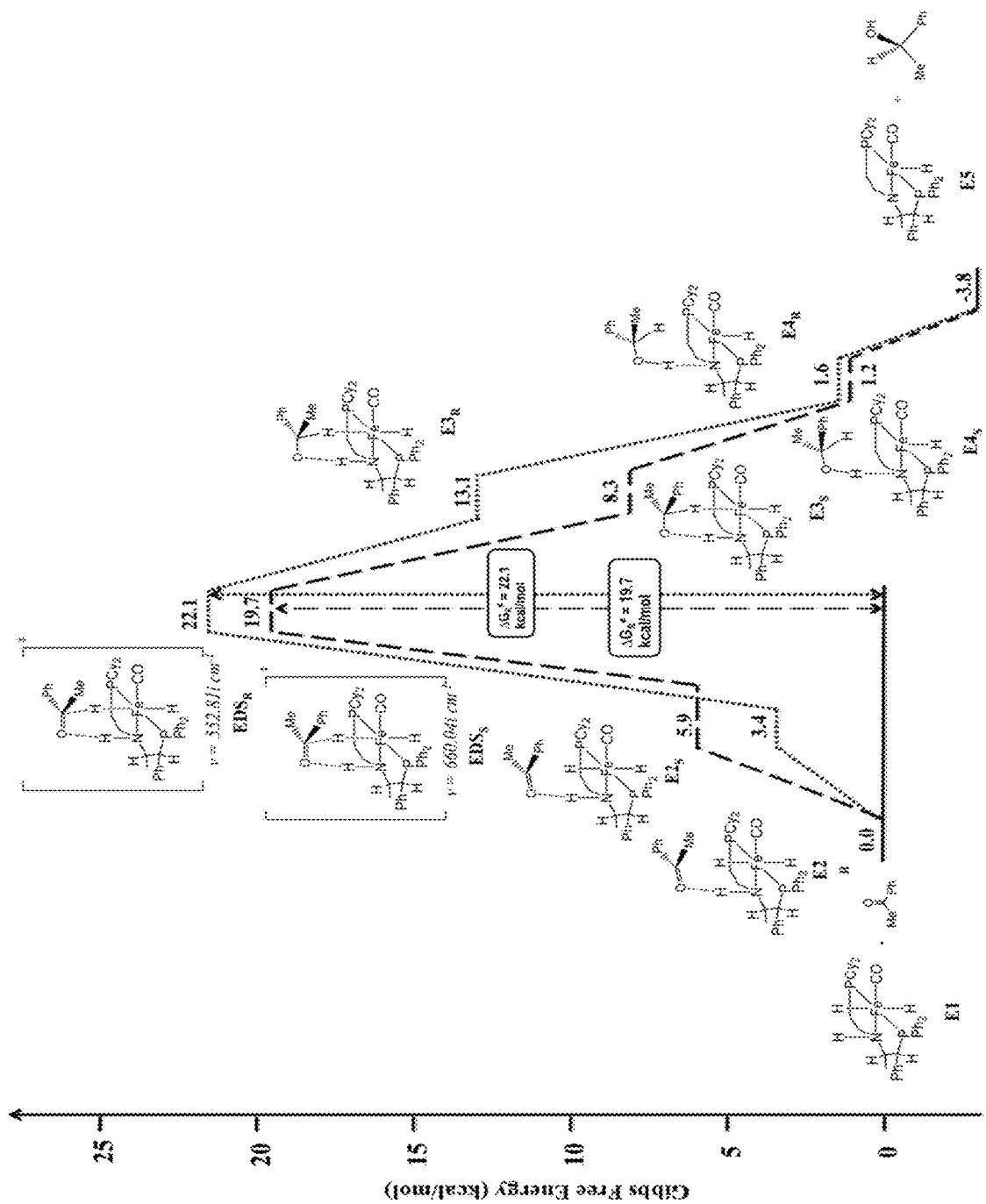

FIG. 3 depicts an ORTEP plot (thermal ellipsoids at 30% probability) of the X-ray crystal structure of trans-Fe(Cy$_2$PCH$_2$CH=NCH$_2$CH$_2$PPh$_2$)(CO)(Br)$_2$, 2a. Hydrogen atoms of Ph and Cy substituents removed for clarity. Selected bond lengths (Å) and angles (deg): Fe(1)-P(1): 2.2680(9); Fe(1)-P(2): 2.2613(9); Fe(1)-N(1): 2.011(2);

Fe(1)-Br(1): 2.4545(5); N(1)-C(2): 1.269(4); N(1)-C(3): 1.479(4): O(1)-C(5): 1.138(4); C(5)-Fe(1)-N(1): 177.6(1); P(2)-Fe(1)-P(1): 167.75(3); Br(1)-Fe(1)-Br(2): 175.12(2);

FIG. 4A depicts ORTEP an plot (thermal ellipsoids at 30% probability) of the X-ray crystal structure of trans-Fe$(Cy_2PCH_2CH=NCH_2CH_2PPh_2)(CO)(Br)_2$, 2a;

FIG. 4B depicts an ORTEP plot (thermal ellipsoids at 30% probability) of the X-ray crystal structures of 4a;

FIG. 4C depicts ORTEP plot (thermal ellipsoids at 30% probability) of the X-ray crystal structures of 4b;

FIG. 4D depicts an ORTEP plot (thermal ellipsoids at 30% probability) of the X-ray crystal structure of cis-[Fe(P—N—P')$(CO)_2(Br)]_2$[FeBr$_4$] (cis-4a). Second cation of cis-[Fe(P—N—P')$(CO)_2(Br)]_2$[FeBr$_4$], FeBr$_4^{2-}$ anion and hydrogen atoms of Ph and Cy substituents removed for clarity. Selected bond lengths (Å) and angles (deg): Fe(1)-Br(1): 2.444(2); Fe(1)-P(1): 2.281(3); Fe(1)-N(1): 2.030(7); Fe(1)-C(5): 1.77(1); Fe(1)-C(6): 1.82(1); O(1)-C(5): 1.13 (1); N(1)-C(3): 1.29(1); N(1)-C(2): 1.40(1); C(5)-Fe(1)-C (6): 90.0(5); P(2)-Fe(1)-P(1): 164.1(1); C(5)-Fe(1)-Br(1): 176.4(3); C(6)-Fe(1)-N(1): 178.9(4);

FIG. 5 depicts a $^1$H NMR spectrum (600 MHz, THF-d8) of hydride-aluminumhydrides of 5a and 6a. Note: a monohydride iron compound was evident at −11.46 ppm ($J_{HP}$=64.1, 71.9 Hz);

FIG. 6 depicts observed and calculated hydride resonances of 6b. Left: hydride resonance at −11.18 ppm ($^2J_{HP}$=28, 38 Hz; line width: 9.00). Right hydride resonance at −11.57 ppm ($^2J_{HP}$=31, 37 Hz; line width: 7.50). (Simulations were obtained from the MestReC NMR processing software (version 4.7.0.0) using a Lorentzian distribution);

FIG. 7 depicts $^1$H and $^1$H{$^{31}$P} NMR spectra (600 MHz, THF-d$_8$) of (S,S)-5d, 6d and 6d (second diastereomer);

FIG. 8 depicts the structure of hydride-aluminumhydride complex FeH$_2$(CO)(PH$_2$CH$_2$CH$_2$N(AlH$_2$)CH$_2$CH$_2$PH$_2$) (compounds 5) calculated using DFT. Atom colours: iron, purple; phosphorus, orange; nitrogen, blue; oxygen, red; aluminum, pink; carbon gray; hydrogen, white. GAUSSIAN09/M06/6-31++G(d,p)/IEF-PCM (THF);

FIG. 9A depicts a structure of hydride-aluminumhydride complex Li[FeH$_2$(CO)(PH$_2$CH$_2$CH$_2$N(AlH$_3$)CH$_2$CH$_2$PH$_2$)] (compounds 6) calculated using DFT. Atom colours: iron, purple; phosphorus, yellow; nitrogen, blue; oxygen, red; aluminum, pink; lithium, magenta; carbon gray; hydrogen, white. GAUSSIAN09/M06/6-31++G(d,p)/IEF-PCM (THF);

FIG. 9B depicts an ORTEP plot of complex 9 (thermal ellipsoids at 30% probability), wherein hydrogen atoms of phenyl and iso-propyl substituents were removed for clarity;

FIG. 10A depicts simplified models of (S,S)-7d, wherein atoms C, H, N, O and P were treated with a 6-31 G basis set;

FIG. 10B depicts relative energies of five possible diastereomers of (S,S)-7d. A sixth high energy diastereomer, D, with hydride trans to CO was not shown. Bond lengths for structure F: Fe—H=1.55, Fe—C=1.69, Fe—O=1.99, Fe—N=2.07, Fe—P (PPh2)=2.23, Fe—P (PCy$_2$)=2.24 Å, O . . . HN1.75 Å. Bond Angles: H—Fe—C=100.9°, H—Fe—P(PCy$_2$)=83.7°, H—Fe—P(PPh$_2$)=77.8°, H—Fe—N=89.6°, O—Fe—C=95.7°, O—Fe—P(PCy$_2$)= 92.4°, O—Fe—P(PPh$_2$)=102.3°, O—Fe—N=73.7°, Fe—N—H=88.5°, Fe—O—H (N—H)=75.2°, N—H—O=119.7°, Fe—O—C=126.5°, Fe—C—O=173.7°, C—Fe—N=169.4°, P(PPh$_2$)-Fe—P(PCy$_2$)=158.9°, H—Fe—O=163.2°;

FIG. 11 depicts $^1$H—$^{31}$P HMBC spectrum (600 MHz, THF-d$_8$) of complexes 5c and 6c;

FIG. 12A depicts Gaussian09 M06/6-31++G(d,p)/(IEF-PCM)SMD(THF) results for most stable simplified model of (S,S)-7d, F, with trans-(H)(OCH$_3$) and OCH$_3$ adjacent to N—H;

FIG. 12B depicts a GAUSSIAN09/M06/6-31++G(d,p)// IEF-PCM+SMD(THF) optimized structure, as well as selected bond lengths (Å) and angles (deg), of most stable isomer F, a simplified structure of (S,S)-7d;

FIG. 13 depicts optimized geometries, Gibbs free energy, and enthalpy for 13a (S=0), 13a (S=1), 16a (S=0) and 16a (S=1), with hydrido amido complex 13a being relatively more stable in its diamagnetic form, and possible Fe(0) product of reductive elimination of hydride and amide, Fe(CO)(P—NH—P') 16a being relatively more stable in a high spin state;

FIG. 14 depicts previously known and herein described iron catalysts with tridentate P—N—P ligands;

FIG. 15 depicts activation of [Fe(PNP')(CO)$_2$Br][BF$_4$] precatalyst with LiAlH$_4$ and alcohol;

FIG. 16 depicts proposed catalytic cycle with resting states and transition states along with relative free energies (and enthalpies in brackets, in kcal/mol) as calculated by DFT; relative energies of 7b and 14a compared to 13a in absence of KOtBu indicated in bold;

FIG. 17 depicts selected geometries for species in catalytic cycle shown in FIG. 16; phenyl groups on one phosphorus were omitted for clarity;

FIG. 18 depicts a free energy profile of a catalytic pathway for complex 11a;

FIG. 19 depicts free energy profile of a catalytic pathway using a simplified structure of (S,S)-11b, model complex A;

FIG. 20 depicts optimized geometries, as well as selected bond lengths (Å) and angles (deg.), of species P, TS$_{P, Q}$ (382.85i cm$^{-1}$), Q, TS$_{Q, R}$ (1252.40i cm$^{-1}$), R, T, TS$_{T, U}$ (333.00i cm$^{-1}$), and U from catalytic cycle shown in FIG. 19, making use of simplified structure of (S,S)-11b where phenyls on phosphorus were replaced with hydrogens, phenyl on the backbone replaced by methyl, and isopropyls on phosphorus replaced with methyls;

FIG. 21 depicts free energy (enthalpy) profile for alcohol-assisted hydrogen splitting in THF;

FIG. 22 depicts enantiodetermining step (EDS) geometries, top: Gaussview model to illustrate relevant bond lengths, with phenyl and cyclohexyl substituents removed for clarity; bottom: complete structures in space-filling style; left: formation of S-isomer EDS$_S$; right: formation of R-isomer EDS$_R$; and FIG. 23 depicts an energy profile for enantiodetermining steps (EDS) and relevant ground states, with S-alcohol formation marked by '---' and R-alcohol formation by '•••••'.

DETAILED DESCRIPTION

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "substituted" refers to the structure having one or more substituents. A substituent is an atom or group of bonded atoms that can be considered to have replaced one or more hydrogen atoms attached to a parent molecular entity. Examples of substituents include aliphatic groups, halogen, arylcarbonyloxy, alkoxycarbonyloxy, aryloxycarbonyloxy, alkoxycarbonyl, aminocarbonyl, alkylthiocarbonyl, alkoxyl, phosphate ester, phosphonato, phosphinato, cyano, tertiary amino, tertiary acylamino, tertiary amide, imino, alkylthio, arylthio, sulfonato, sulfamoyl, tertiary sulfonamido, nitrile, trifluoromethyl, heterocyclyl, aromatic, and heteroaromatic moieties, ether, ester, boron-containing moieties, tertiary phosphines, and silicon-containing moieties. The term "optionally substituted" means unsubstituted or substituted.

As used herein, "alkyl" refers to a linear, branched or cyclic, saturated hydrocarbon group, which can be unsubstituted or is optionally substituted with one or more substituents. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups.

The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, the term "alkenyl" refers to a straight, branched or cyclic hydrocarbon group containing at least one double bond, which can be unsubstituted or optionally substituted with one or more substituents.

As used herein, the term "alkoxy", either alone or in combination with another radical, refers to the radical —O—($C_{1-n}$)alkyl wherein the alkyl group contains one or more carbon atoms, and includes, for example, methoxy, ethoxy, propoxy, 1-methylethoxy, butoxy, cyclohexyloxy, and 1,1-dimethylethoxy. "Alkoxide" refers to the radical —O—($C_{1-n}$)alkyl bearing a negative charge.

As used herein, "aryl" refers to hydrocarbons derived from benzene or a benzene derivative that are unsaturated aromatic carbocyclic groups of from 6 to 100 carbon atoms, which may or may not be a fused ring system. In some embodiments the number of carbon atoms is from 6 to 50, in other embodiments the number of carbon atoms is from 6 to 25, and in still other embodiments the number of carbon atoms is from 6 to 15. An aryl may have a single ring or multiple rings. The term "aryl" as used herein also includes substituted aryls. Examples include, but are not limited to phenyl, naphthyl, xylene, 1- or 2-phenylethyl, substituted phenyl, substituted naphthyl, substituted xylene, substituted 4-ethylphenyl and the like.

As used herein, the term "aryloxy", either alone or in combination with another radical, refers to the radical —O-aryl, wherein aryl is as defined above.

As used herein, "heteroaryl" refers to an aryl that includes from 1 to 10, in other embodiments 1 to 4, heteroatoms selected from oxygen, nitrogen and sulfur, which can be substituted or unsubstituted. The term "heteroatom" refers to an atom that is not carbon or hydrogen, such as nitrogen, oxygen, sulfur, or phosphorus.

As used herein, "halogen" or "halo" refers to F, Cl, Br or I. The term "halide" refers to a halogen atom bearing a negative charge.

As used herein, a "coordinating atom" refers to an atom having a lone pair of electrons capable of coordinating, or forming a covalent dative bond, with a metal atom.

As used herein, a dashed line in a chemical structure is intended to indicate that a bond may or may not be present. In the case where two adjacent bonds are shown with a dashed line to indicate the presence or absence of a double bond, only one of the bonds can be a double bond. It should also be noted that any carbon as well as heteroatom with a valence level that appears to be unsatisfied as described or shown herein, or as a result of an optional bond being absent, is assumed to have a sufficient number of hydrogen atom(s) to satisfy the valences described or shown.

As used herein, the term "electron withdrawing group" refers to an electronegative group capable of polarizing a bond with a carbon atom. Some examples of electron withdrawing groups are halogens, $CF_3$, nitro, nitrile, carbonyl and substituted carbonyl.

The term "PNP" refers to the atoms in the ligand, in sequence, which coordinate to the metal centre of the catalyst. In the described tridentate ligands, the coordinating atoms are phosphorus-nitrogen-phosphorous, hence P—N—P.

As used herein, the terms "catalyst", "catalyst complex" and "complex" refer to the iron (II) species. These terms are used herein to refer to both the catalyst precursors, as well as the active catalysts. These species can be neutrally charged and can exist without a counterion, or can be positively charged and associated with one or more non-coordinating anions(s) to balance the charge As used herein, the term "non-coordinating counter-ion" refers to a negatively charged ion that associates with a positively charged catalyst; or, a positively charged ion that associates with the negatively charged catalyst, to charge balance the catalyst complex. The non-coordinating anion can be any conjugate base of a strong acid, and the non-coordinating cation can be an alkali metal.

As used herein, the term "ligand", abbreviated L, refers to a chemical species that coordinates with the iron centre of the catalyst. The ligand is a Lewis base that can be, for example: a carbon donor such as carbon monoxide, carbene, cyanide or isocyanide (isonitrile); a nitrogen donor, such as nitrosyl, amine, imine, amide, N-heterocycles, nitriles, dinitrogen, or hydrazine; a phosphorous donor, such as phosphines or phosphites; a boron donor, such as boryl; a hydrogen donor, such as dihydrogen, hydride, borohydride, aluminum hydride or other hydride complexes; silane; a silicon donor, such as, silyl; an oxygen donor, such as alcohols, alkoxides, ethers, esters, amides, carboxylates, carboxylic acids, phosphine oxides, sulfoxides or sulfones; a sulfur donor, such as thiols, sulfoxides, thiophenes or sulphides, a halide such as chloride, bromide, or iodide.

As used herein, the term "template synthesis" is method for synthesizing a ligand that is formed from precursor parts that coordinate to a metal ion at geometrically defined positions, such as octahedral or square planar, and bond together. The metal ion acts as a template for the formation of this ligand. Given the same reaction conditions, but in the absence of the metal template, the precursor parts usually do not react, or do react but form a mixture of products, none of which have the structure of the ligand. The term "template ligand" refers to a ligand synthesized via a "template synthesis".

As used herein, the term "hydrogenation" refers to the movement, mediated by a catalyst, of gaseous dihydrogen to a molecule with an unsaturated group, such as a carbonyl or imine.

As used herein, the term "asymmetric hydrogenation" refers to a hydrogenation of a prochiral molecule, such as a ketone, or imine, to produce an enantioenriched product, such as an alcohol or amine, catalyzed by an enantiomeric or enantiopure metal complex.

Overview

Described and disclosed herein are iron(II) complexes with PNP ligands, which are useful as catalytic materials for hydrogenation, and/or asymmetric hydrogenation of aldehydes, ketones, and/or imines.

The asymmetric hydrogenation method described herein, which produces a specific enantiomer, enables a more economical, more efficient, safer, and greener chemical pathway to generate compounds that are enriched in a required enantiomer.

Conventional hydrogenation and asymmetric hydrogenation catalysts utilize platinum group metals (PGM) such as Ru, Os, Rh, Ir, Pd, and/or Pt [De Vries et al., "Handbook of Homogeneous Hydrogenation" Wiley-VCH, volumes 1-3, 2007]. PGMs are expensive and, consequently, add to the cost of the final product. In addition, they are in limited supply and not always readily available. By contrast, iron is relatively inexpensive, abundant, and biocompatible. The iron(II) catalyst systems, containing tridentate diphosphine PNP ligands, described herein display good activity in hydrogenations, with good activity and enantioselectivity in asymmetric hydrogenations, of aldehydes, ketones and/or imines.

Complexes

Described herein are catalysts useful for hydrogenation and/or asymmetric hydrogenation. Specifically, the described catalysts are iron (II) complexes containing tridentate diphosphine (PNP) ligands.

Complexes as described herein have the general structure of formula (I)

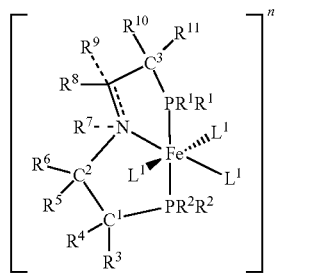

(I)

wherein:
a dashed line indicates that a bond may or may not be present;
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;
$R^7$ is absent, H, $AlH_3$, or $AlH_5$;
each $L^1$ is independently H, $BH_4$, $AlH_4$, a halide, CO, an N-heterocyclic carbene, $OR^{12}$, or $NCR^{13}$, wherein $R^{12}$ and $R^{13}$ are independently $C_1$-$C_{10}$ alkyl, $C_2$-$C_{10}$ alkenyl, aryl, heteroaryl, or $C_3$-$C_{10}$ cycloalkyl, each of which may be substituted; or, one of $L^1$ may be absent;
when $R^7$ is $AlH_3$ or $AlH_5$, at least one of the H may bridge with Fe to form a cycle together with the atoms to which they are attached;
n is 0, +1, or −1, wherein, when n is +1, the complex further comprises at least one non-coordinating anion, Y; and, when n is −1, the complex further comprises at least one non-coordinating cation, Z; such that the total charge of the complex is 0;
with the proviso that, when the nitrogen is singly bound to the carbon attached to $R^9$, each of $R^3$ to $R^{11}$ are H, one $L^1$ is CO, and the other two $L^1$'s are Br, or Br and H, or $BH_4$ and H, then the $R^1$ and $R^2$ substituents cannot all be isopropyl; and
with the proviso that, when the nitrogen is singly bound to the carbon attached to $R^9$, each of $R^3$ to $R^{11}$ are H, $R^7$ is absent, one $L^1$ is absent, one of $L^1$ is CO, and one of $L^1$ is H, then the $R^1$ and $R^2$ substituents cannot all be isopropyl.

When the complex of formula (I) has $L^1$=H and $OR^{12}$, the complex will have the structure of formula (Ia):

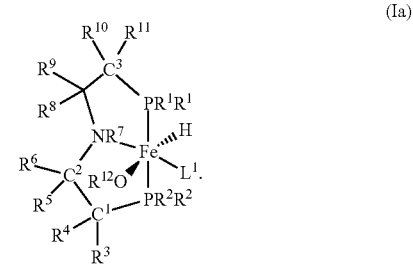

(Ia)

When the complex of formula (I) has $R^7$=$AlH_3$ or $AlH_5$, the complex will have the structure of formula (Ib) or (Ic):

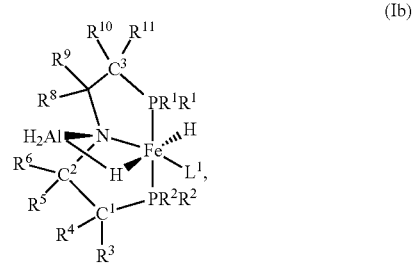

(Ib)

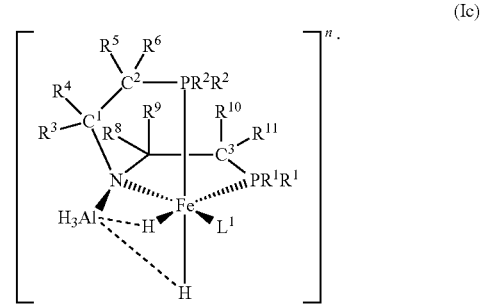

(Ic)

When the complex of formula (I) has an imine at N and one $L^1$=a halide (X), the complex will have the structure of formula (Id):

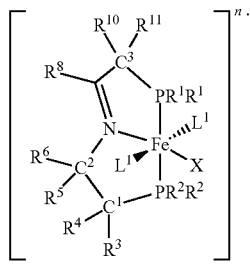
(Id)

When the complex of formula (I) has an imine at N and two $L^1$=a halide (X), the complex will have the structure of formula (Ie) or (If):

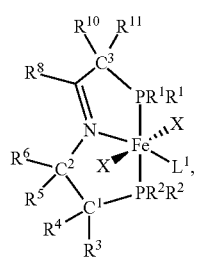
(Ie)

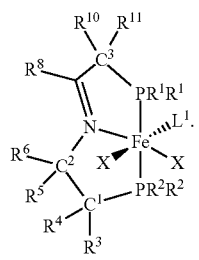
(If)

When the complex of formula (I) has two $L^1$=H, the complex will have the structure of formula (Ih) or (Ig):

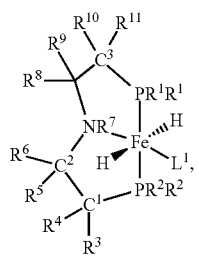
(Ig)

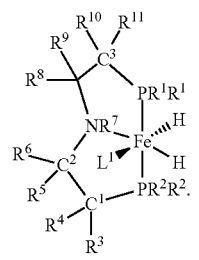
(Ih)

When the complex of formula (I) has one $L^1$=absent, and one $L^1$=H, the complex will have the structure of formula (Ii):

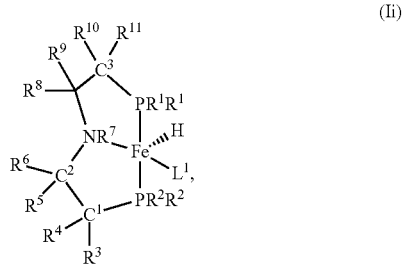
(Ii)

The complexes described herein can optionally comprise at least one non-coordinating anion or cation. The non-coordinating anion can be any conjugate case of a strong acid. Non-limiting examples of anions include halides, $BF_4^-$, $PF_6^-$, $SbF_6^-$, $NO_3^-$, $CF_3COO^-$, $R^{14}SO_3^-$, $CF_3SO_3^-$, $C_6H_5SO_3^-$, p-$CH_3C_6H_4SO_3^-$, phosphates, TRISPHAT(Δ- or Λ-$P(OC_6Cl_4O)_3^-$), carboranes, $B(R^{14})_4^-$ or $Al(R^{14})_4^-$, each of which may be substituted, wherein each $R^{14}$ is independently an optionally substituted $C_1$-$C_6$ alkyl, aryl, heteroaryl, $C_6H_3(CF_3)_2$ and $C_6F_5$, halogen, pseudohalogen, $C_1$-$C_8$ alkoxide, or aryloxide. In one embodiment, Y is $BF_4^-$. The non-coordinating cation can be any alkali metal ion. Non-limiting examples of cations include $K^+$, $Na^+$, or $Li^+$.

The complexes described herein can optionally comprise chiral carbons, wherein the complexes are enantiomerically enriched, or racemates. Non-limiting examples of chiral complexes are as follows:

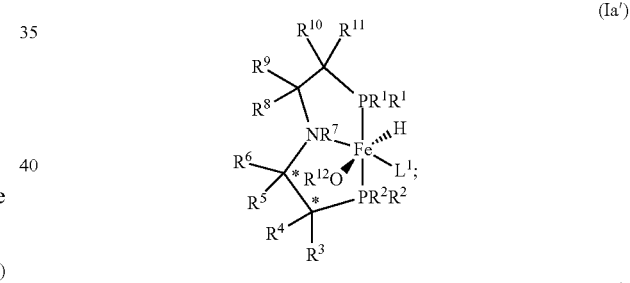
(Ia')

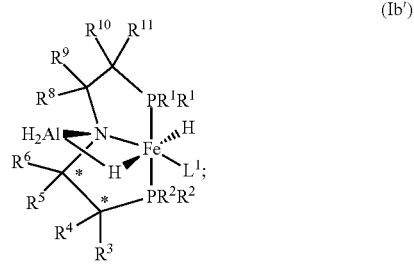
(Ib')

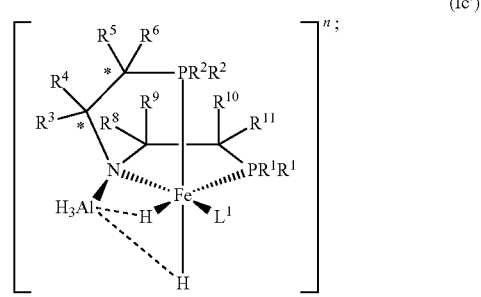
(Ic')

-continued

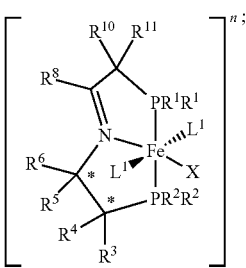
(Id')

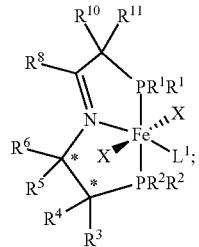
(Ie')

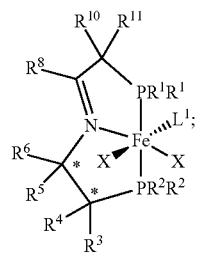
(If')

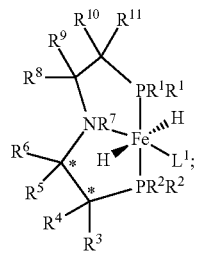
(Ig')

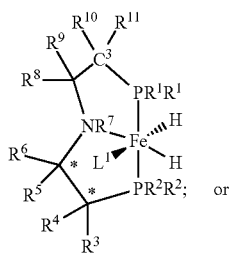
(Ih')

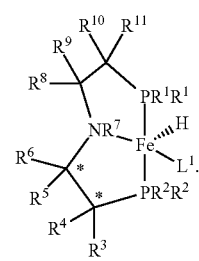
(I')

Synthesis of Iron Complexes

Previously reported multi-component template syntheses of iron(II) complexes (patent application U.S. Ser. No. 12/609,955 and PCT/CA2013-050405, each of which is incorporated herein by reference in its entirety) were modified and implemented in the synthesis of the herein described complexes.

Consequently, there is provided herein a process for preparing any one of the complexes (I), and (Ia)-(If) herein described, the process comprising reacting a phosphine-aldehyde precursor of formula (II)

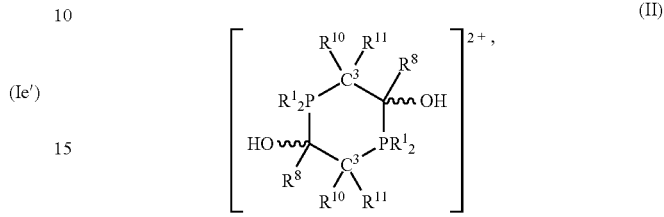
(II)

wherein $R^1$, $R^8$, $R^{10}$, and $R^{11}$ are as defined above, with a phosphine-amine of formula (III)

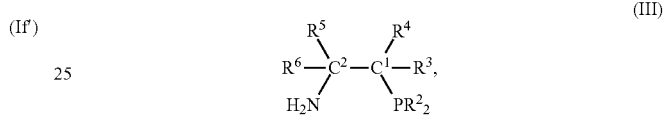
(III)

wherein $R^2$, $R^3$, $R^4$, $R^5$, and $R^6$ are as defined above,
in the presence of
an iron(II) compound,
a CO atmosphere, and
a strong base,
to form a complex of formula (Ie), or to form a mixture of complexes of formula (Ie) and formula (If),

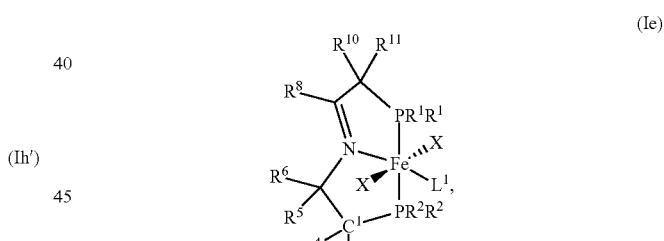
(Ie)

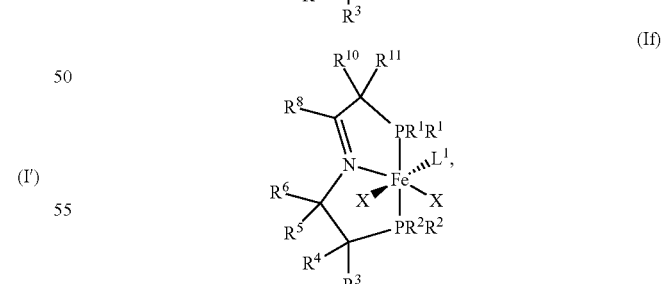
(If)

wherein X is a halide, and
$L^1$ is CO;
the complex of formula (Ie), or the mixture of complexes of formula (Ie) and formula (If), is further reacted in the presence of
a silver salt, and
a CO atmosphere, to form a complex of formula (1d)

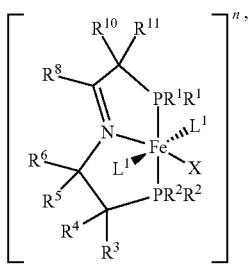
(Id)

which is further reacted in the presence of a reducing agent to form the complex of formula (Ib) and/or (Ic)

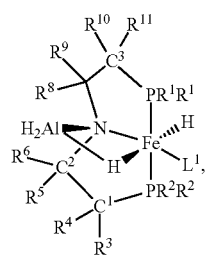
(Ib)

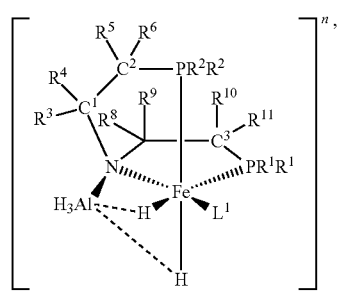
(Ic)

wherein $R^9$ is H,
which are further reacted with an excess of a primary, secondary, or tertiary alcohol, to form the complex of formula (Ia)

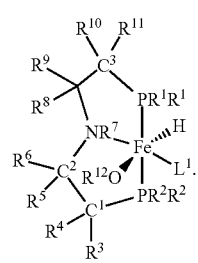
(Ia)

The process described herein can optionally involve phosphine-amines of formula (III), and/or phosphine-aldehyde precursors of formula (II) that are chiral, wherein each precursor is optionally enantiomerically enriched, or a racemate.

In one embodiment of the process described herein, the iron source is an iron(II) salt such as $FeBr_2$ or $FeCl_2$; or, an iron(II) complex such as $Fe(CO)_4Br_2$, which is additionally reacted in the presence of UV radiation to aid in formation of the complex of formula (Ie); or, to form a mixture of complexes of formula (Ie) and formula (If). In other embodiments, the iron source can be a Fe(II) salt with halide(s) or pseudo halide(s) that are soluble in common organic solvents, with the halide or pseudo halide being capable of precipitating as an insoluble silver salt or sodium salt in preparation of complexes (I) (e.g. complexes 4a-4d below).

In one embodiment, the silver salt is $AgBF_4$, the reducing agent is $LiAlH_4$ or $NaAlH_4$, and the alcohol is MeOH, EtOH, tBuOH, or $^t$AmylOH.

There is also provided herein a process for preparing any one of the complexes (Ig)-(Ig) herein described, the process comprising reacting a complex of formula (Ia)

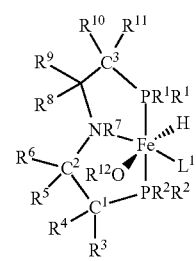
(Ia)

wherein $R^1$, $R^2$, $R^3$, $R^4$, $R^5$, $R^6$, $R^7$, $R^8$, $R^{10}$, $R^{11}$, $R^{12}$ and $L^1$ are as defined above,
in the presence of
a base, and
a $H_2$ atmosphere
to form a complex of formula (Ig) and/or a complex of formula (Ih),

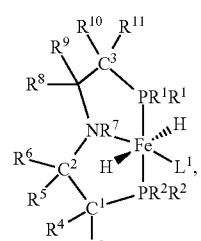
(Ig)

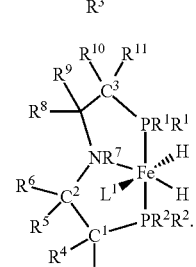
(Ih)

In one embodiment of the process described herein, carbon $C^1$, $C^2$ or $C^3$, or any combination thereof, of complexes of formula (Ia), (Ig), or (Ih) is chiral, and the complex is enantiomerically enriched, or a racemate. In another embodiment, the base is KOtBu, NaOtBu, Ph-CH(OK)CH$_3$, or NaOMe.

Catalytic Hydrogenation Methods

The herein described iron(II) complexes are useful for catalytic hydrogenation of unsaturated chemical bonds such as, for example, imines and carbonyl groups. These complexes are also useful for the effective asymmetric hydrogenation of substrates, such as ketones and imines to give enantiomeric or enantiomerically enriched products, such as alcohols and amines. In one embodiment, the activated iron(II) complexes have been shown to be capable of transferring gaseous $H_2$ to a carbonyl or imine polar bond.

As such, described herein is a use of any one of the herein described complexes, prepared by the herein described process, as a hydrogenation pre-catalyst or hydrogenation catalyst to hydrogenate a substrate, such as a ketone, aldehyde, or imine.

In one embodiment of this use, the complexes are chiral and the hydrogenation is an asymmetric hydrogenation.

The herein described catalysts can be utilized for preparing alcohols. Imine groups can similarly be hydrogenated or asymmetrically hydrogenated to provide amines. It is understood that when an enantiopure catalyst is used the products of these organic reactions can be enantioenriched when a reactant is prochiral.

The products of the herein described hydrogenation reactions may be useful in subsequent reactions to prepare commercial end products, such as, for example, pharmaceuticals, agrichemicals, cosmetics and nutriceuticals.

As such, described herein is a method for hydrogenation of a substrate comprising contacting the substrate with a hydrogen source in the presence of any one of the herein described complexes, under conditions suitable for hydrogenation.

In one embodiment of this method, the substrate is a ketone, aldehyde, or imine. In another embodiment, the hydrogen source is hydrogen gas at a pressure >0 atm and less than <70 atm.

To gain a better understanding of the invention described herein, the following examples are set forth. It should be understood that these examples are for illustrative purposes only. Therefore, they should not limit the scope of this invention in any way.

EXAMPLES

General Methods

All procedures and manipulations involving air-sensitive materials were performed under an argon or nitrogen atmosphere using Schlenk techniques or a glove-box with $N_2(g)$. Solvents were degassed and dried using standard procedures prior to all manipulations and reactions. Deuterated solvents were purchased from Cambridge Isotope Laboratories or Sigma-Aldrich, degassed and dried over activated molecular sieves prior to use. All liquid ketone substrates were vacuum distilled, degassed and stored over activated molecular sieves. Phosphonium dimers 1a-c [see FIG. 2; Lagaditis, P. O.; Mikhailine, A. A.; Lough, A. J.; Morris, R. H. *Inorg. Chem.* 2010, 49, 1094-1102; Mikhailine, A. A.; Lagaditis, P. O.; Sues, P. E.; Lough, A. J.; Morris, R. H. *J. Organomet. Chem.* 2010, 695, 1824-1830], and $Fe(CO)_4(Br)_2$ [Turrell, P. J.; Wright, J. A.; Peck, J. N. T.; Oganesyan, V. S.; Pickett, C. J. *Angew. Chem. Int. Ed.* 2010, 49, 7508-7511] were synthesized according to literature procedures. 2-(diphenylphosphino) ethylamine was donated by Digital Specialty Chemicals. All other reagents were purchased from Sigma-Aldrich or Strem Chemicals and utilized without further purifications. NMR spectra were recorded at ambient temperature and pressure using Varian Gemini [$^1$H (400, 600 MHz), $^{13}$C{$^1$H} (100, 150 MHz), $^{31}$P{$^1$H} (161, 242 MHz), $^{19}$F{$^1$H} (356 MHz)]. $^{31}$P chemical shifts were measured relative to 85% $H_3PO_4$ as an external reference. $^{19}$F chemical shifts were referenced relative to $CFCl_3$. In the synthesis of 2a and b (see FIG. 2), photolysis was performed using a 450 W mercury vapor lamp (model: Hanovia UV Medium Pressure 450 W Immersion Lamp). The elemental analyses were performed on a Perkin-Elmer 2400 CHN elemental analyzer. Some complexes gave unsatisfactory carbon analyses but acceptable hydrogen and nitrogen content because of a combustion problem due to the tetrafluoroborate anion [Marcó, A.; Compano, R.; Rubio, R.; Casals, I. *Microchimica Acta* 2003, 142, 13-19].

Example 1

Template Synthesis of Iron(II) Complexes

Experimental trans-Fe(Ph$_2$PCH$_2$CH$_2$NCHCH$_2$PCy$_2$)(CO)(Br)$_2$, 2a: A vial was charged with 1a (80 mg, 0.125 mmol) and KOtBu (28 mg, 0.249 mmol) and 25 mL benzene, forming a slurry. The slurry was allowed to stir for 10 min by which time it turned cloudy and was then filtered into a Schlenk flask. To this solution, 2-(diphenylphosphino)ethylamine (57 mg, 0.249 mmol) was added, followed by Fe(CO)$_4$(Br)$_2$ (81 mg, 0.249 mmol). The mixture immediately evolved gas in addition to turning orange in color. The flask was immediately exposed to UV light and was allowed to stir for 6 hours or until the solution turned red-purple. The flask was removed from the UV source and filtered through a pad Celite to remove all precipitates. The solvent was concentrated and pentane (10 mL) was added to cause precipitation of a pale pink solid. The solid was washed with pentane (5 mL) and dried under vacuum. Yield: 35% (60 mg). $^1$H NMR (400 MHz, C$_6$D$_6$) δ: 1.18-1.95 (m, HCy), 2.47 (m, 2H, CH$_2$PCy$_2$), 2.66 (m, 2H, CHCy), 2.79 (m, 2H, CH$_2$PPh$_2$), 4.11 (m, 2H, CH$_2$N), 6.94 (m, 2H, HPh), 7.05 (m, 4H, HPh), 7.91 (m, 5H, HPh, CHN). $^{13}$C {$^1$H} NMR (100 MHz, C$_6$D$_6$) δ: 26.5 (CCy), 27.9 (CCy), 28.7 (CH$_2$PPh$_2$), 29.9 (CCy), 30.6 (CH$_2$PCy$_2$), 36.4 (CCy), 62.6 (CH$_2$N), 129.5 (CPh), 133.1 (CPh), 135.7 (CPh), 146.6 (CPh), 173.3 (CHN), 227.8 (br t, J$_{PC}$=24.0 Hz, CO). $^{31}$P {$^1$H} NMR (161 MHz, C$_6$D$_6$) δ: 68.2 (d, J$_{PP}$=174 Hz), 71.2 (d, J$_{PP}$=174 Hz) ppm. IR (KBr) 1945 cm$^{-1}$ (ν$_{C≡O}$). Anal. Calcd for C$_{29}$H$_{39}$NOP$_2$FeBr$_2$: C, 50.10; H, 5.65; N, 2.01. Found: C, 49.52; H, 5.88; N, 1.75. MS (ESI, methanol/water; m/z$^+$): 586.1 [C$_{28}$H$_{39}$NP$_2$FeBr]$^+$. FIG. 4A depicts An ORTEP plot (thermal ellipsoids at 30% probability) of the X-ray crystal structure of trans-Fe(Cy$_2$PCH$_2$CH═NCH$_2$CH$_2$PPh$_2$)(CO)(Br)$_2$, 2a, wherein hydrogen atoms of Ph and Cy substituents removed for clarity. Selected bond lengths (Å) and angles (deg): Fe(1)-P(1): 2.2680(9); Fe(1)-P(2): 2.2613(9); Fe(1)-N(1): 2.011(2); Fe(1)-Br(1): 2.4545(5); N(1)-C(2): 1.269(4); N(1)-C(3): 1.479(4); O(1)-C(5): 1.138(4); C(5)-Fe(1)-N(1): 177.6(1); P(2)-Fe(1)-P(1): 167.75(3); Br(1)-Fe(1)-Br(2): 175.12(2).

trans-Fe(Ph$_2$PCH$_2$CH$_2$NCHCH$_2$PiPr$_2$)(CO)(Br)$_2$, 2b: The pale pink solid product was synthesized and isolated using the procedure outlined for trans-[Fe(Ph$_2$PCH$_2$CH$_2$NCHCH$_2$PCy$_2$)(CO)(Br)$_2$]: 1b (80 mg, 0.166 mmol); KOtBu (38 mg, 0.331 mmol); 2-(diphenylphosphino) ethylamine (76 mg, 0.331 mmol); Fe(CO)$_4$(Br)$_2$ (108 mg, 0.331 mmol). Yield: 25% (50 mg). $^1$H NMR (400 MHz, C$_6$D$_6$) δ: 0.90 (dd, J$_{HP}$=7, 14 Hz, 1H, CH(CH$_3$)$_2$), 1.21 (dd, J$_{HP}$=7, 13 Hz, 6H, CH$_3$), 1.44 (dd, J$_{HP}$=7, 13 Hz, 6H, CH$_3$), 1.70 (dd, $J_{HP}$=7, 16 Hz, 1H, CH(CH$_3$)$_2$), 2.74 (m, 2H, CH$_2$PiPr$_2$) 2.77 (m, 2H, CH$_2$PPh$_2$), 4.13 (m, $J_{HP}$=20.6 Hz, 2H, CH$_2$N), 6.93 (m, 4H, HPh), 7.04 (m, 2H, HPh), 7.22 (indirectly determined from $^1$H-$^{13}$C HSQC, CHN), 7.89 (m, 2H, HPh), 7.98 (m, 2H, HPh), 8.45 (m, 1H, HPh). $^{13}$C {$^1$H} NMR (100 MHz, C$_6$D$_6$) δ: 19.35 (CH$_3$), 19.5 (CH(CH$_3$)$_2$), 20.5 (CH$_3$), 25.8 (CH(CH$_3$)$_2$), 28.2 (d, $J_{CP}$=20 Hz, CH$_2$PPh$_2$), 38.0 (d, $J_{CP}$=17 Hz, CH$_2$PiPr$_2$), 61.3 (CH$_2$N), 129.4 (CPh), 131.5 (CPh), 132.8 (CPh), 135.3 (CPh), 171.8 (CHN), 227.9 (t, $J_{CP}$=23.8 Hz, CO). $^{31}$P {$^1$H} NMR (161 MHz, C$_6$D$_6$) δ: 67.4 (d, $J_{PP}$=176 Hz), 79.7 (d, $J_{PP}$=176 Hz) ppm. IR (KBr) 1945 cm$^{-1}$ ($\nu_{C=O}$). Anal. Calcd for C$_{23}$H$_{31}$NOP$_2$FeBr$_2$: C, 44.91; H, 5.08; N, 2.28. Found: C, 43.99; H, 5.12; N, 2.30. MS (ESI, methanol/water; m/z$^+$): 507.2 [C$_{22}$H$_{31}$NP$_2$FeBr]$^+$.

$^{31}$P{$^1$H}NMR Chemical Shifts (ppm) and Coupling Constants (Hz) of Compounds 2 and 3$^a$:

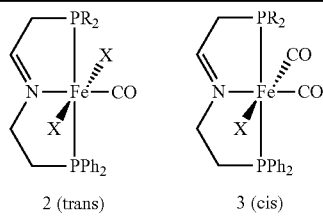

| | 2 (trans) | 3 (cis) |
|---|---|---|
| a | 67.8 and 71.9 | 39.6 and 60.5 |
| R = Cy, X = Br | $^2J_{PP}$ = 175.0 | $^2J_{PP}$ = 201.3 |
| b | 67.36 and 79.9 | 40.5 and 70.5 |
| R = iPr, X = Br | $^2J_{PP}$ = 176.0 | $^2J_{PP}$ = 207.5 |
| c | 70.0 and 74.0 | 42.8 and 49.6 |
| R = Ph, X = Br | $^2J_{PP}$ = 192.0 | $^2J_{PP}$ = 222.8 |
| b-Cl | 63.8 and 78.7 | 40.3 and 71.9 |
| R = iPr, X = Cl | $^2J_{PP}$ = 183.2 | $^2J_{PP}$ 217.6 |

$^a$ Assignment of cis and trans isomers c.f. the isolation of trans-Fe(P$_{Cy}$—CH=N—P$_{Ph}$)(Br)$_2$(CO).

trans-[Fe(Ph$_2$PCH$_2$CH$_2$NCHCH$_2$PCy$_2$)(CO)$_2$(Br)][BF$_4$], 4a: A Schlenk flask was charged with 1a (200 mg, 0.311 mmol) and KOtBu (70 mg, 0.623 mmol) and 25 mL THF, forming a slurry. The slurry was allowed to stir for 10 min by which time the mixture turned cloudy. To this solution, 2-(diphenylphosphino)ethylamine (143 mg, 0.623 mmol) was added, followed by FeBr$_2$ (204 mg, 0.934 mmol). The Schlenk flask was then exposed to an atmosphere of CO (~2 atm); upon exposure to CO, the pale yellow slurry immediately turned dark purple. The reaction mixture was allowed to stir for 5 hours by which time it was red-purple in color. The solvent was removed and any residue was taken up in 25 mL dichloromethane. This solution was filtered through a pad of Celite into a new Schlenk flask and exposed again to a CO atm. AgBF$_4$ (130 mg, 0.668 mmol) in 5 mL THF was injected into the reaction mixture. The solution immediately changed to a bright purple color. After stirring for 30 min, the solvent was removed, taken up in dichloromethane and filtered through a pad of Celite to remove a grey precipitate. The solvent was concentrated and pentane (10 mL) was added to cause precipitation of a purple solid. The solid was washed with pentane (5 mL) and dried under vacuum. Yield: 89% (454 mg). $^1$H NMR (400 MHz, CD$_2$Cl$_2$) δ: 1.16-2.50 (m, 22H, HCy), 2.50 (m, 2H, CH$_2$PCy$_2$), 2.92 (m, 2H, CH$_2$PPh$_2$), 3.63 (m, 2H, CH$_2$N), 7.56-7.95 (m, 11H, HPh, HCN). $^{13}$C {$^1$H} NMR (100 MHz, CD$_2$Cl$_2$) δ: 25.7 (CCy), 27.2 (CCy), 28.5 (CCy), 28.8 (CCy), 37.5 (CH$_2$PPh$_2$), 37.7 (CH$_2$PCy$_2$), 63.6 (CH$_2$N), 129.4 (CPh), 131.0 (CPh), 131.8 (CPh), 182.0 (HCN), 211.5 (dd, $J_{CP}$=22, 25 Hz, CO). $^{31}$P {$^1$H} NMR (161 MHz, CD$_2$Cl$_2$) δ: 45.7 (d, $J_{PP}$=85 Hz, PPh$_2$), 70.8 (d, $J_{PP}$=85 Hz, PCy$_2$). $^{19}$F{$^1$H} NMR (356 MHz, CD$_2$Cl$_2$) δ: −155.5 (s, BF$_4$) ppm. IR (KBr) 2005 cm$^{-1}$ ($\nu_{C=O}$). Anal. Calcd for C$_{30}$H$_{39}$NO$_2$P$_2$FeBrBF$_4$: C, 49.35; H, 5.38; N, 1.92. Found: C, 45.94; H, 5.47; N, 1.52. MS (ESI, methanol/water; m/z$^+$): −644.1 [C$_{30}$H$_{39}$NO$_2$P$_2$FeBr]$^+$. FIG. 4B depicts an ORTEP plot (thermal ellipsoids at 30% probability) of the X-ray crystal structures of 4a, where BPh$_4$ anion and hydrogen atoms of substituents removed for clarity. Selected bond lengths (Å) and angles (deg) of 4a: Fe(1)-C(6): 1.829(4); Fe(1)-N(1): 1.980(3); Fe(1)-P(2): 2.271(1); Fe(1)-Br(1): 2.4416(6); O(1)-C(5): 1.104(4); O(2)-C(6): 1.132(4); N(1)-C(3): 1.275(5); N(1)-C(2): 1.482(4); C(6)-Fe(1)-C(5): 172.2 (2); P(2)-Fe(1)-P(1): 168.38(4); N(1)-Fe(1)-Br(1): 175.35 (9).

trans-[Fe(Ph$_2$PCH$_2$CH$_2$NCHCH$_2$PiPr$_2$)(CO)$_2$(Br)][BF$_4$], 4b: The purple solid product was synthesized and isolated using the procedure outlined for 4a: 1b (200 mg, 0.415 mmol); KOtBu (93 mg, 0.830 mmol); 2-(diphenylphosphino)ethylamine (190 mg, 0.830 mmol); FeBr$_2$ (271 mg, 1.245 mmol); AgBF$_4$ (201 mg, 1.035 mmol). Yield: 83% (450 mg). $^1$H NMR (400 MHz, CD$_2$Cl$_2$) δ: 1.13 (m, 2H, CH(CH$_3$)$_2$), 1.45 (m, 12H, CH$_3$), 2.78 (m, 2H, CH$_2$PiPr$_2$), 2.90 (m, 2H, CH$_2$PPh$_2$), 3.62 (m, 2H, CH$_2$N), 7.53 (m, 4H, HPh), 7.91 (m, 7H, HPh, CHN). $^{13}$C {$^1$H} NMR (100 MHz, CD$_2$Cl$_2$) δ: 15.5 (CH(CH$_3$)$_2$), 19.1 (CH$_3$), 28.2 (CH$_2$PiPr$_2$), 28.3 (CH$_2$PPh$_2$), 63.0 (CH$_2$N), 129.8 (CPh), 131.8 (CPh), 132.1 (CPh), 181.7 (HCN), 211.5 (dd, $J_{CP}$=22, 25 Hz, CO). $^{31}$P {$^1$H} NMR (161 MHz, CD$_2$Cl$_2$) δ: 45.5 (d, $J_{PP}$=86 Hz, PPh$_2$), 78.2 (d, $J_{PP}$=86 Hz, PiPr$_2$). $^{19}$F{$^1$H} NMR (356 MHz, CD$_2$Cl$_2$) δ: −155.5 (s, BF$_4$) ppm. IR (KBr) 2011 cm$^{-1}$ ($\nu_{C=O}$). Anal. Calcd for C$_{24}$H$_{31}$NO$_2$P$_2$FeBr$_2$BF$_4$: C, 44.35; H, 4.81; N, 2.15. Found: C, 43.21; H, 4.88; N, 2.09. MS (ESI, methanol/water; m/z$^+$): 563.2 [C$_{24}$H$_{31}$NP$_2$O$_2$FeBr]$^+$. FIG. 4C depicts an ORTEP plot (thermal ellipsoids at 30% probability) of the X-ray crystal structures of 4b. Selected bond lengths (Å) and angles (deg) of 4b: Fe(1)-P(1): 2.265 (2); Fe(1)-N(1): 1.980(4); Fe(1)-C(12): 1.803(6); Br(1)-Fe (1): 2.4530(8); O(2)-C(12): 1.144(6); N(1)-C(2): 1.270(6); N(1)-C(3): 1.477(7); C(12)-Fe(1)-C(11): 170.4(2); P(1)-Fe (1)-P(2): 167.40(5); N(1)-Fe(1)-Br(1): 174.9(1).

trans-[Fe(Ph$_2$PCH$_2$CH$_2$NCHCH$_2$PPh$_2$)(CO)$_2$(Br)][BF$_4$], 4c. The purple solid product was synthesized and isolated using the procedure outlined for 4a: 1c (200 mg, 0.324 mmol); KOtBu (73 mg, 0.648 mmol); 2-(diphenylphosphino)ethylamine (149 mg, 0.648 mmol); FeBr$_2$ (208 mg, 0.971 mmol); AgBF$_4$ (157 mg, 0.809 mmol). Yield: 89% (454 mg). $^1$H NMR (400 MHz, CD$_2$Cl$_2$) δ: 2.16 (m, 2H, CH$_2$PPh$_2$), 2.99 (m, 2H, CH$_2$N), 3.77 (m, 2H, CH$_2$PPh$_2$), 7.54-7.94 (m, 21H, HPh, CHN). $^{13}$C {$^1$H} NMR (100 MHz, CD$_2$Cl$_2$) δ: 29.2 (CH$_2$PPh$_2$), 31.7 (CH$_2$Ph$_2$), 62.5 (CH$_2$N), 129.4 (CPh), 131.6-132.2 (CPh), 182.4 (CHN), 208.8 (br t, $J_{CP}$=24 Hz, CO). $^{31}$P {$^1$H} NMR (161 MHz, CD$_2$Cl$_2$) δ: 47.4 (d, $J_{PP}$=95 Hz, PPh$_2$), 51.9 (d, $J_{PP}$=95 Hz, PCy$_2$). $^{19}$F{$^1$H} NMR (356 MHz, CD$_2$Cl$_2$) δ: −155.5 (s, BF$_4$) ppm. IR (KBr) 2016 cm$^{-1}$ ($\nu_{C=O}$). Anal. Calcd for C$_{30}$H$_{27}$NO$_2$P$_2$FeBrBF$_4$: C, 50.18; H, 3.79; N, 1.92. Found: C, 44.38; H, 4.21; N, 1.58. MS (ESI, methanol/water; m/z$^+$): 632.0 [C$_{30}$H$_{27}$NO$_2$P$_2$FeBr]$^+$.

trans-(S,S)-[Fe(Ph$_2$PCH(Ph)CH(Me)NCHCH$_2$PCy$_2$)(CO)$_2$(Br)][BF$_4$], (S,S)-4d:

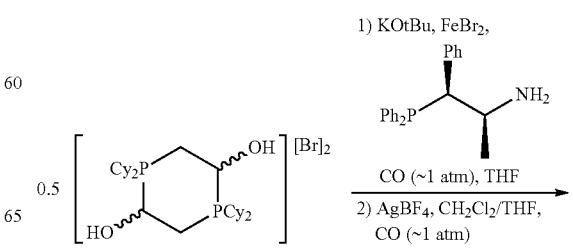

-continued

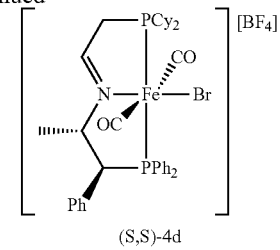

(S,S)-4d

The red-purple solid product was synthesized and isolated using the procedure outlined for 4a: 1a (100 mg, 0.156 mmol); KOtBu (35 mg, 0.312 mmol); (S,S)-Ph$_2$PCH(Ph)CH(Me)NH$_2$ (100 mg, 0.312 mmol); FeBr$_2$ (100 mg, 0.312 mmol); AgBF$_4$ (70 mg, 0.359 mmol). Yield: 82% (200 mg). $^1$H NMR (400 MHz, THF-d$_8$) δ: 0.72-2.05 (m, HCy), 1.11 (CH$_3$, indirectly determined via $^1$H—$^1$H COSY), 2.21 (m, 1H, HCy), 2.61 (m, 1H, HCy), 3.43 (CH$_2$PCy$_2$, indirectly determined via $^1$H—$^1$H COSY), 3.67 (CH$_2$PCy$_2$, indirectly determined via $^1$H—$^1$H COSY), 3.85 (m, 1H, CH(Me)), 4.14 (m, 1H, CH(Ph)), 6.80-7.97 (m, 16H, HPh), 7.96 (d, indirectly determined via $^1$H—$^1$H COSY, J$_{HP}$=20 Hz, CHN). $^{13}$C {$^1$H} NMR (100 MHz, THF-d$_8$) δ: 12.5 (CCy), 17.2 (CCy), 21.3 (CCy), 27.1 (CCy), 28.4 (CCy), 35.4 (CH$_2$PCy$_2$), 37.3 (CCy), 38.2 (CCy), 51.8 (CH(Ph)), 70.4 (CH(Me)), 126.0-135.3 (CPh), 179.3 (CHN), 210.5 (br t, J$_{CP}$=23.5 Hz, CO), 214.7 (br t, J$_{CP}$=21.3 Hz, CO). $^{31}$P {$^1$H} NMR (161 MHz, THF-d) δ: 69.2 (d, J$_{PP}$=81 Hz), 67.8 (d, J$_{PP}$=81 Hz). $^{19}$F{$^1$H}NMR (356 MHz, THF-d$_8$) □: −155.9 (s, BF$_4$) ppm. IR (KBr) 2000.0 cm$^{-1}$ (ν$_{C≡O}$). Anal. Calcd for C$_{37}$H$_{45}$NO$_2$P$_2$FeBrBF$_4$: C, 54.17; H, 5.53; N, 1.71. Found: C, 46.31; H, 6.08; N, 1.05. MS (ESI, methanol/water; m/z$^+$): 734.1 [C$_{37}$H$_{45}$NO$_2$P$_2$FeBr]$^+$.

cis-[Fe(Ph$_2$PC$_2$H$_4$NCHCH$_2$PCy$_2$)(CO)$_2$(Br)][BPh$_4$] (cis-4a): $^1$H NMR (400 MHz, CD$_2$Cl$_2$) δ: 1.31-2.11 (m, 22H, HCy), 2.61 (m, 2H, CH$_2$PPh$_2$), 2.79 (m, 2H, CH$_2$PCy$_2$), 3.00 (m, 1H, CH$_2$N), 3.44 (ddd, J$_{HH}$=12.0, 8.0 Hz, J$_{PH}$=40.0 Hz, CH$_2$N), 6.15 (d, J$_{HP}$=25.0 Hz, HCN), 6.86-7.70 (m, 30H, HPh). $^{13}$C {$^1$H} NMR (100 MHz, CD$_2$Cl$_2$) δ: 25.46 (d, J$_{CP}$=13.6, CCy), 26.20 (CCy), 26.50 (CCy), 25.52 (d, J$_{CP}$=10 Hz, CCy), 26.69 (d, J$_{CP}$=11.6 Hz, CCy), 27.12 (d, J$_{CP}$=10.4 Hz, CCy), 27.48 (d, J$_{CP}$=12.8 Hz, CCy), 27.97 (CCy), 28.65 (CCy), 29.95 (d, J$_{CP}$=5.1 Hz, CCy), 30.50 (CCy), 36.80 (d, J$_{CP}$=24.0 Hz, CH$_2$PPh$_2$), 37.2 (d, J$_{CP}$=25.0 Hz, CH$_2$PCy$_2$), 38.16 (d, J$_{CP}$=18.4 Hz, CCy), 61.84 (CH$_2$N), 122.40 (m, BCPh), 126.30 (m, BCPh), 128.90 (d, J$_{CP}$=9.0 Hz, CPh), 129.80 (d, J$_{CP}$=10.0 Hz, CPh), 130.21 (d, J$_{CP}$=9.0 Hz, CPh), 131.20 (d, J$_{CP}$=9.0 Hz, CPh), 132.70 (d, J$_{CP}$=8.0 Hz, CPh), 136.30 (m, BCPh), 164.30 (m, J$_{CB}$=49.0 Hz, BPh), 179.50 (HCN), 210.70 (t, J$_{CP}$=21.1 Hz, CO), 211.80 (br. dd, J$_{CP}$=19.0 Hz, CO). $^{31}$P {$^1$H} NMR (161 MHz, CD$_2$Cl$_2$) δ: 59.6 (d, J$_{PP}$=145 Hz, PPh$_2$), 78.9 (d, J$_{PP}$=145 Hz, PCy$_2$) ppm. IR (KBr) 2038 cm$_{-1}$ (ν$_{C≡O}$); 1990 cm$^{-1}$ (ν$_{C≡O}$). Anal. Calcd for C$_{54}$H$_{59}$NO$_2$P$_2$FeBrB: C, 67.38; H, 6.18; N, 1.46. Found: C, 65.84; H, 6.56; N, 1.49.

General Synthesis of Mer-trans-[Fe(Br)(CO)$_2$(P—N—P′)][BF$_4$] Precatalysts (S)-4e,f,g (Table 2a):

In a nitrogen filled glovebox, dicyclohexylphosphonium dimer (0.05 g, 0.078 mmol) and potassium tert-butoxide (0.018 g, 0.16 mmol) were stirred in 8 mL THF for 10 minutes to yield a cloudy white solution. To this solution, a phosphine-amine of formula (III) (0.16 mmol) and FeBr$_2$ (0.05 g, 0.23 mmol) were added, yielding a pale yellow solution, and the flask was transferred to a Schlenk line and put under a CO$_{(g)}$ atmosphere. Immediately upon exposure, the solution turned purple. This solution was stirred under CO$_{(g)}$ (~2 atm) for 5 hours to yield a deep red-purple solution, which was then dried under reduced pressure, transferred to a nitrogen filled glovebox, and redissolved in 8 mL of DCM. This solution was filtered through Celite, transferred back to a Schlenk line, and exposed to a CO$_{(g)}$ atmosphere. AgBF$_4$ (0.033 g, 17 mmol) in 2 mL of THF was injected into the solution and stirred for 30 minutes. Solvent was removed under reduced pressure to give a residue, and the flask transferred back into a nitrogen filled glovebox. The residue was redissolved in 5 mL of DCM, filtered through Celite, and concentrated to ~1 mL under reduced pressure. 5 mL of pentane was added to precipitate out a deep purple powdered product, which was washed with diethyl ether, and dried under reduced pressure.

(S)-4e: R=Cy, R$^1$=iPr, R$^2$=H (Used AgPF$_6$ instead of AgBF$_4$); Yield=120 mg=78%; $^1$H NMR (400 MHz, THF-d$_8$) δ: 8.16 (m, 1H, Ph-CH), 7.92 (m, 1H, Ph-CH), 7.05-7.68 (m, 9H, Ph-CH and N=CH at 7.58—determined indirectly for $^1$H-$^{13}$C HSQC), 3.26 (m, 1H, N—C(iPr)H), 2.98 (m, 2H, CH$_2$—PPh), 2.35 (m, 2H, CH$_2$—PCy), 1.21 (iPr-CH, determined indirectly for $^1$H—$^1$H COSY), 0.75 (m, 6H, iPr-CH$_3$) and 0.6-2.1 (m, PCy-H) ppm; $^{31}$P {$^1$H} (161 MHz, THF-d$_8$) δ: 63.28 (d, $^2$J$_{PP}$=81.6 Hz), 46.26 (d, $^2$J$_{PP}$=81.6 Hz) and −137.56 (m, PF$_6$) ppm; $^{13}$C {$^1$H} (100 MHz, THF-d$_8$) δ: 163.19 (N=CH), 129-135 (Ph-CH), 67.02 (N—C(iPr)H), 42.70 (CH$_2$—PPh), 35.80 (PCy$_2$-C), 32.52 (CH$_2$—PCy), 20-30 (PCy$_2$-C), 24.07 (iPr-CH) and 15.23 (iPr-CH$_3$) ppm; $^{19}$F {$^1$H} (356 MHz, THF-d$_8$) δ: −64.13 (d, PF$_6^-$, J=790 Hz) ppm. Anal. Calcd. for [FeC$_{37}$H$_{45}$P$_2$NO$_2$Br][PF$_6$]: C, 47.73; H, 5.46; N, 1.69. Found: C, 40.09; H, 6.17; N, 1.80. ** MS (ESI, m/z$^+$): 686.1 [FeC$_{33}$H$_{45}$P$_2$NO$_2$Br]$^+$ and 628.2 [FeC$_{31}$H$_{45}$P$_2$NBr]$^+$ (loss of two —CO). IR: ν(CO)=2005.8 cm$^{-1}$.

(S)-4f: R Cy, R$^1$=Ph, R$^2$=H; Yield=110 mg=86%; $^1$H NMR (400 MHz, THF-d$_8$) δ: 8.15 (m, 2H, Ar—CH and P—Ar—CH), 8.01 (m, 2H, Ar—CH and P—Ar—CH), 7.1-7.6 (m, Ar—CH and P—Ar—CH), 7.21 (N=CH, determined indirectly from $^1$H—$^1$H COSY), 4.51 (t, 1H, N—CH, J=11.6 Hz), 3.63 (CH$_2$—PPh$_2$, determined indirectly from $^1$H—$^1$H COSY), 3.58 (CH$_2$—PCy$_2$, determined indirectly from $^1$H—$^1$H COSY), 3.39 (CH$_2$—PCy$_2$, determined indirectly from $^1$H—$^1$H COSY), 3.13 (dd, 1H, CH$_2$—PPh$_2$, J=5.1 and 13.1 Hz) and 0.9-2.6 (m, PCy-H) ppm; $^{31}$P {$^1$H} (161 MHz, THF-d$_8$) δ: 66.76 (d, $^2$J$_{PP}$=81.9 Hz) and 39.35 (d, $^2$J$_{PP}$=81.6 Hz) ppm; $^{13}$C {$^1$H} (100 MHz, THF-d) b: 181.6 (N=CH), 128-133 (Ar—CH and P—Ar—CH), 74.1 (N—CH), 38.5 (PCy-C), 36.1 (PCy$_2$-CH$_2$), 34.5 (PPh$_2$-CH$_2$), 25-29 (PCy-C) and 13.3 (PCy$_2$-C) ppm; $^{19}$F {$^1$H} (356 MHz, THF-d$_8$) δ: −153 ppm; Anal. Calcd. for [FeC$_{36}$H$_{43}$P$_2$NO$_2$Br][BF$_4$]: C, 53.6; H, 5.40; N, 1.70. Found: C, 41.93; H, 4.98; N, 1.40**; MS (ESI, m/z$^+$): 720.1 [FeC$_{36}$H$_{43}$P$_2$NO$_2$Br]$^+$. IR: ν(CO)=2009.2 cm$^{-1}$.

(S)-4g: R$^1$=CH$_2$Ph, R$^2$=H; Yield=110 mg=84%; $^1$H NMR (400 MHz, THF-d$_8$) b: 8.13 (m, 1H, N=CH), 7.74 (m, 1H, Ar—CH and P—Ar—CH), 6.9-7.5 (m, 14H, Ar—CH and P—Ar—CH), 3.61 (N—CH, determined indirectly from $^1$H—$^1$H COSY), 3.30 (CH$_2$—PCy$_2$, determined indirectly from $^1$H—$^1$H COSY), 3.03 (CH$_2$—PPh$_2$, determined indirectly from $^1$H—$^1$H COSY), 2.86 ((CH$_2$—PPh$_2$, determined indirectly from $^1$H—$^1$H COSY), 1.33 (CH$_2$-Ph, determined indirectly from $^1$H—$^1$H COSY) and 0.8-2.5 (m, PCy-H) ppm; $^{31}$P {$^1$H} (161 MHz, THF-d$_8$) δ: 64.20 (d, $^2$J$_{PP}$=82.1 Hz) and 42.55 (d, $^2$J$_{PP}$=82.1 Hz) ppm; $^{13}$C {$^1$H} (100 MHz, THF-d$_8$) δ: 146.7 (N=CH), 127-133 (Ar—CH and P—Ar—CH), 66.5 (N—CH), 41.1 (CH$_2$—PPh$_2$), 38.6 (CH$_2$—PCy$_2$), 26.9 (CH$_2$-Ph) and 22-28 (PCy-C) and 13.6

(PCy$_2$-C) ppm; $^{19}$F {$^1$H} (356 MHz, THF-d$_8$) δ: −153.3 ppm. Anal. Calcd. for [FeC$_{37}$H$_{45}$P$_2$NO$_2$Br][BF$_4$]: C, 54.2; H, 5.5; N, 1.7. Found: C, 47.35; H, 5.39; N, 1.83**; MS (ESI, m/z$^+$): 734.1 [FeC$_{37}$H$_{45}$P$_2$NO$_2$Br]+ and 676.1 [FeC$_{35}$H$_{45}$P$_2$NBr]$^+$ (loss of two —CO). IR: v(CO)=2004.4 cm$^{-1}$.

**Please note: It was observed that analysis of some complexes resulted in unsatisfactory carbon content, but acceptable hydrogen and nitrogen content. The unsatisfactory carbon content was expected to be a result of a combustion problem due to the tetrafluoroborate, hexafluorophosphate and tetraphenylborate anions, as has been previously reported in literature [Marcó, A.; Compañó, R.; Rubio, R.; Casals, I. Microchim. Acta 2003, 142, 13].

Discussion

Synthesis of iron(II)-P—CH=N—P' complexes [Fe(Ph$_2$PCH$_2$CH$_2$N=CHCH$_2$PR$_2$) (NCCH$_3$)$_3$]$^{2+}$, where R=Ph or Cy, has been previously reported, and involved a multi-component template synthesis using a cyclic phosphonium salt as a source of phosphine-aldehyde, [Fe(H$_2$O)$_6$][BF$_4$]$_2$, KOtBu and 2-(diphenylphosphino)ethylamine in acetonitrile [Lagaditis, P. O.; Mikhailine, A. A.; Lough, A. J.; Morris, R. H. Inorg. Chem. 2010, 49, 1094-1102]. These P—CH=N—P'-pincer ligands possessed inequivalent phosphorus donors, a feature which is not readily achieved by conventional means of synthesis of P—N—P-pincer ligands [Liang, L.-C.; Li, C.-W.; Lee, P.-Y.; Chang, C.-H.; Man Lee, H. Dalton Trans. 2011, 40, 9004-9011; Liang, L.-C.; Chien, P.-S.; Lee, P.-Y. Organometallics 2008, 27, 3082-3093; Lansing Jr., R. B.; Goldberg, K. I.; Kemp, R. A. Dalton Trans. 2011, 40, 8950-8958]. $^{31}$P{$^1$H} NMR spectra of both complexes displayed two AB doublets with a large $^2$J$_{PP}$ coupling of 160 Hz for R=Ph and 148 Hz for R=Cy, which indicated that the P were trans; thus indicating a mer-arrangement of the P—CH=N—P' ligand about iron.

Figure 2:
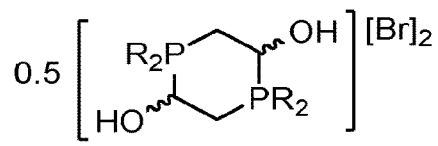
FIG. 2 depicts a template synthesis of iron complexes, trans-[Fe(P—CH=N—P')(CO)$_2$(Br)][BF$_4$]
Figure 2:
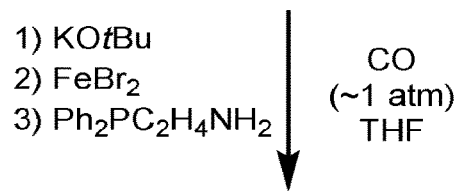
Figure 2:
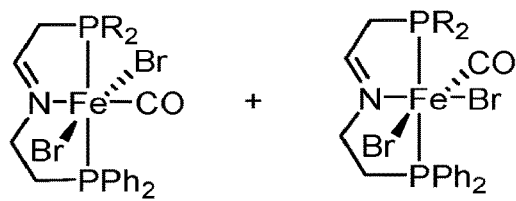

This template synthesis was modified for the herein described technology, and used FeBr$_2$ as an iron source (see FIG. 2). The synthesis was conducted in THF under a N$_2$ atm to potentially facilitate isolating an Fe(P—CH=N—P')(Br)$_2$ complex; however, no reaction occurred until exposure to carbon monoxide. Upon exposure, the reaction mixture (a pale yellow slurry) immediately turned red-purple. After stirring for a sufficient time (5 h) and removing salts (KBr and excess FeBr$_2$) a red-purple solid was isolated. Starting with phosphonium dimer 1a where R=Cy, iron compounds were produced in approximately a 1:1 ratio based on $^{31}$P{$^1$H} NMR spectra. One set of doublets was observed at 67.8 and 71.9 ppm ($^2$J$_{PP}$=172 Hz) and a second set at 39.6 and 60.5 ppm ($^2$J$_{PP}$=201 Hz). Large coupling constants were indicative that the P atoms of the P—CH=N—P' ligand were trans about the iron metal center. Similar results were obtained for 1b where R=iPr, and 1c where R=Ph (see paragraph [0063] above). Hence, two isomers of iron complexes were formed, trans-Br (2a-c) and cis-Br (3a-c) (see FIG. 2). Formation of two mer-Fe(P—CH=N—P')(CO)(Br)$_2$ isomers contrasted with Milstein's system where only a trans Br isomer was isolated [Langer, R.; Leitus, G.; Ben-David, Y.; Milstein, D. Angew. Chem. Int. Ed. 2011, 50, 2120-2124].

These results resembled those of Kirchner and co-workers who developed a synthesis of Fe(P—N—P)(CO)(X)$_2$ complexes, where X was Cl or Br, based on pincer ligand 2,6-(PiPr$_2$NH)$_2$C$_5$H$_3$N [Benito-Garagorri, D.; Alves, L. G.; Puchberger, M.; Mereiter, K.; Veiros, L. F.; Calhorda, M. J.; Carvalho, M. E.; Ferreira, L. P.; Godinho, M.; Kirchner, K. Organometallics 2009, 28, 6902-6914; Benito-Garagorri, D.; Puchberger, M.; Mereiter, K.; Kirchner, K. Angew. Chem. Int. Ed. 2008, 47, 9142-9145]. They found that when X was Cl, a cis isomer formed under solvent-free conditions, while a trans isomer formed in solution. However, where X was Br, a mixture of cis and trans isomers was always obtained. Consequently, an attempt to synthesize a Cl analogue of 2 and 3 was made using a Cl salt of 1a and FeCl$_2$ in the template synthesis; however, both cis and trans isomers formed, as evidenced by $^{31}$P{$^1$H} NMR spectrum of the reaction mixture (see paragraph [0063] above). Without wishing to be bound by theory, it was postulated that there was no control of cis and trans Br or Cl isomers since a multi-component reaction was being employed where the ligand was made in situ.

Consequently, compound Fe(CO)$_4$(Br)$_2$ [Benito-Garagorri, D.; Wiedermann, J.; Pollak, M.; Mereiter, K.; Kirchner, K. Organometallics 2007, 26, 217-222] was tested as a starting iron source, with reasoning that if halides were already coordinated to iron, and CO ligands were removed under UV light, one isomer could be selected for. When Fe(CO)$_4$(Br)$_2$ was used in place of FeBr$_2$, there was an immediate release of gas as well as a color change to orange. A $^{31}$P{$^1$H} NMR spectrum of this mixture revealed an intractable mixture. This was then exposed to UV light. After at least 5 h, the solution turned dark purple and a $^{31}$P{$^1$H} NMR spectrum of the solid isolated upon work up showed that the isomer at 67.8 and 71.9 ppm ($^2$J$_{PP}$=175 Hz) (R=Cy, R'=H) was the major species with on average less than 10% of other species. Crystals suitable for X-ray crystallography were isolated and confirmed selective formation of the trans-Fe(Cy$_2$PCH$_2$CH=NCH$_2$CH$_2$PPh$_2$)(CO)(Br)$_2$ complex, 2a (see FIG. 3). Complex trans-Fe(iPr$_2$PCH$_2$CH=NCH$_2$CH$_2$PPh$_2$)(CO)(Br)$_2$, 2b using phosphonium dimer 1b was also made in this manner. However in the case of phosphonium dimer 1c, a mixture of cis and trans isomers, 2c and 3c, were formed in every attempt.

These photochemical syntheses have several limitations, however, such as low yields and formation of cis-[Fe(P—CH=N—P')(CO)$_2$(Br)]$^+$. The UV template reaction was limited to only benzene or toluene as a solvent, as other solvents, such as THF or CH$_2$Cl$_2$ caused an increased amount of other iron-containing complexes. Furthermore, the reactions only worked well at small scales of less than 100 mg; otherwise, the amount of other isomers increased. One attempted scale up lead to a selective synthesis of cis-[Fe(P—N—P')(CO)$_2$(Br)]$_2$[FeBr$_4$] (cis-4a), as determined from X-ray crystallography, but this result was not reproducible (see FIG. 4D). This complex was isolated as the BPh$_4$$^-$ salt in order to remove paramagnetic FeBr$_4$$^{2-}$ anion and enable full characterization by NMR spectroscopy. Although a selective synthesis of cis-4a has been unsuccessful thus far, characterization of this compound allowed identification of its presence in crude products and distinguished the $^2$J$_{PP}$ constant from that of the trans-CO iron complexes 4a-d (FIG. 2). Reaction yields were low (on average 30%), but repeating the reaction at small scales repeatedly enabled a sufficient amount of the complexes trans-Fe(PCy-CH=N—PPh)(Br)$_2$(CO) and trans-Fe(P'Pr—CH=N—PPh)(Br)$_2$(CO) to be obtained for the synthesis' next step. Unfortunately, in every attempt to synthesize a hydride compound using either NaHBEt$_3$ or NaBH$_4$, intractable solids were isolated based on NMR spectra. As for LiAlH$_4$ (with subsequent addition of alcohol), at least two iron-hydride complexes were observed in NMR spectra, but it was realized that the P—N—P' ligand dissociated from the metal, at least to a certain extent, as negative chemical shift signals were observed. Hence, for the reaction of trans-Fe (PCy-CH=N—PPh)(Br)$_2$(CO) with LiAlH$_4$, followed by methanol, $^{31}$P{$^1$H} NMR spectrum showed signals at −2.28 and −20.22 ppm. Neither chemical shift corresponded to 2-(diphenylphosphino)ethylamine, nor to the phosphino-aldehyde, whose chemical shifts were −6 and −12 ppm, respectively. Both negative signals were from reduced P—N—P' ligand, (Ph$_2$PC$_2$H$_4$)NH(C$_2$H$_4$PCy$_2$). Use of a tertiary alcohol, such as t-amyl alcohol, helped reduce ligand dissociation, but did not completely prevent it. Thus, complexes trans-[Fe(P—N—P')(CO)$_2$(Br)][BF$_4$], 4a-d, were focussed on, and the photochemical synthesis was not pursued further.

Kirchner and co-workers reported formation of trans-[Fe (P—N—P)(CO)$_2$(Br)][BF$_4$] compounds selectively from reaction of a halide abstractor (such as AgBF$_4$) with a mixture of cis- and trans-Fe(P—N—P)(CO)(Br)$_2$ isomers [Benito-Garagorri, D.; Alves, L. G.; Veiros, L. F.; Standfest-Hauser, C. M.; Tanaka, S.; Mereiter, K.; Kirchner, K. *Organometallics* 2010, 29, 4932-4942]. Consequently, the template synthesis was adjusted to include AgBF$_4$, following the inclusion of which there was an immediate color change from red-purple to bright purple, the color of complexes 4a-c (FIG. 2). $^{31}$P{$^1$H} NMR spectra of isolated compounds showed formation of one new iron complex with AB doublets with smaller $^2J_{PP}$ couplings of 82 Hz (R=Cy), 85 Hz (R=iPr) and 94.5 Hz (R=Ph), significantly smaller than that of cis-[Fe(P—CH=N—P')(CO)$_2$(Br)]$^+$ with $^2J_{PP}$=145 Hz (see [00104]). Crystals of 4a and 4b suitable for X-ray crystallography were obtained (see above) and confirmed that trans-CO geometry about iron had also occurred. Without wishing to be bound by theory, it was considered that the mechanism for this selective trans configuration may have followed one proposed by Kirchner and co-workers, given that the reaction could also occur in the absence of carbon monoxide [Benito-Garagorri, D.; Alves, L. G.; Veiros, L. F.; Standfest-Hauser, C. M.; Tanaka, S.; Mereiter, K.; Kirchner, K. *Organometallics* 2010, 29, 4932-4942]. $^{13}$C{$^1$H} NMR spectra of complexes 4a-c displayed only one broad triplet or a doublet of doublets (dd) for CO ligands at around 210 ppm, which indicated that the complexes have C$_s$ symmetry, as expected. A $^{13}$CO analogue of 4b (henceforth referred to as 4b-$^{13}$CO) was synthesized to further confirm, via NMR spectroscopy, that two CO ligands were coordinated to iron. $^{31}$P{$^1$H} NMR (CD$_2$Cl$_2$) spectrum of 4b-$^{13}$CO displayed the same two phosphorus resonances as 4b at 45.47 and 78.31 ppm ($^2J_{PP}$=85.9 Hz, $^2J_{PC}$=21.8 Hz), but with a triplet of doublet multiplicity instead of a doublet for each phosphorus atom. The $^{13}$C{$^1$H} NMR spectrum of 4b-$^{13}$CO displayed one intense CO triplet resonance at 211.72 ppm ($^2J_{CP}$=24.0 Hz).

Chiral amino-phosphine ligand, (S,S)-2-amino-1-phenyl-propyldiphenylphosphine, was successfully used in the template synthesis method to generate a chiral complex: (S,S)-4d. (S,S)-4d was designed with Cy substituents on the ligand in anticipation that bulky groups would enhance enantiomeric interactions with substrates during catalysis. $^{13}$C{$^1$H} NMR spectrum of (S,S)-4d showed two inequivalent CO resonances with a dd pattern at 210.5 and 214.7 ppm. IR spectra of complexes 4a-d displayed only one ν$_{CO}$ absorption in a range of 2000 to 2011 cm$^{−1}$, similar to those of trans-CO iron complexes reported by Kirchner.

Example 2

Catalytic Hydrogenation

Experimental

All hydrogenation reactions were performed at constant pressures using a stainless steel 50 mL Parr hydrogenation reactor. Temperature was maintained at 50° C. using a constant temperature water bath. Reactor was flushed several times with hydrogen gas at 5 atm prior to addition of catalyst and substrate, and base solutions. For standard catalysis with in situ prepared catalysts, a vial was charged with [Fe(CO)$_2$(Br)(P—CH=N—P')]BF$_4$ (5 mg, 0.006 mmol) and 3 mL THF. To this solution, 0.05 mL of LiAlH$_4$ (1M in THF) was added and the solution's color immediately changed from purple to a golden brown. After stirring for 5 min, 2-methyl-2-butanol (0.5 mL) was added; the solution was allowed to stir for 10 min or until gas evolution ceased. The solution was transferred to a syringe equipped with a 12 inch needle. The same vial was then charged with substrate (6.095 mmol) and 3 mL THF. The solution was taken up into the same syringe that already contained the precatalyst solution; the needle was then stoppered. For catalysis with pre-formed species 7b and (S,S)-8d (see [00133-00134]), NMR solutions (THF-d$_8$) were transferred to a vial in a nitrogen filled glovebox and THF (6 mL) and substrate (6.095 mmol) were added. The solution was transferred to a syringe equipped with a 12 inch needle and stoppered. A second vial was charged with KOtBu (10 mg, 0.089 mmol) and 3 mL THF. This solution was transferred to a second syringe equipped with a 12 inch needle and stoppered as well. Both syringes were taken out of the glove box and injected into the prepared Parr reactor against a flow of hydrogen gas. Small aliquots of the reaction mixture were quickly withdrawn with a syringe and needle under a flow of hydrogen at timed intervals. Alternatively, small aliquots of the reaction mixture were sampled from a stainless steel sampling dip tube attached to a modified Parr reactor. The dip tube was 30 cm in length with an inner diameter of 0.01 inches, and a swing valve was attached to the end of the sampling tube. All samples for gas chromatography (GC) analyses were diluted to a total volume of approximately 1 mL using oxygenated ethanol. All conversions were reported as an average of two runs. Reported conversions were reproducible. Conversion and enantiomeric excess of hydrogenated ketones were analyzed by a Perkin-Elmer Clarus 400 chromatograph, equipped with a chiral column (CP chirasil-Dex CB 25 m×2.5 mm) and auto-sampling capability. Hydrogen was used as a mobile phase at a column pressure of 5 psi with a split flow rate of 50 mL/min. Injector temperature was 250° C. and FID temperature was 275° C. Oven temperatures and retention times (t$_{SM}$, t$_R$, t$_S$/min) for substrates were as follows[a]:

| Substrates/Alcohol Products | | Oven Temp. (° C.) | t$_{SM}$ (min) | t$_R$ (min) | t$_S$ (min) |
|---|---|---|---|---|---|
| 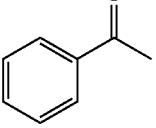 | 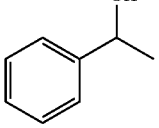 | 130 | 4.83 | 8.09 | 8.43 |

-continued
| Substrates/Alcohol Products | | Oven Temp. (° C.) | $t_{SM}$ (min) | $t_R$ (min) | $t_S$ (min) |
|---|---|---|---|---|---|
| 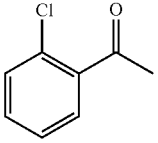 | 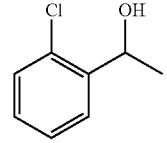 | 145 | 4.96 | 11.07 | 12.96 |
| 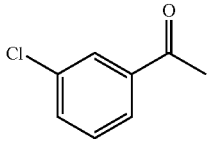 | 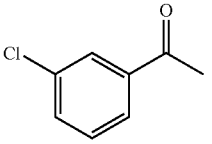 | 140 | 6.51 | 14.78 | 15.78 |
| 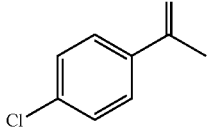 | 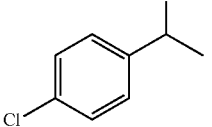 | 145 | 6.52 | 12.10 | 13.26 |
| 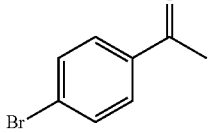 | 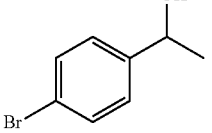 | 155 | 7.02 | 12.79 | 13.26 |
| 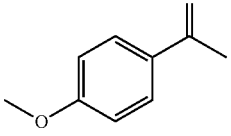 | 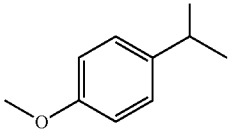 | 140 | 11.44 | 15.0 | 15.64 |
| 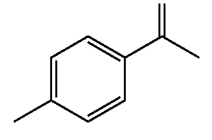 | 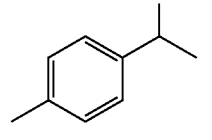 | 130 | 7.12 | 10.63 | 11.4 |
| 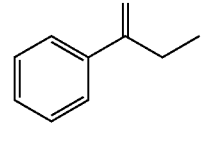 | 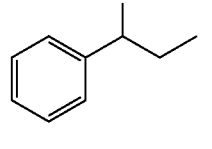 | 120 | 8.9 | 19.19 | 19.8 |
| 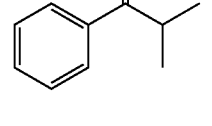 | 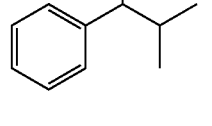 | 140 (90) | 5.28 (36.18) | 10.29 (181.83) | 10.29 (192.99) |
| 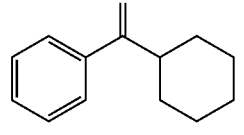 | 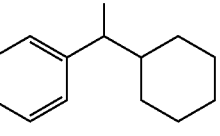 | 170 | 9.67 | 14.43 | 14.76 |

-continued
| Substrates/Alcohol Products | | Oven Temp. (° C.) | $t_{SM}$ (min) | $t_R$ (min) | $t_S$ (min) |
|---|---|---|---|---|---|
| 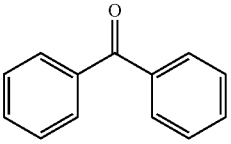 [SMILES: O=C(c1ccccc1)c1ccccc1] | 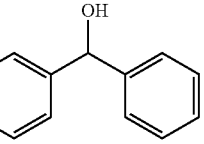 | 180 | 7.94 | | 12.50 |
| 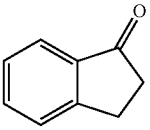 | 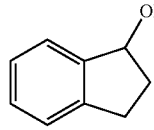 | 130 (90) | 6.81 (81.68) | 7.80 (164.50) | 7.80 (153.85) |
| 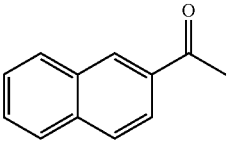 | 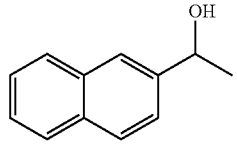 | 150 | 23.1 | 38.3 | 40.1 |
| 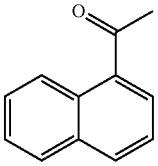 | 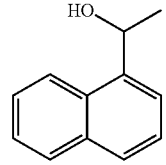 | 140 | 24.1 | 74.2 | 86.2 |
| 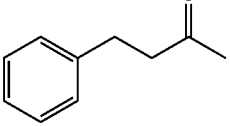 | 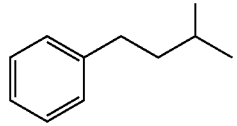 | 125 | 11.49 | 18.68 | 19.49 |
| 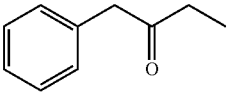 | 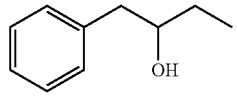 | 130 | 8.29 | 12.22 | 11.61 |
| 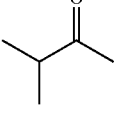 | 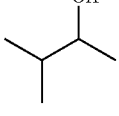 | 60 | 3.80 | 9.80 | 10.37 |
| 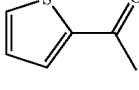 | 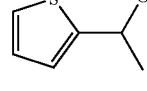 | 115 | 8.25 | 16.26 | 17.57 |
| 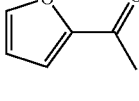 | 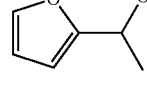 | 90 | 6.90 | 15.41 | 15.88 |
| 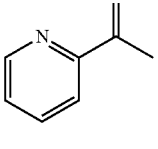 | 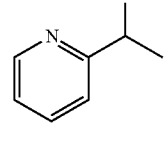 | n/a[a] | 9.64 | 12.11 | 12.97 |
| 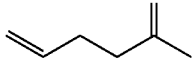 | 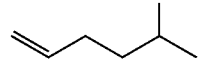 | 90 | 3.43 | 5.63 | 5.63 |

| Substrates/Alcohol Products | | Oven Temp. (° C.) | $t_{SM}$ (min) | $t_R$ (min) | $t_S$ (min) |
|---|---|---|---|---|---|
| benzaldehyde | benzyl alcohol | 130 | 3.53 | | 7.31 |
| N-(1-phenylpropylidene)-P,P-diphenylphosphinic amide | N-(1-phenylpropyl)-P,P-diphenylphosphinic amide | n/a[a] | 10.25 | 13.22 | 17.02 |

[a]HPLC conditions: isopropanol:hexanes = 10:90, flow rate = 0.5 mL/min.

Discussion

Discovery of precatalysts 4a-d activity towards hydrogenation was made while treating the iron dicarbonyl complexes with various hydride reagents to produce iron hydride amine complexes with a bifunctional HN—FeH group known to reduce C=O and C=N bonds [Morris, R. H. Chem. Soc. Rev. 2009, 38, 2282-2291; Mikhailine, A. A.; Maishan, M. I.; Lough, A. J.; Morris, R. H. J. Am. Chem. Soc. 2012, 134, 12266-12280; Zuo, W.; Li, Y.; Lough, A. J.; Morris, R. H. Science 2013, 342, 1080-1083]. Reactions with NaHBEt₃ or NaBH₄ formed intractable mixtures; LiAlH₄ was more promising. To generate iron hydrides, often a precursor was reacted with a slight excess of LiAlH₄ in THF [Antberg, M.; Frosin, K. M.; Dahlenburg, L. J. Organomet. Chem. 1988, 338, 319-327; Antberg, M.; Dahlenburg, L. Z. Naturforsch., B: Chem. Sci. 1985, 40, 1485-1489; Roger, C.; Marseille, P.; Salus, C.; Hamon, J.-R.; Lapinte, C. J. Organomet. Chem. 1987, 336, C13-C16; Field, L. D.; Messerle, B. A.; Smernik, R. J.; Hambley, T. W.; Turner, P. Inorg. Chem. 1997, 36, 2884-2892; Liu, T.; Chen, S.; O'Hagan, M. J.; Rakowski DuBois, M.; Bullock, R. M.; DuBois, D. L. J. Am. Chem. Soc. 2012, 134, 6257-6272]; sometimes with the addition of a protic solvent [Gao, Y.; Holah, D. G.; Hughes, A. N.; Spivak, G. J.; Havighurst, M. D.; Magnuson, V. R.; Polyakov, V. Polyhedron 1997, 16, 2797-2807; Ohki, Y.; Suzuki, H. Angew. Chem. Int. Ed. 2000, 39, 3120-3122; Argouarch, G.; Hamon, P.; Toupet, L.; Hamon, J.-R.; Lapinte, C. Organometallics 2002, 21, 1341-1348; Sellmann, D.; Weber, W. J. Organomet. Chem. 1986, 304, 195-201; Jia, G.; Drouin, S. D.; Jessop, P. G.; Lough, A. J.; Morris, R. H. Organometallics 1993, 12, 906-916]. For at least some the herein described complexes, it was found that addition of at least 6 equiv. of LiAlH₄ was necessary to produce a solution of iron hydride complexes reproducibly (see paragraph [00130]). The mixture was then treated with alcohol until gas evolution had ceased. Methanol, ethanol and tert-amyl alcohol (2-methyl-2-butanol, tAmylOH) were found to give active catalyst preparations. Then ketone or imine substrates and additional THF were added and the entire solution was injected into a prepared pressure reactor. This procedure allowed facile and efficient screening of optimal conditions for catalysis (see Table 1 below).

Figure 1:
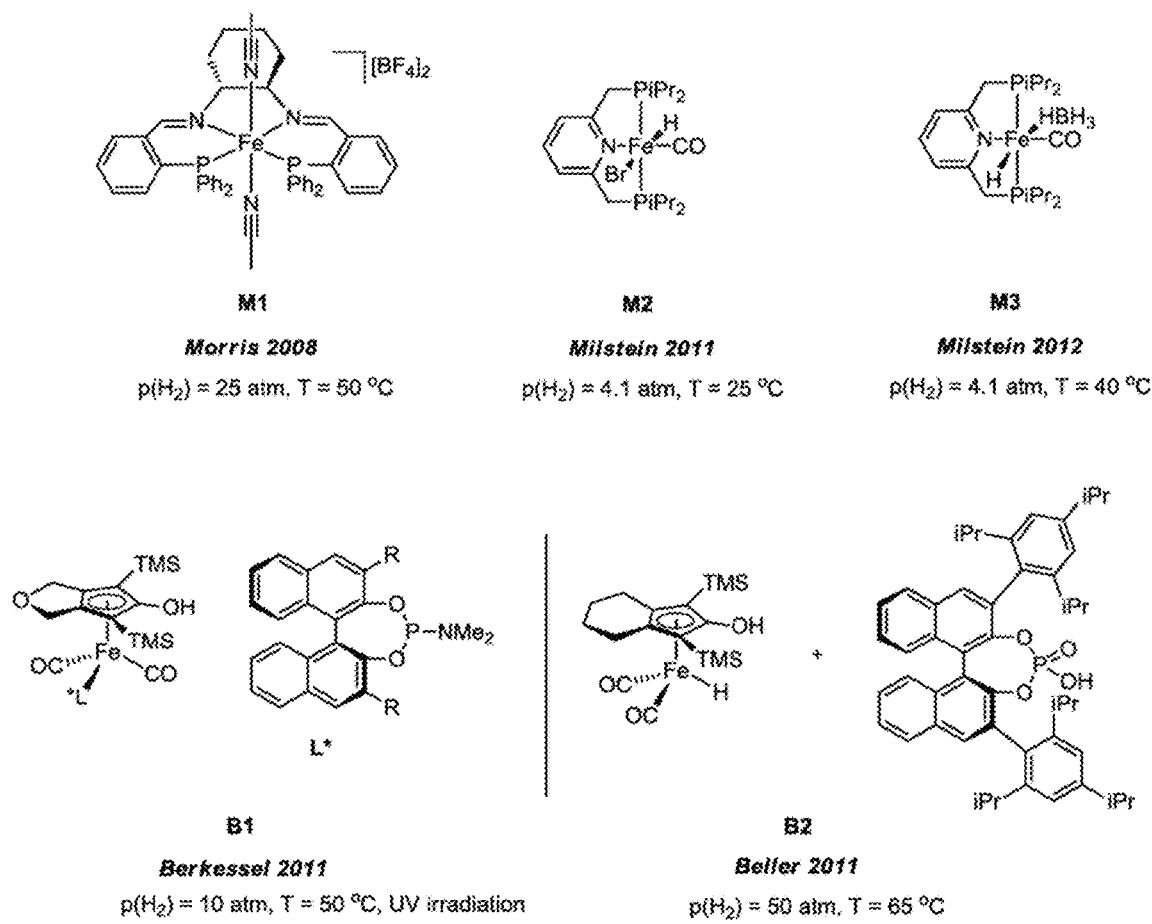
FIG. 1 depicts active iron catalysts for ketone (M1-3 and B1) and imine (B2) hydrogenation.

While 25 atm H₂ was an effective pressure for catalysis, 5 atm H₂ still resulted in full conversion of acetophenone to 1-phenylethanol within 10 min. Faster conversions were observed at 50° C. than at 25° C. (Table 1, Entry 2 vs 3). Substitution of LiAlH₄ with NaAlH₄ did not affect reaction rate (Entry 4). No catalysis was observed in absence of base (Entry 7), which prevented testing of base sensitive substrates. Use of a tertiary alcohol, tAmylOH, in the catalyst activation process created a more active system than with primary alcohols, MeOH or ethanol (Entry 2 vs 5 vs 6). Without wishing to be bound by theory, two possible explanations for the alcohol effect were considered: the catalyst activation period was slower with methoxide or ethoxide as a ligand; or, there were other deactivation processes occurring that were more pronounced with a primary alkoxide [Fiedler, A.; Schroder, D.; Schwarz, H.; Tjelta, B. L.; Armentrout, P. B. J. Am. Chem. Soc. 1996, 118, 5047-5055]. Use of a tertiary alcohol also had prevented non-selective transfer hydrogenation mediated by Al(OR)₃. It appeared that the P—N—P' ligand to containing at least one large alkyl-substituted phosphorus atom was beneficial for creating an active catalyst (Table 1, Entry 1 and 2 vs 9). TOF value for acetophenone hydrogenation using the 4a precatalyst (Entry 8, TON 2000, TOF 1980 h⁻¹ at 50° C. and 5 atm H₂) was comparable to that reported for Milstein's complexes M2, 430 h⁻¹ at 40° C., 4 atm H₂. One difference observed with the herein described complexes was that THF could be used in place of alcohol solvents needed for catalysis with M2 or M3 (FIG. 1).

For benzaldehyde hydrogenation, it was found that pressures of 10 atm H₂ gas facilitated achieving 90% conversion in 2.5 h versus 10 h with 5 atm H₂ gas:

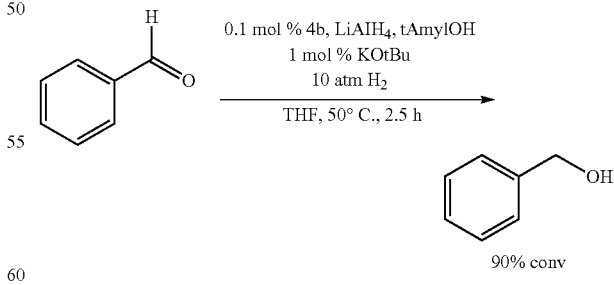

Substrate scope of asymmetric ketone hydrogenation reaction was investigated at 50° C. and 5 atm H₂ using 0.1 mol % of the activated mixture prepared from (S,S)-4d (see Table 2 below). Many aryl ketones were converted to alcohols with good enantioselectivity, typically about 80% (S). This system appeared to offer a higher activity towards enantioselective ketone hydrogenation over other iron-based catalysts (FIG. 1) given that it employed $H_2$ gas. It was interesting to note that the (S,S) chiral catalyst system produced (S) alcohol enantiomers, wherein (R) enantiomers of alcohols are generally expected when using ligands derived from (S,S)-diamine [Noyori, R.; Ohkuma, T. *Angew. Chem. Int. Ed.* 2001, 40, 40-73; Abdur-Rashid, K.; Faatz, M.; Lough, A. J.; Morris, R. H. *J. Am. Chem. Soc.* 2001, 123, 7473-7474; Clapham, S. E.; Hadzovic, A.; Morris, R. H. *Coord. Chem. Rev.* 2004, 248, 2201-2237].

A catalyst mixture starting with (S,S)-4d was tested for acetophenone hydrogenation at both 50° C. and 25° C. Enantioselectivity of the reaction increased from 80% to 89% (S), while time for complete conversion lengthened from 30 min to 90 min, respectively. The catalytic mixture at 50° C. also accommodated additional loadings of substrate: four additional batches of acetophenone (1000 equiv.) were added at 30 minute intervals without slowing down the catalyst or affecting the ee of product (S)-1-phenylethanol. A fifth batch slowed the catalytic reaction but it still went to completion. Enantioselectivity of the (S,S)-4d system decreased along with activity as steric hindrance due to bulky substituents on the ketone substrate increased (see Table 2, Entries 7 vs 8 vs 9). Low enantioselectivity was not due to racemization as the reactions were monitored periodically, and ee remained constant until completion. For less bulky substrates, such as benzylacetone (Entry 15), catalytic reduction by the (S,S)-4d system was rapid but enantioselectively poor (ee=5%). For substrate 1-phenyl-2-butanone (Entry 16), which was more sterically hindered than benzylacetone, ee increased to 30%, while there was a substantial decrease in catalytic activity (TOF=90 $h^{-1}$). This lower catalytic activity was considered to be a result of enolate formation due to presence of base. Fortunately, the inhibitory effect of enolates did not poison the catalyst completely. Pre-catalyst (S,S)-4d was found to give moderately efficient hydrogenations of non-aromatic ketones (Entry 17) but with inferior enantioselectivity (ee=46%). The system was also found to catalyze reduction of 2-acetylthiophene (Entry 18) and 2-acetylfuran (Entry 19) to near completion. However, catalysis was slower (TOF=240 $h^{-1}$ for 2-acetylthiophene and 220 $h^{-1}$ for 2-acetylfuran) when compared to acetophenone (TOF=990 $h^{-1}$). The difference was considered to be due to the heterocycle's heteroatom binding to the iron; however; since catalysis did go to completion, it was postulated that the chelation effect may be reversible. The chelation effect appeared to be more pronounced for substrate 2-acetylpyridine (Entry 20), such that catalysis ceased at 20% conversion (or 200 TON) after one hour. It was considered that the substrate, its alcohol product, or both, deactivate the catalyst. An increase in $H_2$ pressure to 10 atm enabled the hydrogenation of 2-acetylpyridine to 60% conversion (or 600 TON) in two hours and maintained a 74% ee of the hydrogenated product.

The (S,S)-4d system did not hydrogenate trans-4-phenyl-3-buten-2-one, unsaturated ketone, at 5 or 10 atm $H_2$ pressure (Table 2, Entry 21). An olefin group did not poison the catalyst, because the (S,S)-4d system was able to fully hydrogenate 5-hexen-2-one (Entry 22) to 5-hexen-2-ol without affecting the olefin as determined by NMR spectroscopy. However, in comparison with benzylacetone (Entry 15), where catalytic hydrogenation was complete in one hour, hydrogenation of 5-hexen-2-one was complete in four hours. Furthermore, upon addition of 1-hexene (500 equiv) to a hydrogenation reaction of acetophenone (1000 equiv), catalysis was complete in 90 min as opposed to 30 min. These results imply there may be some degree of reversible olefin coordination analogous to the situation with hetero-cyclic substrates (Entries 18-20). Enone and diene compounds of iron are known and have been well studied [Brookhart, M.; Nelson, G. O. *J. Organomet. Chem.* 1979, 164, 193-202; Moulton, B. E.; Duhme-Klair, A. K.; Fairlamb, I. J. S.; Lynam, J. M.; Whitwood, A. C. *Organometallics* 2007, 26, 6354-6365; Knolker, H.-J. *Chem. Rev.* 2000, 100, 2941-2962; Russell, S. K.; Milsmann, C.; Lobkovsky, E.; Weyhermuller, T.; Chirik, P. J. *Inorg. Chem.* 2011, 50, 3159-3169]. It was considered that there was some degree of reversible coordination with enones and dienes, as well with the presently claimed iron catalysts because, upon addition of trans-4-phenyl-3-buten-2-one (500 equiv) to a hydrogenation reaction of acetophenone (1000 equiv), catalysis was complete in 90 min with zero conversion of the enone additive.

Additional chiral complexes were tested for acetophenone hydrogenation at 50° C., and enantioselectivity for each reaction was evaluated. Results are outlined below (Table 2a).

Hydrogenation of imines was also investigated using activated (S,S)-4d under harsher conditions of 20 atm $H_2$ gas and at 50° C. at substrate loadings of 1 mol % (based on (S,S)-4d) and 10 mol % base. The system was found to be inactive for hydrogenation of imine substrates, N-(1-phenylethylidene)aniline, or phenyl-N-(1-phenylethylidene)methanamine, or nitrile substrate benzylnitrile. However, hydrogenation of activated imine, N-(diphenylphosphonyl) propiophenoneimine was observed in 22 h with a TOF of 5 $h^{-1}$:

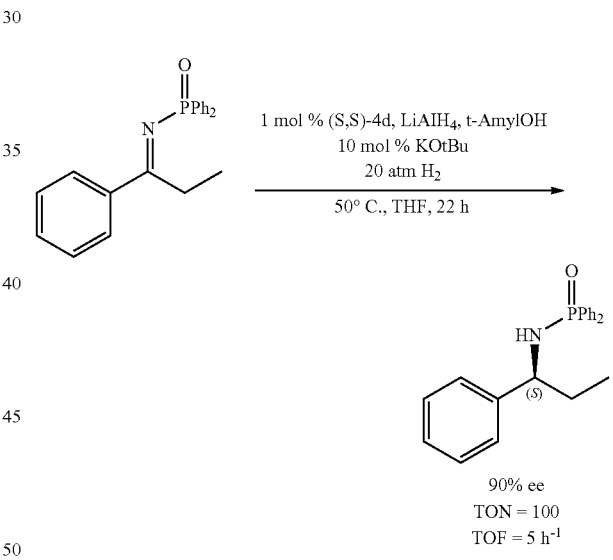

Activity of this system was observed to be higher than that of Beller and co-worker's cooperative system B2, which had a TOF of about 1 $h^{-1}$ under harsher conditions [Zhou, S.; Fleischer, S.; Junge, K.; Beller, M. *Angew. Chem. Int. Ed.* 2011, 50, 5120-5124]. Enantioselectivity of activated (S,S)-4d was high (ee=90% (S)).

Example 3

Study of Catalyst Activation Steps

Experimental

General Procedure for Synthesis of Complexes 5a-d and 6a-d: A vial was charged with [Fe(CO)$_2$(Br)(P—CH=N—P')][BF$_4$] (~20 mg) in THF (5 mL) to yield a bright purple solution to which LiAlH$_4$ was added until the solution turned dark yellow-brown (~20 mg). After stirring for 10 min, solvent was removed and a residue was taken up with ether (5-10 mL) to remove a grey-black precipitate. 12-crown-4 (~4-5 drops) was added to cause precipitation of an off-white solid ([Li(12-crown-4)]BH$_4$]). Resulting solution was filtered and dried in vacuo to yield a yellow residue.

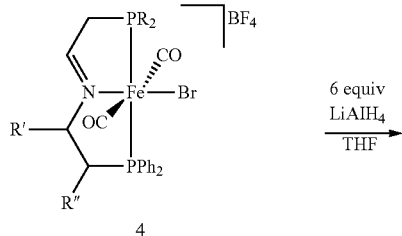

a) R = Cy; R', R" = H
b & b-$^{13}$CO) R = iPr; R', R" = H
c) R = Ph; R', R" = H
(S,S)-d) R = Cy; R' = Me; R' = Ph

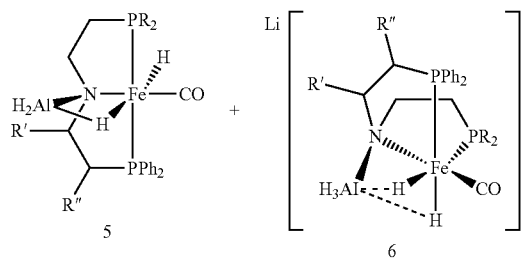

Chemical Shifts and Coupling Constants of Compounds from Reaction of 4b-$^{13}$CO with LiAlH$_4$:

| Nucleus (THF-d$_8$) | 5b-$^{13}$CO (ppm, $^2$J Hz) | 6b-$^{13}$CO (ppm, $^2$J Hz) | Unidentified minor product (ppm, $^2$J Hz) |
|---|---|---|---|
| $^1$H NMR (600 MHz) | −10.9 (br. s) −13.2 (tdd) $J_{HH}$ = 8 $J_{HP}$ = 54 $J_{HC}$ = 12 | −11.2 (m) −11.6 (m) $J_{HH}$ = 24 Hz | −11.7 (detected via $^1$H-$^{31}$P HMBC) |
| $^{31}$P{$^1$H} NMR (243 MHz) | 86.8 (dd) 107.5 (dd) $J_{PP}$ = 105 $J_{PC}$ = 27 | 83.6 (td) 100.7 (td) $J_{PP}$ = 20 $J_{PC}$ = 28 | 57.2 (d) 75.7 (d) $J_{PP}$ = 138 |
| $^{13}$C{$^1$H} NMR (150 MHz) | 221.4 (t) $J_{CP}$ = 26 | 220.3 (t) $J_{CP}$ = 39.0 | 220.1 (br. s) 220.4 (br. s) |

NMR Spectroscopy Chemical Shifts of Iron Hydride-Aluminumhydride Compounds with Coupling Constants (600 MHz, THF-d$_8$):

| | 5 (trans-dihydride) | | 6 (cis-dihydride) | |
|---|---|---|---|---|
| | $^1$H NMR (ppm, $^2$J Hz) | $^{31}$P NMR (ppm, $^2$J Hz) | $^1$H NMR (ppm, $^2$J Hz) | $^{31}$P NMR (ppm, $^2$J Hz) |
| 5a/6a R = Cy, R',R" = H | −10.9 (br. s) −13.2 (td) $J_{HH}$ = 8 $J_{HP}$ = 54 | 86.3 (d) 99.1 (d) $J_{PP}$ = 105 | −11.2 (m) $J_{HH}$ = 23 $J_{HP}$ ≈ 27, 37 $^a$ −11.7 (m) $J_{HH}$ = 23 $J_{HP}$ ≈ 28, 34 $^a$ | 83.0 (d) 91.1 (d) $J_{PP}$ = 20 |
| 5b/6b R = iPr, R',R" = H | −10.9 (br. s) −13.2 (td) $J_{HH}$ = 8 $J_{HP}$ = 54 | 86.8 (d) 107.5 (d) $J_{PP}$ = 105 | −11.2 (m) $J_{HH}$ = 24 $J_{HP}$ ≈ 28, 38 $^b$ −11.6 (m) $J_{HH}$ = 24 $J_{HP}$ ≈ 31, 37 $^b$ | 83.6 (d) 100.7 (d) $J_{PP}$ = 20 |
| 5c/6c R = Ph, R',R" = H | −10.6 (br. s) −12.6 (td) $J_{HH}$ = 8 $J_{HP}$ = 56 | 90.0 (s) | −10.9 (m)$^c$ | 86.4 (s) |
| (S,S)-5d/6d R = Cy, R' = Me R" = Ph | −10.9 (br. s) −12.5 (td) $J_{HH}$ = 8 $J_{HP}$ = 54 Hz | 97.8 (d) 98.3 (d) $J_{PP}$ = 102 | −10.5 (m) $J_{HH}$ = 23 $J_{HP}$ ≈ 29, 34 $^d$ −11.6 (m) $J_{HH}$ = 23 −10.8 (m) $J_{HH}$ = 22 −11.7 (m) $J_{HH}$ = 22 | 83.9 (d) 102.1 (d) $J_{PP}$ = 21 89.65 (d) 92.39 (d) $J_{PP}$ = 21 |

$^a$ See FIG. 5.
$^b$ See FIG. 6.
$^c$ $^1$H NMR (C6D6): −9.5 (m), −10.6 (m) ppm.
$^d$ See FIG. 7.

General Procedure for the Synthesis of Complexes 7 and 8:

Following the procedure as outlined for 5a-d and 6a-d, an excess of alcohol (MeOH or tAmylOH) was added dropwise to a final Et$_2$O solution until gas evolution ceased (~10 drops). The solution, originally yellow, turned orange. The solvent was removed and a residue was taken up with pentane and filtered. The solution was dried in vacuo to afford an orange residue.

NMR Chemical Shifts (THF-d$^8$) of Iron Pre-Catalysts of 7 and 8:

| | $^1$H NMR (600 MHz) (ppm, $^2$J Hz) | $^{31}$P{$^1$H} NMR (243 MHz) (ppm, $^2$J Hz) | $^{13}$C{$^1$H} NMR (150 MHz) (ppm, $^2$J Hz) |
|---|---|---|---|
| 7b-$^{13}$CO isomer I (R''' = Me) | −18.6 (td) $J_{HC}$ = 19 $J_{HP}$ = 52 | 82.8 (ddd) 102.1 (ddd) $J_{PH}$ = 39$^a$ $J_{PC}$ = 27 $J_{PP}$ = 119.1 | 222.3 (td) $J_{CH}$ = 14 $J_{CP}$ = 26 |

-continued

[Structure diagram of complex with PR$_2$, H, N, Fe, CO, O, PPh$_2$ ligands and substituents R', R''', R'']

| | $^1$H NMR (600 MHz) (ppm, $^2$J Hz) | $^{31}$P{$^1$H} NMR (243 MHz) (ppm, $^2$J Hz) | $^{13}$C{$^1$H} NMR (150 MHz) (ppm, $^2$J Hz) |
|---|---|---|---|
| 7b-$^{13}$CO isomer II (R''' = Me) | −21.6 (td) $J_{HC}$ = 20 $J_{HP}$ = 57 | 77.2 (ddd) 96.7 (ddd) $J_{PH}$ = 41$^a$ $J_{PC}$ = 27 $J_{PP}$ = 137 | 224.1 (td) $J_{CH}$ = 17 $J_{CP}$ = 27 |
| 7b-CO isomer III (R''' = Me) | −22.7 (dd) $J_{HP}$ = 52, 56 | 75.0 (dd) 95.7 (dd) $J_{PH}$ = 21$^a$ $J_{PP}$ = 136 | n/a |
| 8b isomer I (R''' = tAmyl) | −21.6 (dd) $J_{HP}$ = 52, 56 | 75.3 (dd) 94.8 (dd) $J_{PH}$ = 30$^a$ $J_{PP}$ = 137 | n/a |
| 8b isomer II (R''' = tAmyl) | −26.6 (dd) $J_{HP}$ = 60, 72 | 64.7 (dd) 86.6 (dd) $J_{PH}$ = 53 $J_{PP}$ = 152 | n/a |
| (S,S)-8d isomer I (R''' = tAmyl) | −21.6 (dd) $J_{HP}$ = 47, 56 | 95.4 (dd) 86.4 (dd) $J_{PH}$ = 49$^a$ $J_{PP}$ = 140 | n/a |
| (S,S)-8d isomer II (R''' = tAmyl) | −24.3 (t) $J_{HP}$ = 48 | 108.5 (d) 98.1 (d) $J_{PP}$ = 148 | n/a |

$^a$Residual coupling due to incomplete decoupling of the high field hydride resonance.

NMR Spectroscopy Chemical Shifts of Minor Iron Monohydride Compounds of (S,S)-8d as Determined from $^1$H—$^{31}$P HMBC NMR Spectrum:

| | Minor isomer i | Minor isomer j | Minor isomer k |
|---|---|---|---|
| $^1$H NMR (ppm, $^2$J Hz) | −24.2 (t) ($J_{HP}$ = 54) | −24.6 (dd) ($J_{HP}$ = 54, 64) | −25.2 (t) ($J_{HP}$ = 48) |
| $^{31}$P NMR (ppm) | 86.0 88.8 | 83.5 91.3 | 101.5 107.0 |

Density Functional Theory Calculations on Models of 5 and 6: DFT calculations were performed using Gaussian 09 [Frisch, M. J. et al., 2009, Gaussian 2009 Revision B. 2001]. M06 hybrid functional was used for all calculations [Zhao, Y.; Truhlar, D. *Theor. Chem. Acc* 2008, 120, 215-241; Zhao, Y.; Truhlar, D. G. *Acc. Chem. Res.* 2008, 41, 157-167]. All atoms were treated with a 6-31++G(d,p) basis set. A pruned (99,590) integration grid was used throughout (Grid=UltraFine). Optimizations were performed in tetrahydrofuran using an integral equation formalism polarizable continuum model (IEF-PCM) with radii and nonelectrostatic terms from a SMD solvation model [Marenich, A. V.; Cramer, C. J.; Truhlar, D. G. *J. Phys. Chem. B* 2009, 113, 6378-6396]. Full vibrational and thermochemical analyses (1 atm, 298 K) were performed on optimized structures to obtain solvent-corrected free energies (G°) and enthalpies (H°). Optimized ground states were found to have zero imaginary frequencies.

DFT Calculations (GAUSSIAN09/M06/6-31++G(d,p)/IEF-PCM (THF))—Coordinates for Complex FeH$_2$(CO)(PH$_2$CH$_2$CH$_2$N(AlH$_2$)CH$_2$CH$_2$PH$_2$) (Model of Compounds 5b; See FIG. 8):

| Fe | −0.03315 | 0.69757 | −0.02087 |
|---|---|---|---|
| P | 2.16119 | 0.61500 | −0.25240 |
| P | −2.20837 | 0.41626 | −0.26697 |
| N | 0.06413 | −1.38257 | −0.10934 |
| C | 2.54387 | −1.19015 | −0.36182 |
| H | 3.36300 | −1.39081 | −1.05957 |
| H | 2.86631 | −1.51414 | 0.63422 |
| C | 1.27051 | −1.89172 | −0.79469 |
| C | −2.42763 | −1.41778 | −0.31602 |
| H | −0.04300 | 0.60830 | 1.63923 |
| H | −0.02578 | 0.75183 | −1.55863 |
| C | −1.10464 | −2.01380 | −0.75820 |
| H | −3.23968 | −1.71509 | −0.98710 |
| H | −2.69748 | −1.73768 | 0.69685 |
| H | −1.00009 | −1.87992 | −1.84847 |
| H | −1.09850 | −3.09988 | −0.56733 |
| H | 1.36461 | −2.97796 | −0.63029 |
| H | 1.13193 | −1.74285 | −1.87913 |
| Al | 0.07311 | −1.11553 | 1.78927 |
| H | 1.46623 | −1.45158 | 2.49243 |
| H | −1.24674 | −1.62946 | 2.52569 |
| C | −0.11963 | 2.44108 | 0.06728 |
| O | −0.18343 | 3.60160 | 0.10271 |
| H | −2.82974 | 0.88514 | −1.44282 |
| H | −3.17979 | 0.83008 | 0.67248 |
| H | 2.74731 | 1.18103 | −1.40316 |
| H | 3.08420 | 1.07842 | 0.71276 |

Electronic Energy = −2518.60453821
Sum of electronic and thermal Energies = −2518.391616
Sum of electronic and thermal Enthalpies = −2518.390672
Sum of electronic and thermal Free Energies = −2518.446116

DFT Calculations: Coordinates for Li[FeH$_2$(CO)(PH$_2$CH$_2$CH$_2$N(AlH$_3$)CH$_2$CH$_2$PH$_2$)] (Model of Compounds 6b; See FIG. 9A):

| Fe | −0.64232 | 0.39347 | −0.00739 |
|---|---|---|---|
| H | −0.31074 | 1.46348 | 1.09604 |
| H | −0.29602 | 1.43344 | −1.13612 |
| P | −0.72942 | −1.13867 | −1.61558 |
| H | −1.05748 | −0.78729 | −2.94396 |
| H | −1.47121 | −2.34205 | −1.53194 |
| P | −0.74632 | −1.07025 | 1.65952 |
| H | −1.01712 | −0.64929 | 2.98038 |
| H | −1.53015 | −2.24914 | 1.65160 |
| C | −2.30716 | 0.93939 | −0.02911 |
| O | −3.40041 | 1.33393 | −0.04605 |
| C | 0.98646 | −1.70829 | 1.73762 |
| H | 1.26347 | −2.03048 | 2.74798 |
| H | 1.04015 | −2.58485 | 1.07914 |
| C | 1.02262 | −1.72290 | −1.72520 |
| H | 1.28812 | −2.03002 | −2.74324 |
| H | 1.12388 | −2.60070 | −1.07442 |
| C | 1.87153 | −0.57047 | 1.23439 |
| H | 2.90162 | −0.93076 | 1.08672 |
| H | 1.92082 | 0.19958 | 2.02028 |
| C | 1.87965 | −0.55959 | −1.23394 |
| H | 2.92118 | −0.88918 | −1.09412 |
| H | 1.90002 | 0.20973 | −2.02112 |
| N | 1.38475 | 0.06076 | 0.00122 |
| H | 2.20292 | 2.47366 | −1.24969 |
| H | 2.18376 | 2.48351 | 1.24953 |
| Al | 1.15958 | 2.02865 | −0.00631 |
| H | 0.52777 | 3.64552 | −0.01930 |
| Li | 2.32079 | 4.11671 | −0.00849 |

Electronic Energy = −2526.538617
Sum of electronic and thermal Energies = −2526.522415
Sum of electronic and thermal Enthalpies = −2526.521471
Sum of electronic and thermal Free Energies = −2526.581234

General Procedure for the Synthesis of Complex 9: While it was found that base was required for catalysis (see [00118]), methoxide hydride complexes 7b were unstable in base when a substrate and hydrogen was absent. When KOtBu was added to a $C_6H_6$ solution of prepared pre-catalyst 7b, the orange solution turned red after stirring for 10 min. After removal of a white precipitate, a $^{31}P\{^1H\}$ NMR ($C_6D_6$) spectrum of the isolated red residue showed one major compound as two doublets at 79.7 and 101 ppm ($J_{PP}$=73.0 Hz), along with minor compounds and free P—$CH_2$NH—P' ligand. Once crystals suitable for X-ray diffraction were isolated by slow diffusion of pentane into the $C_6D_6$ solution, the major compound was identified to be a neutral Fe(0) complex: Fe(Ph$_2$PCH$_2$CH$_2$NHCH$_2$CH$_2$P$^i$Pr$_2$)(CO)$_2$, 9:

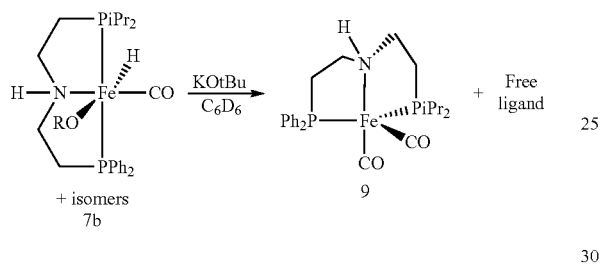

FIG. 9B depicts the ORTEP plot of 9 (thermal ellipsoids at 30% probability), wherein hydrogen atoms of phenyl and iso-propyl substituents were removed for clarity, and selected bond lengths (Å) and angles (°) included Fe(1)-C (6): 1.723(2); Fe(1)-C(5): 1.797(2); Fe(1)-N(1): 2.088(2); Fe(1)-P(2): 2.1735(6); Fe(1)-P(1): 2.2038(6); C(6)-Fe(1)-C (5): 93.94(9); C(6)-Fe(1)-N(1): 172.41(9); C(5)-Fe(1)-N(1): 93.07(8); C(6)-Fe(1)-P(2): 89.62(7); C(5)-Fe(1)-P(2): 120.34(6); C(5)-Fe(1)-P(1): 119.37(6); P(2)-Fe(1)-P(1): 119.55(2); N(1)-Fe(1)-P(2): 84.34(5); C(6)-Fe(1)-P(1): 95.00(7).

Discussion

Synthesis of hydride-aluminumhydride iron complexes 5a-d, 6a-d and monohydride complexes 7b (R''' Me) and 8b and (S,S)-8d (R''' tAmyl) began with purple THF solutions of 4a-d, which turned immediately dark brown and evolved gas upon addition of a LiAlH$_4$ activator:

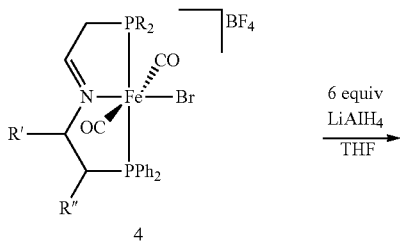

a) R = Cy; R', R'' = H
b & b-$^{13}$CO) R = iPr; R', R'' = H
c) R = Ph; R', R'' = H
(S,S)-d) R = Cy; R'' = Me; R' = Ph

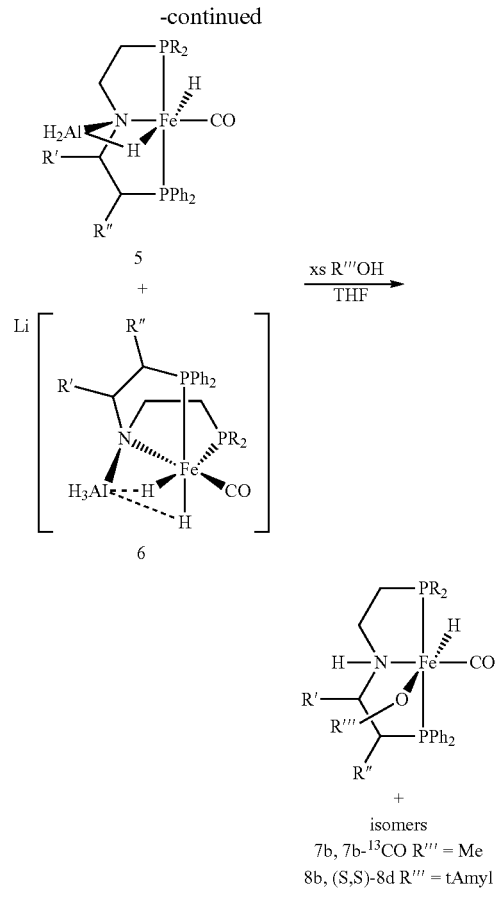

7b, 7b-$^{13}$CO R''' = Me
8b, (S,S)-8d R''' = tAmyl

Removal of THF and subsequent removal of a black precipitate with Et$_2$O afforded a dark brown-yellow solution. The isolated residue was examined by NMR spectroscopy and found to contain two iron hydride-aluminumhydride species with either trans hydrogens with a mer-P—N—P' ligand on iron (5a-d), or cis hydrogens with a fac-P—N—P' ligand on iron (6a-d) as shown above. For example, 5b was thought to have a mer configuration because it had a large $J_{PP}$ of 105 Hz, while 6b was thought to be fac with a small $J_{PP}$ of 20 Hz. Since no proton source was added to the reaction, it was postulated that Al was still bound to the amide as AlH$_3$. $^{27}$Al NMR spectroscopy supported this postulate, since it displayed a large broad signal at 100 ppm; as did IR spectroscopy, which had vAl-H absorptions at 1783 and 1648 cm$^{-1}$ [Ares, J. R.; Aguey-Zinsou, K. F.; Porcu, M.; Sykes, J. M.; Dornheim, M.; Klassen, T.; Bormann, R. Mater. Res. Bull. 2008, 43, 1263-1275]. Compound H$_2$Al[N(CH$_2$CH$_2$NMe$_2$)$_2$]AlH$_3$ provided a precedent for such an alane-amide adduct [Luo, B.; Kucera, B. E.; Gladfelter, W. L. Dalton Trans. 2006, 0, 4491-4498]. It was considered that there were up to two configurations of structures 5 (H trans to H, and H trans to N); however, only trans is the major structure, as drawn. For structures 6, there was only one configuration and its enantiomer for 6a and 6b, and only one for 6c (no enantiomer), but there were two diastereomers for (S,S)-6d with the nitrogen in a R or S configuration. Chemical shifts, coupling constants, as well as DFT calculations (see above), were used to support the tentative structures of iron hydride species 5 and 6, as shown above.

For the DFT analysis of structures 5 and 6, simplified structures were employed, wherein hydrogen replaced substituents on phosphorus, as shown in FIGS. 8 (for hydride-aluminumhydrides 5) and 9 (for 6). Trans hydride-aluminumhydrides had Fe—H distances of 1.54 and 1.66 Å, the latter due to an interaction with aluminum. Interaction of the hydride with quadrupolar aluminum at Al—H 1.73 Å explained the broadening of the corresponding hydride resonance at −10.9 ppm in the $^1$H NMR spectrum of 5b. Cis hydride-aluminumhydrides of complexes 6 had Fe—H distances of 1.57 Å, and those hydrogens were at longer distances from aluminum (Al—H 1.92, 1.94 Å), which explained why those resonances were not as broad and appeared as pseudo AA'XX' patterns in the region −11 to −12 ppm due to the arrangement of similar hydride environments and phosphorus environments in an approximately square plane around the octahedron of iron. Li+ was calculated as ion-paired to AlH$_3$ unit, but in THF solution it might have also had a THF coordinated; as noted, Li+ was detected by NMR.

One observation was that complexes 5c and 6c formed from starting complex 4c contained symmetrical PPh$_2$CH$_2$CH$_2$NCH$_2$CH$_2$PPh$_2$ ligands. This was apparent from a $^{31}$P{$^1$H} NMR spectrum where 5c and 6c gave singlets due to equivalent phosphorus nuclei (see FIG. 11). This was considered evidence that the imine group was being reduced in complexes 4a-d during catalyst activation.

It was observed that catalytic hydrogenation activity may depend on the nature of the alcohol used, and as such, treatment of the iron hydride aluminumhydride complexes with MeOH and tAmylOH were separately examined by NMR. Upon addition of an excess of alcohol to a C$_6$H$_6$ or THF solution of complexes 5 and 6, iron pre-catalysts mer Fe(H)(OR''')(CO)(P—CH$_2$NH—P') (7 with R'''=Me; 8 with tAmyl) were formed (see [00141]). The solution's color changed from yellow to orange along with gas evolution. NMR spectra of the isolated residues showed multiple iron hydride complexes with similar patterns; however, they were iron mono-hydride complexes. $^1$H, $^{31}$P and $^{13}$C NMR spectra of complexes 7b, 7b-$^{13}$CO, 8b and (S,S)-8d were examined in detail to distinguish differences between reaction with MeOH as compared with that of $^t$AmylOH (see paragraph [00134]). $^{31}$P{$^1$H} NMR spectrum demonstrated that there was no dissociation of the P—N—P' ligands and that there was downfield shift of the phosphorus resonances for solutions of 8 versus solutions of 7, thus providing evidence for an alkoxide ligand. Major iron monohydride compounds were postulated to have a mer structure with trans phosphorus groups of the P—N—P' ligand, since $^2J_{PP}$ were in a range of 120-150 Hz. $^2J_{HP}$ values of the $^1$H NMR spectrum hydride resonances were greater than 50 Hz, which was also consistent with structures with hydrides cis to phosphorus (see [00134]). $^1$H—$^{31}$P HMBC NMR spectrum enabled correlation of hydride resonances to appropriate phosphorus resonances for 7b, 7b-$^{13}$CO and (S,S)-8d. $^1$H-$^{13}$C HMBC NMR spectrum of 7b-$^{13}$CO showed unique correlations for each hydride to one CO ligand.

It was considered, therefore, that each isomer had a mer-configuration with one P—NH—P', hydride, alkoxide and carbonyl ligand. Trans positions for the monodentate ligands were inequivalent because of the NH group's position. Consequently, it was determined that the total number of possible methoxide isomers were: six for 7a and 7b (and six enantiomers), three for 7c and six for (S,S)-7d. $^t$Amyl derivatives of 8 had the same numbers of isomers (see DFT analysis below).

Additionally, relative ratios of various hydride species 7b appeared to vary slightly depending on exact reaction conditions: use of slightly less alcohol appeared to favour formation of hydride species with $^1$H NMR signals at −18.6 ppm (see [00134]); whereas use of excess alcohol yielded much less of the −18.6 ppm hydride species, and a new species with $^1$H NMR hydride signals at −22.7 ppm. Existence of a separate species which did not correlate to any hydrides was also detected, and was assigned as zero-valent Fe(CO)$_2$(P—CH$_2$NH—P') complex 9 with $^{31}$P{$^1$H} doublets at 101.0 and 79.7 ppm with J$_{PP}$ of 73 Hz. Formation of this complex was associated with presence of base (see [00139]), in this case LiOH, which was likely produced by hydrides reacting with traces of water in the solvents. The presence of this complex showed that ligand redistribution reactions were possible. Over a period of 24-48 hours, the hydride signals at −18.6 ppm, and all minor hydride species, disappeared, leaving a spectrum with only two hydride species at −21.6 and −22.7 in a 1:1 ratio. $^1$H—$^{31}$P HMBC and $^1$H-$^{13}$C HMBC enabled correlation of the hydride to other nuclei for each isomer. The −21.6 ppm hydride was a doublet of doublets with J$_{HP}$=52 and 57 Hz, and correlated to a $^{31}$P doublet of doublets at 94.8 and 75.3 ppm, with J$_{PH}$=30 and J$_{PP}$=137 Hz. This hydride was also correlated to $^{13}$C{$^1$H} NMR signals at 222.8 ppm for CO, 139.7 ppm for P—C(Ph) and 24.5 ppm for PC(iPr). Similarly, the −22.7 ppm hydride was a doublet of doublets with J$_{HP}$=52 and 56 Hz, and correlated to a $^{31}$P doublet of doublets at 95.7 and 75.0 ppm, with J$_{PH}$=21 and J$_{PP}$=136 Hz, and $^{13}$C{$^1$H} NMR signals at 222.4 ppm for CO, 139.5 ppm for P—C(Ph) and 24.6 ppm for P—C(iPr). These species were quite similar, and were known to be mono-hydride, mono-carbonyl, iron PNP species, and thus were proposed to be mer-Fe(H)(OMe)(CO)(P—CH$_2$NH—P'), with N—H up and down, relative to the hydride for each isomer, respectively. The −21.6 ppm hydride was therefore considered to be a kinetic product, and the −22.7 ppm hydride, a thermodynamic product.

A labeled alcohol, $^{13}$CH$_3$OH, was utilized to prepare 7b in order to verify the presence of the methoxide ligand. However, only free $^{13}$CH$_3$OH resonance was detected; this was likely due to a dynamic averaging of the methoxide and methanol resonances, since alkoxide ligands usually hydrogen-bond to an alcohol as hydrogen-bonded anions [ROH—OR]$^-$ [Clapham, S. E.; Guo, R.; Zimmer-De luliis, M.; Rasool, N.; Lough, A.; Morris, R. H. *Organometallics* 2006, 25, 5477-548681; Baratta, W.; Ballico, M.; Esposito, G.; Rigo, P. *Chem. Eur. J.* 2008, 14, 5588-5595]. No enhancement of the Fe—$_{13}$CO signals were detected, and this showed that isomers of 7b and any 9 present did not contain carbonyl ligands derived from the alcohol [Zhang, J.; Gandelman, M.; Shimon, L. J. W.; Rozenberg, H.; Milstein, D. *Organometallics* 2004, 23, 4026-4033; Kloek, S. M.; Heinekey, D. M.; Goldberg, K. I. *Organometallics* 2006, 25, 3007-3011].

Preformed solutions of 7b containing only the two hydride isomers at −21.6 and −22.7 ppm were tested for hydrogenation of acetophenone to 1-phenylethanol under 5 atm H$_2$ pressure and 50° C., as optimized. These solutions were active, converting 1000 equivalents of substrate in less than 15 minutes, but only in the presence of base.

A mixture of hydride complexes 8b without contamination by complex 9 was also tested for acetophenone hydrogenation at 50° C. and 25 atm H$_2$, in THF, in the presence of base (KOtBu). Full conversion of acetophenone to 1-phenylethanol occurred in 10 min with 0.2 mol % catalyst loading based on initial amounts of 4b used to synthesize 8b.

¹H NMR hydride resonances of alkoxide species 7 and 8 (see [00134]) were found to be similar in chemical shift and coupling constant to those of Fe{2,6-(PiPr$_2$CH$_2$)$_2$C$_5$H$_3$N}(H)(CO)(O$^i$Pr), as reported by Milstein et al. [Langer, R.; Leitus, G.; Ben-David, Y.; Milstein, D. *Angew. Chem. Int. Ed.* 2011, 50, 2120-2124]. The latter displayed a triplet hydride resonance at −19.5 ppm with J$_{HP}$=53.5, however, and was thought to be a catalytically active form of precatalyst M2 (FIG. 1).

Chiral complex (S,S)-8d also existed as a mixture of iron mono-hydride compounds with two major isomers (see [00134]). Again, large $^2$J$_{PP}$ indicated trans phosphine coordination of the P—CH$_2$N—P' ligand, while the large $^2$J$_{HP}$ indicated cis hydride and phosphine ligands; however, phosphorus chemicals shifts of these minor compounds were only identified via a ¹H—³¹P HMBC spectrum, implying they were in low concentration relative to the two major isomers of (S,S)-8d (see [00135]). Despite these complexes existing as a mixture of isomers, they were active for ketone hydrogenation and, for (S,S)-8d, had good enantioselectivity. For example, the mixture of hydrides catalyzed acetophenone hydrogenation to 1-phenylethanol with same e.e. and activity as precatalyst (S,S)-4d activated in situ:

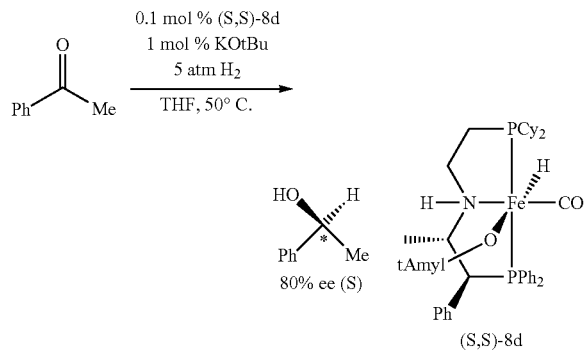

Example 4

Properties of Isomeric Alkoxide Hydrides (S,S)-7d as Determined by DFT Analysis

Experimental

Density Functional Theory Calculations on Simplified Models of (S,S)-7d:

DFT calculations were performed using Gaussian 09 [Frisch, M. J. et al., 2009, Gaussian 2009 Revision B. 2001]. M06 hybrid functional was used for all calculations [Zhao, Y.; Truhlar, D. *Theor. Chem. Acc* 2008, 120, 215-241; Zhao, Y.; Truhlar, D. G. *Acc. Chem. Res.* 2008, 41, 157-167]. All atoms were treated with a 6-31++G(d,p) basis set. A pruned (99,590) integration grid was used throughout (Grid=UltraFine). Optimizations were performed in tetrahydrofuran using an integral equation formalism polarizable continuum model (IEF-PCM) with radii and nonelectrostatic terms from a SMD solvation model [Marenich, A. V.; Cramer, C. J.; Truhlar, D. G. *J. Phys. Chem. B* 2009, 113, 6378-6396]. Full vibrational and thermochemical analyses (1 atm, 298 K) were performed on optimized structures to obtain solvent-corrected free energies (G°) and enthalpies (H°). Optimized ground states were found to have zero imaginary frequencies. DFT gas phase calculations on full structures of (S,S)-7d isomers were performed using GAMESS [GAMESS, http://www.msg.chem.iastate.edu/GAMESS/GAMESS.html; Schmidt, M. W.; Baldridge, K. K.; Boatz, J. A.; Elbert, S. T.; Gordon, M. S.; Jensen, J. H.; S. Koseki; Matsunaga, N.; Nguyen, K. A.; Su, S. J.; Windus, T. L.; Dupuis, M.; Montgomery, J. A. *J. Comput. Chem.*, 1993, 14, 1347]. M06 functional was used. Iron was treated with a LANL2DZ basis set with an effective core potential [Hay, P. J.; Wadt, W. R. *J. Chem. Phys.* 1985, 82, 270; ibid 284; ibid 299]. Atoms C, H, N, O and P were treated with the 6-31 G basis set (see FIG. 10A).

Exemplary Density Functional Theory (Gaussian09 M06/6-31++G(d,p)/(IEF-PCM)SMD(THF) Results for Most Stable Simplified Model of (S,S)-7d, F, with trans-(H) (OCH$_3$) and OCH$_3$ Adjacent to N—H (See FIGS. 12A and 12B):

| Fe—H = 1.55, Fe—C = 1.69, Fe—O = 1.99, Fe—N = 2.07, Fe—P (PPh$_2$) = 2.23, Fe—P (PCy$_2$) = 2.24 | | |
|---|---|---|
| E° = E° = −4.27 | | |
| P | 1.053961924 | 6.841949243 | 3.001709621 |
| C | 2.112154031 | 6.057059832 | 1.655127439 |
| C | −0.131475517 | 4.622694905 | 4.234792446 |
| C | −2.510911004 | 4.592872861 | 5.064409655 |
| H | 2.426760151 | 9.450264617 | 3.363165397 |
| H | −0.513552431 | 8.237420162 | 1.609168999 |
| H | 3.542685842 | 14.108051198 | 8.158213181 |
| N | 1.579231202 | 9.548526753 | 3.956127233 |
| C | 4.020971388 | 10.112900077 | 8.616009164 |
| C | −0.732072234 | 7.550466756 | 9.201333598 |
| C | 0.622573153 | 12.732966169 | 9.220416398 |
| C | 1.358344348 | 7.059215394 | 10.301275969 |
| H | −2.208297916 | 5.024187163 | 6.032741458 |
| C | 6.308706413 | 10.677484815 | 8.075675580 |
| C | 1.282662711 | 10.483429811 | 6.233975702 |
| H | −1.092427635 | 2.952525078 | 5.220458709 |
| C | 1.427423479 | 11.598272638 | 7.223600171 |
| C | 2.692454550 | 6.284005362 | 5.414121334 |
| C | 2.533345382 | 12.464211505 | 7.212891431 |
| H | −0.124810677 | 12.831531480 | 10.002803214 |
| H | 0.230245672 | 10.168901158 | 6.174806345 |
| H | −0.575293573 | 6.571164049 | 11.116848498 |
| C | 6.145015448 | 10.135491359 | 6.800458434 |
| H | 1.838364116 | 14.358384166 | 9.952345008 |
| H | −1.904676308 | 7.394970802 | 3.097677257 |
| H | −3.392806127 | 3.966217102 | 5.253820657 |
| H | 4.296950454 | 3.374467988 | 1.389501768 |
| H | −3.667336999 | 6.346505084 | 4.499345468 |
| Fe | 2.032349009 | 7.718291014 | 4.814998601 |
| C | −1.631175201 | 6.598218861 | 3.804576828 |
| O | 3.269025490 | 5.305986734 | 5.775479194 |
| H | 2.877977126 | 10.882799765 | 4.856535339 |
| C | 2.053983367 | 7.643573434 | 9.241067400 |
| H | 0.227005259 | 5.068752524 | 5.177102714 |
| H | 1.504582186 | 12.910024851 | 4.810851751 |
| H | 0.195635191 | 10.475359858 | 2.607822865 |
| H | −1.679372746 | 3.256565097 | 3.582361224 |
| H | 2.399777645 | 3.257435834 | −0.209186769 |
| C | 1.184525455 | 12.042234859 | 4.225741576 |
| C | 5.370002982 | 11.097770328 | 9.972546024 |
| C | 0.339537045 | 9.526031487 | 3.139144681 |
| C | 2.380475633 | 5.349744532 | −0.745465291 |
| H | 3.858062403 | 3.787340121 | −1.053335372 |
| H | 7.262849077 | 11.110647955 | 8.364287464 |
| H | 1.514159973 | 12.194876356 | 3.190741624 |
| C | −0.037797625 | 8.123002218 | 8.137867177 |
| C | −1.358428069 | 3.750774108 | 4.514950877 |
| H | 0.602487747 | 7.653702417 | 5.408598050 |
| C | 3.121246359 | 4.086556369 | −0.295724879 |
| C | 1.782473779 | 10.769798411 | 4.814168289 |
| P | 2.249810873 | 8.891273357 | 6.695933267 |
| H | 3.309193368 | 12.346682839 | 6.458873855 |
| C | 4.921693229 | 9.573483210 | 6.430607001 |
| C | 3.855513305 | 9.562501974 | 7.339288178 |
| H | −0.514499036 | 9.379218857 | 3.812443905 |

-continued

| Fe—H = 1.55, Fe—C = 1.69, Fe—O = 1.99, Fe—N = 2.07, Fe—P (PPh₂) = 2.23, Fe—P (PCy₂) = 2.24 | | | |
|---|---|---|---|
| H | 0.869651268 | 6.732003195 | -0.014173961 |
| H | -3.227770183 | 5.293172401 | 3.151498033 |
| C | -0.468341296 | 5.760781393 | 3.258999961 |
| C | 2.675664275 | 13.453434353 | 8.183397914 |
| H | -0.382943903 | 11.082428857 | 8.269229516 |
| H | 6.969671189 | 10.145864486 | 6.093104575 |
| H | 1.908628588 | 6.629548233 | 11.133620889 |
| H | -0.756758478 | 5.336771668 | 2.280736621 |
| H | -1.817519574 | 7.505123000 | 9.175651122 |
| H | 3.265503735 | 4.885735479 | 3.092766949 |
| C | 1.387614708 | 5.823315344 | 0.325170396 |
| H | 3.111901885 | 6.153331577 | -0.928717448 |
| H | 4.753675037 | 9.164129207 | 5.433648964 |
| H | 3.141093076 | 7.657459990 | 9.253604437 |
| H | 2.020926695 | 3.973816480 | 2.227313997 |
| H | 1.196347818 | 8.644996069 | 1.368266100 |
| C | -0.034518588 | 7.022495568 | 10.289717466 |
| H | 4.586938563 | 5.064477980 | 0.962273508 |
| C | 0.475259838 | 11.750837820 | 8.242397182 |
| H | 3.187046427 | 10.135827571 | 9.315534912 |
| H | 1.857369485 | 5.170593871 | -1.694656400 |
| C | 3.801376635 | 4.297244787 | 1.060379889 |
| C | 1.723279478 | 13.590118159 | 9.193020773 |
| H | 0.692931465 | 4.008288964 | 3.849663540 |
| C | -2.855764372 | 5.725457917 | 4.095799522 |
| H | -1.291215856 | 7.087015012 | 4.732892303 |
| H | 2.890843202 | 6.829108429 | 1.518998447 |
| C | 0.439973622 | 8.395092981 | 2.126205099 |
| C | 5.247282376 | 10.665829246 | 8.982956931 |
| H | 0.087416465 | 12.023352526 | 4.248480860 |
| H | 0.617010760 | 5.047554393 | 0.469146723 |
| C | 1.360056275 | 8.191985291 | 8.159001506 |
| H | -0.579563606 | 8.482624658 | 7.265580560 |
| C | 2.787269973 | 4.758527213 | 2.112557565 |
| O | 3.648671068 | 8.266154852 | 3.782180906 |
| C | 4.813963366 | 7.494598076 | 3.573375210 |
| H | 5.585630632 | 8.110393053 | 3.083926992 |
| H | 4.646127595 | 6.613882898 | 2.924523300 |
| H | 5.241795145 | 7.110596395 | 4.517546369 |
| ΔG$_{solv}$ = -1598206.011 | | | |
| 15 | 1.956664205 | 0.909695829 | -0.244427984 |
| 1 | -0.509220565 | 1.018241026 | 1.400760050 |
| 1 | 1.516924320 | 3.338436518 | -0.406725669 |
| 6 | -2.758857899 | -0.127532876 | -0.632552046 |
| 6 | 1.380740116 | -1.867281559 | -0.702249595 |
| 1 | -2.518394899 | 0.350204697 | -1.595855710 |
| 26 | 0.339395174 | -0.575272720 | -0.193269099 |
| 8 | 2.099002101 | -2.710513509 | -1.072723798 |
| 1 | -2.456950864 | 0.230115279 | 1.443448641 |
| 1 | -4.197662030 | 1.794784710 | 0.856773231 |
| 6 | -3.163583671 | 2.057623477 | 0.609222203 |
| 1 | -2.800052347 | 2.717820372 | 1.405643202 |
| 1 | 0.117422387 | -0.200247793 | -1.689235889 |
| 6 | -2.322947642 | 0.797721267 | 0.506216071 |
| 1 | 1.213049317 | 2.687458563 | 1.214442450 |
| 6 | 1.081374920 | 2.492690463 | 0.139639974 |
| 1 | -3.179309676 | 2.620701086 | -0.333396500 |
| 8 | 0.445411592 | -0.734136435 | 1.797850006 |
| 6 | 1.018279455 | -1.856644551 | 2.337169064 |
| 1 | 0.978508684 | -1.838212546 | 3.445898040 |
| 1 | 2.094743176 | -1.987198997 | 2.072645909 |
| 1 | 0.520308348 | -2.805466566 | 2.026860023 |
| 15 | -1.607387837 | -1.573108455 | -0.480385441 |
| 1 | -2.289551679 | -2.325577473 | 0.519504026 |
| 1 | -1.940876118 | -2.365161831 | -1.602561376 |
| 6 | 3.323052161 | 0.816087194 | 0.962922493 |
| 1 | 3.977803039 | -0.022537699 | 0.694999189 |
| 1 | 3.915153517 | 1.739733718 | 0.979734253 |
| 1 | 2.902196426 | 0.625412307 | 1.956558968 |
| 6 | 2.823621468 | 1.226597800 | -1.820515202 |
| 1 | 3.565565611 | 2.028463112 | -1.717689829 |
| 1 | 3.329810384 | 0.310025913 | -2.147964220 |
| 1 | 2.091533261 | 1.503134072 | -2.587783763 |
| 6 | -4.228087463 | -0.509071248 | -0.583421113 |
| 1 | -4.502883974 | -0.885225043 | 0.412267417 |
| 1 | -4.880477115 | 0.342469155 | -0.813793825 |
| 1 | -4.452865971 | -1.298501261 | -1.310680075 |
| 6 | -0.397334398 | 2.320362495 | -0.170783598 |
| 1 | -0.575381175 | 2.277546711 | -1.253720378 |
| 1 | -0.956862260 | 3.176650893 | 0.228133791 |
| 7 | -0.845543094 | 1.047013706 | 0.432005262 |

Discussion

To support structural assignments for all alkoxides investigated, relative stabilities of said possible isomers were analyzed by DFT studies. An initial study utilized a large basis set to treat simplified structures of the methoxide isomers where phenyls on phosphorus were replaced with hydrogen, and where cyclohexyl groups and backbone phenyls were replaced with methyl groups. This study was designed to reveal electronically preferred isomers with the mer-P—NH—P' ligand stereochemistry that was established by NMR studies. Of the six possible diastereomers, two isomers with hydride trans to carbonyl were found to be high in energy, and thus too unstable to form (see paragraph [00154]). The isomer with a hydride trans to methoxide, and with methoxide next to NH was most stable.

Steric effects on relative stabilities of the isomers was explored using a gas phase calculation of the full structures treated with a smaller basis set (see FIG. 10). There were four diastereomers that were low in energy with isomer F being most stable. The methoxide oxygen was within hydrogen-bonding distance of N—H group (O—H: 1.75 Å).

Example 5

Examination of the Mechanism of Activation via Dihydride Complexes

Described below are investigations using NMR spectroscopy and DFT calculations to determine structures and/or characteristics of the active hydride species present during catalyst activation and catalysis using complexes 7b, or (S,S)-7d for ketone hydrogenation. Early in these studies, hydride resonances were observed in the $^1$H NMR spectrum that were similar to previously known trans dihydride complexes [Langer, R.; Iron, M. A.; Konstantinovski, L.; Diskin-Posner, Y.; Leitus, G.; Ben-David, Y.; Milstein, D. Chem.—Eur. J. 2012, 18, 7196-7209], and so a more detailed examination of the mechanism of activation and catalysis was pursued.

General Experimental

All procedures and manipulations were performed under an argon or nitrogen atmosphere using standard Schlenk-line and glove box techniques unless stated otherwise. All solvents were degassed and dried using standard procedures prior to all manipulations and reactions unless stated otherwise. Deuterated solvents were purchased from Cambridge Isotope Laboratories or Sigma Aldrich, degassed, and dried over activated molecular sieves prior to use. All other reagents were purchased from commercial sources and utilized without further purification. NMR spectra were recorded at ambient temperature and pressure using a Varian Gemini 400 MHz spectrometer (400 MHz for 1H, 100 MHz for $^{13}$C, 376 MHz for $^{19}$F, and 161 MHz for $^{31}$P), or an Agilent DD2-600 MHz spectrometer (600 MHz for $^1$H, 151 MHz for $^{13}$C, 564 MHz for $^{19}$F, and 243 MHz for $^{31}$P) unless stated otherwise. $^1$H and $^{13}$C NMR were measured relative to partially deuterated solvent peaks, but were reported relative to tetramethylsilane (TMS). All $^{31}$P chemical shifts were measured relative to 85% phosphoric acid as an external reference. Gas Chromatography was done on a Perkin Elmer Clarus 400 Chromatograph equipped with a chiral column (CP chirasil-Dex CB 25 m×2.5 mm) to determine substrate conversion and enantiopurity. Hydrogen gas was used as the mobile phase, and the oven temperature was set at 130° C. Retention times for phenylethanol were 7.58 and 8.03 minutes, and for acetophenone, 4.56 minutes. All hydrogenation reactions were performed in a 50 mL stainless steel Parr Hydrogenation reactor at constant temperatures and pressures. Temperature was maintained at 50° C. using a constant temperature water bath and was purged of oxygen by flushing the reactor several times with 5 atm of $H_2$ (g).

Synthesis of Precatalysts: Iron precatalysts mer-trans-[Fe(Br)(CO)$_2$(P—CH=N—P')][BF$_4$] were generated according to the foregoing procedure (see, for example, paragraph [00100]; as were alkoxide mono-hydride complexes FeH(OR')(CO)(P—CH$_2$NH—P') (7b and (S,S)-7d; see above).

Synthesis of trans-dihydride complex (11a-b/12a-b): Following the preparation of alkoxide mono-hydride complexes FeH(OR')(CO)(P—CH$_2$NH—P') (7b and (S,S)-7d), a THF-d$_8$ solution (0.6 mL) of the respective alkoxide mono-hydride complexes was transferred to a Schlenk flask and reacted with 1 atm hydrogen. After stirring under $H_2$ (g) for 5 minutes, base (~8 mg) was added in THF-d$_8$ (0.3 mL) under $H_{2\,(g)}$. Bases used included KOtBu, NaOtBu, Ph-CH(OK)CH$_3$, and NaOMe; however, it was found that NaOMe was not an effective base, and KOtBu was primarily used throughout testing. Upon addition of base, the bright orange solution rapidly turns bright pink, then dark green/brown over 30 minutes. The solution was then injected into an NMR tube filled with $H_2$ (g) and the resonances due to the dihydrides were observed using $^{31}$P and $^1$H NMR spectroscopy.

NMR data for a mixture of trans-dihydride 11a and cis-dihydride 12a in a 9:1 ratio. 11a: $^{31}$P{$^1$H} NMR (THF-d$_8$) 118.0 (d) and 95.8 ppm (d, J$_{PP}$(trans) 118 Hz). $^1$H NMR (THF-d$_8$) −9.05 and −9.16 ppm (AB part of ABXY pattern, $^2$J$_{HH}$=J$_{AB}$=9.8 Hz, $^2$J$_{PP}$(trans)=J$_{XY}$=118.0 Hz, and $^2$J$_{HP}$(cis) (J$_{AX}$, J$_{AY}$, J$_{BX}$, J$_{BY}$)=42.0, 42.0, 43.0, and 43.0 Hz. 12a: $^{31}$P{$^1$H} NMR (THF-d$_8$) 114.5 (d) and 93.0 ppm (d, J$_{PP}$ 90 Hz)$^1$H NMR (THF-d$_8$) −8.1 ppm (m) and −20.6 ppm (m).

NMR data for mixture of trans-dihydride 11b and cis-dihydride 12b in a 1:1 ratio. 11b: $^{31}$P{$^1$H} NMR (THF-d$_8$) 110.2 (d) and 106.5 ppm (d, J$_{PP}$ 113.6 Hz). $^1$H NMR (THF-d$_8$) −8.56 and −8.94 ppm (m, AB part of ABXY pattern). 12b: $^{31}$P{$^1$H} NMR (THF-d$_8$) 102.5 (d) and 109.7 ppm (d, J$_{PP}$(trans) 116.4 Hz). $^1$H NMR (THF-d$_8$) −7.31 ppm (m) and −21.00 ppm (m).

To further remove excess base, benzene (3 mL) was added to the solution in a vial in a nitrogen filled glovebox. The solution was then filtered through Celite and dried. To the dried solution, THF-d$_8$ (0.7 mL) was added and further stirred under $H_2$ (g) for 10 minutes and gave resolved $^1$H NMR spectra consistent with the analysis reported above.

Hydrogenation studies with preformed dihydride catalyst systems: Stock solutions of acetophenone (0.3 mL, 2.6 mmol) in THF (7 mL) were injected into Parr reactors heated to 50° C. and pressurized to 5 atm $H_2$ (g) against a flow of hydrogen. 12-inch needles equipped with 1 mL syringes were used to remove THF-d$_8$ solutions of the dihydrides 11a-b/12a-b from rubber-septum capped NMR tubes prepared as outlined above, and injected into the reactors against a flow of hydrogen. At set times, small amounts of sample were removed from the reactor using a needle and syringe under a flow of hydrogen and injected into the gas chromatograph for analysis.

Hydrogenation studies with in-situ generated systems: In an argon filled glovebox, a vial was charged with [Fe(CO)$_2$(Br)(PNP')][BF4] (4b, (S,S)-4d) (5 mg, 0.006 mmol) and 3 mL THF. To this solution, LiAlH4 in THF (0.05 mL of 1.0 M solution) was added, after which the solution's color immediately changed from pink to dark brown. After stirring for 5 minutes, an alcohol (for example: 2-methyl-2-butanol) (0.5 mL) was added and the solution was allowed to stir for an additional 10 minutes. The solution was then transferred to a syringe equipped with a 12-inch needle. The same vial was then charged with acetophenone (0.35 mL, 3.0 mmol) and 3 mL THF. The solution was taken up into the same syringe that already contained the precatalyst solution and stoppered. In a second syringe equipped with a 12-inch needle, a solution of base (0.08 mmol of either KOtBu, NaOtBu, or NaOMe) in 3 mL THF was taken up and stoppered. Both syringes were removed from a glovebox and injected into Parr reactors heated to 50° C. and pressurized to 5 atm $H_2$ (g) against a flow of hydrogen. At set times, small amounts of sample were removed from the reactor using a needle and syringe under a flow of hydrogen, and injected into the gas chromatograph for analysis. As discussed below, complete conversion was observed in 15 minutes using either KO$^t$Bu or NaO$^t$Bu. Using NaOMe, however, no conversion to product alcohol was observed after 3 hours.

For experiments wherein cryptand was added to the catalyst system, a third syringe equipped with a 12-inch needle was charged with 2,2,2-cryptand (36 mg, 0.095 mmol) in 0.8 mL THF and stoppered. This solution was injected into the Parr reactor 2 minutes after the addition of the catalyst/acetophenone and base solutions. As discussed below, conversion to alcohol was complete in 15 minutes, as with the systems without cryptand; this suggested no interaction with cations during catalysis.

Computational Details: Density functional theory calculations were performed using Gaussian09 package [Frisch, M. J. 2010; Vol. Gaussian 09 Revision B.01] and M11-L hybrid functional [Peverati, R.; Truhlar, D. G. *J. Phys. Chem. Lett.* 2011, 3, 117-124; Kulkarni, A. D.; Truhlar, D. G. *J. Chem. Theory Comput.* 2011, 7, 2325; Zhao, Y.; Truhlar, D. *Theor. Chem. Acc.* 2008, 120, 215; d) Zhao, Y.; Truhlar, D. G. *J. Chem. Phys.* 2006, 125, 194101]. Functionals used for EDS calculation are provided in Table 3. All atoms were treated with a 6-31++G(d,p) basis set, which included diffuse basis functions, except for EDS calculations where a 6-31 G basis set was used [Clark, T.; Chandrasekhar, J.; Spitznagel, G. W.; Schleyer, P. V. R. *J. Comput. Chem.* 1983, 4, 294; Lynch, B. J.; Zhao, Y.; Truhlar, D. G. *J. Phys. Chem. A* 2003, 107, 1384; Frisch, M. J.; Pople, J. A.; Binkley, J. S. *J. Chem. Phys.* 1984, 80, 3265]. A pruned (99,590) integration grid was used throughout (Grid=UltraFine). Optimizations were performed using an integral equation formalism polarizable continuum model (IEF-PCM) [Tomasi, J.; Mennucci, B.; Cammi, R. *Chem. Rev.* 2005, 105, 2999; Tomasi, J.; Mennucci, B.; Cancès, E. *J. Mol. Struct. (THEOCHEM)* 1999, 464, 211] with radii and nonelectrostatic terms from a SMD solvation model in THF [Marenich, A. V.; Cramer, C. J.; Truhlar, D. G. *J. Phys. Chem. B* 2009, 113, 6378]. Ground states were connected to their transition states by performing intrinsic reaction coordinate (IRC) calculations [Fukui, K. *Acc. Chem. Res.* 1981, 14, 363]. Complex 13a and 16a were calculated in their singlet and triplet states for comparison (FIG. 13). Stationary points were characterized by normal-mode analysis. Full vibrational and thermochemical analyses (1 atm, 298 K) were performed on optimized structures to obtain solvent-corrected free energies (G°) and enthalpies (H°). Optimized ground states were found to have zero imaginary frequencies, while transition states were found to have one imaginary frequency. Three-dimensional visualizations of calculated structures were generated by ChemCraft.

Identification of Dihydride Species by NMR Spectroscopy

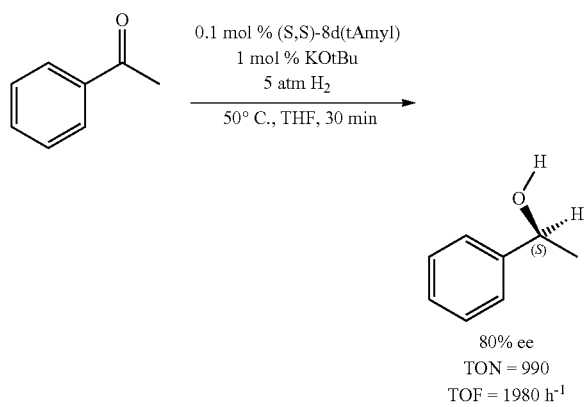

In view of the foregoing working examples, an objective was to identify what iron-containing species were formed when the precursor alkoxide complexes were activated with base to produce catalyst solutions for ketone hydrogenation (for example, see above scheme). Reaction of complex 7b with hydrogen in THF-$d_8$ without base yielded no change after 24 h. Addition of base (KOtBu or NaOMe) to 7b in the presence of hydrogen resulted in consumption of the starting material and formation of a new trans-dihydride species 11a, with $^{31}$P{$^1$H} NMR doublets at 118.0 and 95.8 ppm with a $J_{PP}$ 118 Hz, as well as with $^1$H NMR hydride signals centred at −9.10 ppm. In addition, there was a smaller amount (10%) of a cis-dihydride isomer 12a with doublets in its $^{31}$P{$^1$H} NMR spectrum at 114.5 and 93.0 ppm with $J_{PP}$ 90 Hz, along with complex triplets in its $^1$H NMR spectrum at −8.1 and −20.6 ppm which correlated by $^{31}$P-$^1$H HMBC (see below scheme).

Konstantinovski, L.; Diskin-Posner, Y.; Leitus, G.; Ben-David, Y.; Milstein, D. *Chem.—Eur. J.* 2012, 18, 7196-7209], with the difference being that the herein described trans complex had inequivalent hydrides. Selective decoupling of both the 118.0 and 95.8 ppm $^{31}$P signals associated with 11a resolved these signals into two hydride doublets at −9.05 and −9.16 ppm with $J_{HH}$ 9.8 Hz. The trans-hydrides were diastereotopic due to the presence of the amine group. Complexes with inequivalent trans-dihydrides are considered rare: trans-FeH$_2$(meso-tetraphos) has $J_{HH}$ 18 Hz [Bautista, M. T.; Earl, K. A.; Maltby, P. A.; Morris, R. H. *J. Am. Chem. Soc.* 1988, 110, 4056-4057; Bautista, M. T.; Earl, K. A.; Maltby, P. A.; Morris, R. H.; Schweitzer, C. T. *Can. J. Chem.* 1994, 72, 547-560], while cis dihydrides usually have $J_{HH}$ in a range of 13-21 Hz [Lagaditis, P. O.; Sues, P. E.; Sonnenberg, J. F.; Wan, K. Y.; Lough, A. J.; Morris, R. H. *J. Am. Chem. Soc.* 2014, 136, 1367-1380; Langer, R.; Iron, M. A.; Konstantinovski, L.; Diskin-Posner, Y.; Leitus, G.; Ben-David, Y.; Milstein, D. *Chem.—Eur. J.* 2012, 18, 7196-7209; Trovitch, R. J.; Lobkovsky, E.; Chirik, P. J. *Inorg. Chem.* 2006, 45, 7252-7260; Gusev, D. G.; Hubener, R.; Burger, P.; Orama, O.; Berke, H. *J. Am. Chem. Soc.* 1997, 119, 3716-3731; Schott, D.; Callaghan, P.; Dunne, J.; Duckett, S. B.; Godard, C.; Goicoechea, J. M.; Harvey, J. N.; Lowe, J. P.; Mawby, R. J.; Müller, G.; Perutz, R. N.; Poli, R.; Whittlesey, M. K. *Dalton Trans.* 2004, 3218-3224]; and, complex M (FIG. 14) in $C_6D_6$ had $J_{HH}$ 9.6 [Bornschein, C.; Werkmeister, S.; Wendt, B.; Jiao, H.; Alberico, E.; Baumann, W.; Junge, H.; Junge, K.; Beller, M. *Nat. Commun.* 2014, 5, doi 10.1038/ncomms5111; Chakraborty, S.; Brennessel, W. W.; Jones, W. D. *J. Am. Chem. Soc.* 2014, 136, 8564-8567]. The 118 Hz $J_{PP}$ of 11a was of similar magnitude to that of 7b ($J_{PP}$ 136 Hz), which had trans phosphorus nuclei in a mer P—N—P' configuration on the metal center [Lagaditis, P. O.; Sues, P. E.; Sonnenberg, J. F.; Wan, K. Y.; Lough, A. J.; Morris, R. H. *J. Am. Chem. Soc.* 2014, 136, 1367-1380], thus indicating that the ligand in 11a was also in a mer configuration, as shown in the above scheme. Simulation of the hydride's resonance pattern, using predicting software MestReNova 8, indicated that $J_{PH}$ coupling to the PiPr$_2$ and PPh$_2$ groups were 42 Hz, somewhat lower than the 50-60 Hz splitting observed for complexes 7b and (S,S)-7d but similar to the 40.3 Hz observed for dihydride J [Langer, R.; Iron, M. A.; Konstantinovski, L.; Diskin-Posner, Y.; Leitus, G.; Ben-David, Y.; Milstein, D. *Chem.—Eur. J.* 2012, 18, 7196-7209].

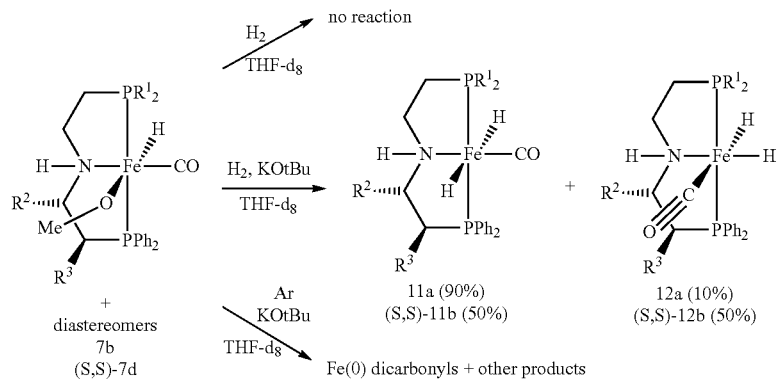

The trans-dihydride signals of 11a were similar to those of the corresponding isomers of dihydride J reported by Milstein and coworkers (see FIG. 14; Langer, R.; Iron, M. A.;

Reaction of chiral system (S,S)-7d in THF-$d_8$ with KOtBu under dihydrogen generated trans and cis dihydride isomers (S,S)-11b and (S,S)-12b, respectively, in an approximate 1:1 ratio. Dihydride (S,S)-11b had two doublets in its $^{31}$P NMR spectrum at 110.2 and 106.5 ppm, with $^2J_{PP}$=113.6 Hz for the trans phosphorus nuclei in a mer-(P—N—P') ligand. Two sets of hydride multiplet resonances were evident in its $^1$H NMR spectrum at −8.56 and −8.94 ppm with $^2J_{HH}$=9.3 Hz; these correlated with the 110.2 and 106.5 ppm $^{31}$P signals through $^1$H—$^{31}$P HMBC. $^{31}$P NMR spectrum of cis-(S,S)-12b had two doublets at 102.5 and 109.7 ppm with $^2J_{PP}$=116.4 Hz, with hydride multiplets appearing at −7.31 and −21.00 ppm with $^2J_{HH}$=15.5 Hz in the $^1$H NMR spectrum, similar to the cis-dihydride isomer of M [FIG. 14, Bornschein, C.; Werkmeister, S.; Wendt, B.; Jiao, H.; Alberico, E.; Baumann, W.; Junge, H.; Junge, K.; Beller, M. *Nat. Commun.* 2014, 5, doi 10.1038/ncomms5111; Chakraborty, S.; Brennessel, W. W.; Jones, W. D. *J. Am. Chem. Soc.* 2014, 136, 8564-8567].

Trans dihydrides J [Langer, R.; Leitus, G.; Ben-David, Y.; Milstein, D. *Angew. Chem. Int. Ed.* 2011, 50, 2120-2124] and M [Bielinski, E. A.; Lagaditis, P. O.; Zhang, Y. Y.; Mercado, B. Q.; Wurtele, C.; Bernskoetter, W. H.; Hazari, N.; Schneider, S. *J. Am. Chem. Soc.* 2014, 136, 10234-10237] of FIG. 14 have been reported to interconvert with cis dihydrides on a NMR timescale at room temperature. Exchange was not detected in NOESY spectra between 11a and 12b. However, it was observed that the dihydrides always maintained the same ratio of concentration, suggesting that they may interconvert on a slower timescale. Other non-rigid, six-coordinate iron dihydride complexes have also been known to undergo dynamic isomerization [Langer, R.; Iron, M. A.; Konstantinovski, L.; Diskin-Posner, Y.; Leitus, G.; Ben-David, Y.; Milstein, D. *Chem.—Eur. J.* 2012, 18, 7196-7209; Gerlach, D. H.; Peet, W. G.; Muetterties, E. L. *J. Am. Chem. Soc.* 1972, 94, 4545-4549; Meakin, P.; Muetterties, E. L.; Jesson, J. P. *J. Am. Chem. Soc.* 1973, 95, 75-88.].

Reaction of 7b with KOtBu in THF-d$_8$ under argon rapidly produced dicarbonyl complex 9 and other species (see FIG. 15). This contrasted with the reaction of bromohydrido complex K, or borohydrido complex L, which reacted with KOtBu under Ar to give amidohydrido complex N, shown in FIG. 14 [Bornschein, C.; Werkmeister, S.; Wendt, B.; Jiao, H.; Alberico, E.; Baumann, W.; Junge, H.; Junge, K.; Belier, M. *Nat. Commun.* 2014, 5, doi 10.1038/ncomms5111; Chakraborty, S.; Brennessel, W. W.; Jones, W. D. *J. Am. Chem. Soc.* 2014, 136, 8564-8567; Bielinski, E. A.; Lagaditis, P. O.; Zhang, Y. Y.; Mercado, B. Q.; Wurtele, C.; Bernskoetter, W. H.; Hazari, N.; Schneider, S. *J. Am. Chem. Soc.* 2014, 136, 10234-10237]. Structure of N was elucidated by single crystal X-ray diffraction [Chakraborty, S.; Brennessel, W. W.; Jones, W. D. *J. Am. Chem. Soc.* 2014, 136, 8564-8567]. The two PiPr$_2$ groups on the ligand in N appeared to be more effective at stabilizing an amido complex of this type, with respect to formation of iron(0) species, than the combination of PiPr$_2$ and PPh$_2$ on the unobserved amido species 13a (FIG. 16). It was considered that the smaller PPh$_2$ group may allow intermolecular carbonyl exchange to occur, ultimately leading to iron(0) dicarbonyl 9 and other species by a reductive elimination process, or direct reductive elimination of the hydrido and amido donors in 13a (discussed below).

Catalytic Testing

To determine whether dihydride complexes 11a/12a were the active species of the catalysis described herein, the complexes were tested with acetophenone to gauge conversion to 1-phenylethanol under H$_2$. Consequently, THF-d$_8$ solutions of the dihydrides 11a/12a were injected into a pressurized Parr reactor set at 50° C. and 5 bar H$_2$, along with 0.3 mL acetophenone (catalyst:substrate~1:500); complete conversion to 1-phenylethanol was observed in less than 15 minutes. The in situ-generated catalysts from 4b (described above) achieved complete conversion in 15 minutes as well. Without wishing to be bound by theory, it was considered that this suggested that dihydride species 11a/12a were the active catalyst, or an entry point into the catalytic cycle. Under the same conditions, the same conversion was observed for solutions of chiral dihydrides (S,S)-(S,S)-11b/12b with an e.e. of 83% (S)-1-phenylethanol, as was reported for the in situ-generated system. Thus, the dihydrides observed by NMR are the same in the enantioselective catalytic system. In other words, dihydrides (S,S)-11b/12b, observable by NMR, showed the same activity and selectivity as the in-situ system generated from (S,S)-4d, indicating that it was or directly lead into an active species in catalysis. It was observed that, if 0.05 mL of acetophenone was injected into a J-Young NMR tube containing dihydrides 11a/12a, and maintained a pressure of 1 atm H$_2$ at 30° C., the dihydride resonances disappeared and a low concentration of 1-phenyethanol was detected by GC. The catalyst system was active at 30° C., but pressures higher than 1 atm were required for catalyst turnover.

As described above, generation of the dihydride appeared to require base. To further test this, solutions containing the dihydride species 11a/12a were dried and any residue re-dissolved in benzene, and all excess base was filtered off; the dihydride solution was then directly injected into a reactor pressurized to 5 atm H$_2$. Minimal catalysis was observed, however, which suggested that base was required to generate the dihydride complexes, and for catalytic turnover. It was postulated that the observed requirement for base was a consequence of the alcohol being in excess during the catalysis, which may facilitate the iron complex being converted back to an alkoxide complex like 7b. Without wishing to be bound by theory, it was considered that the excess base was required to return the alkoxide complexes to the catalytic cycle, as discussed further below. This proposal was consistent with systems containing complexes 8 (R'''=tAmyl) generating more active catalyst systems than systems containing complexes 7 (R'''=Me), which form more stable alkoxides with less steric hindrance.

Without wishing to be bound by theory, another explanation was considered for the observed requirement for the presence of base during catalysis: that anionic amido species stabilized by potassium were involved in the catalytic cycle. The presence of such species have been proposed for Noyori ruthenium diamine catalyst systems during ketone hydrogenation [Hartmann, R.; Chen, P. *Angew. Chem. Int. Ed.* 2001, 40, 3581-3585; John, J. M.; Takebayashi, S.; Dabral, N.; Miskolzie, M.; Bergens, S. H. *J. Am. Chem. Soc.* 2013, 135, 8578-8584; Dub, P. A.; Henson, N. J.; Martin, R. L.; Gordon, J. C. *J. Am. Chem. Soc.* 2014, 136, 3505-3521]. It was found that addition of 1.1 equivalents per potassium ion of 2,2,2-cryptand to the activated catalyst mixture of 7b/KOtBu/acetophenone/H$_2$ (5 atm) had no effect on rate of catalysis. As formation of a stable [K(2,2,2-cryptand)]$^+$ complex should have prevented potassium from engaging in bonding with an amido ligand, alkoxide base or ketone substrate, this ruled out potassium-specific mechanisms as proposed for the Noyori system.

Postulated Mechanism for Ketone Hydrogenation

Observation of trans-dihydridoamine complexes 11a and (S,S)-11b in catalytically active solutions led to a proposed hydrogenation pathway [Alberico, E.; Sponholz, P.; Cordes, C.; Nielsen, M.; Drexler, H.-J.; Baumann, W.; Junge, H.; Beller, M. *Angew. Chem. Int. Ed.* 2013, 125, 14412-14416;

Chakraborty, S.; Dai, H.; Bhattacharya, P.; Fairweather, N. T.; Gibson, M. S.; Krause, J. A.; Guan, H. *J. Am. Chem. Soc.* 2014, 136, 7869-7872; Chakraborty, S.; Brennessel, W. W.; Jones, W. D. *J. Am. Chem. Soc.* 2014, 136, 8564-8567; Abdur-Rashid, K.; Clapham, S. E.; Hadzovic, A.; Harvey, J. N.; Lough, A. J.; Morris, R. H. *J. Am. Chem. Soc.* 2002, 124, 15104-15118; Abdur-Rashid, K.; Lough, A. J.; Morris, R. H. *Organometallics* 2000, 19, 2655-2657; Clapham, S. E.; Hadzovic, A.; Morris, R. H. *Coord. Chem. Rev.* 2004, 248, 2201-2237; Hadzovic, A.; Song, D.; MacLaughlin, C. M.; Morris, R. H. *Organometallics* 2007, 26, 5987-5999; e) Noyori, R. *Angew. Chem. Int. Ed.* 2002, 41, 2008-2022; Bertoli, M.; Choualeb, A.; Lough, A. J.; Moore, B.; Spasyuk, D.; Gusev, D. G. *Organometallics* 2011, 30, 3479-3482], as shown in FIG. 16. The mechanism was also supported by DFT calculations, discussed below.

Base was required to generate an intermediate that reacted with dihydrogen, thought to be hydrido amido complex 13a, analogous to structure N determined by DFT calculations, shown in FIG. 14. The structure of a similar complex, FeH(CO)(PiPr$_2$CH$_2$CH$_2$NCH$_2$CH$_2$PiPr$_2$), has recently been determined by single crystal X-ray diffraction [Chakraborty, S.; Brennessel, W. W.; Jones, W. D. *J. Am. Chem. Soc.* 2014, 136, 8564-8567]. It was proposed that base bound the alcohol that was released, forming a hydrogen-bonded alkoxide adduct of the form K[RO—HOR'] in a low dielectric constant solvent (THF). According to the DFT calculations, the starting alkoxide complex 7b was too stable without addition of base. Addition of dihydrogen trans to the hydride in complex 13a, in a similar fashion to 16-electron ruthenium hydrido amido complexes RuH(NH-L)(PR$_3$)$_2$ [Abdur-Rashid, K.; Lough, A. J.; Morris, R. H. *Organometallics* 2000, 19, 2655-2657; Clapham, S. E.; Hadzovic, A.; Morris, R. H. *Coord. Chem. Rev.* 2004, 248, 2201-2237; Hadzovic, A.; Song, D.; MacLaughlin, C. M.; Morris, R. H. *Organometallics* 2007, 26, 5987-5999], was found to lead to trans-dihydride complex 11a. Unlike with the ruthenium systems, it was found that dihydrogen can also add trans to the carbonyl in 13a to produce a cis dihydride 12a.

It was then proposed that the trans-dihydride complex transfers a proton from the ligand's nitrogen, and a hydride from the iron to a ketone's carbonyl group to give an alcohol product, thus regenerating the amido complex 13a. Trans-dihydrides on ruthenium [Abdur-Rashid, K.; Clapham, S. E.; Hadzovic, A.; Harvey, J. N.; Lough, A. J.; Morris, R. H. *J. Am. Chem. Soc.* 2002, 124, 15104-15118; Abdur-Rashid, K.; Lough, A. J.; Morris, R. H. *Organometallics* 2000, 19, 2655-2657; Clapham, S. E.; Hadzovic, A.; Morris, R. H. *Coord. Chem. Rev.* 2004, 248, 2201-2237; Hadzovic, A.; Song, D.; MacLaughlin, C. M.; Morris, R. H. *Organometallics* 2007, 26, 5987-5999; Abbel, R.; Abdur-Rashid, K.; Faatz, M.; Hadzovic, A.; Lough, A. J.; Morris, R. H. *J. Am. Chem. Soc.* 2005, 127, 1870-1882; Hamilton, R. J.; Bergens, S. H. *J. Am. Chem. Soc.* 2008, 130, 11979-11987; Takebayashi, S.; Bergens, S. H. *Organometallics* 2009, 28, 2349-2351; Takebayashi, S.; John, J. M.; Bergens, S. H. *J. Am. Chem. Soc.* 2010, 132, 12832-12834] and osmium [Bertoli, M.; Choualeb, A.; Lough, A. J.; Moore, B.; Spasyuk, D.; Gusev, D. G. *Organometallics* 2011, 30, 3479-3482] have been known to rapidly attack ketones, esters and imides in their outer coordination sphere; wherein the metal transferred a hydride to the carbonyl carbon, and the amine transferred a proton to the carbonyl oxygen in a metal-ligand bifunctional process, sometimes in a stepwise fashion [Noyori, R. *Angew. Chem. Int. Ed.* 2002, 41, 2008-2022; Bertoli, M.; Choualeb, A.; Lough, A. J.; Moore, B.; Spasyuk, D.; Gusev, D. G. *Organometallics* 2011, 30, 3479-3482].

Iron hydride complexes have been proposed to do the same bifunctional transfer [Morris, R. H. *Chem. Soc. Rev.* 2009, 38, 2282-2291; Sues, P. E.; Demmans, K. Z.; Morris, R. H. *Dalton Trans.* 2014, 43, 7650-7667; Sui-Seng, C.; Freutel, F.; Lough, A. J.; Morris, R. H. *Angew. Chem. Int. Ed.* 2008, 47, 940-943; Prokopchuk, D. E.; Morris, R. H. *Organometallics* 2012, 31, 7375-7385; Zuo, W.; Tauer, S.; Prokopchuk, D. E.; Morris, R. H. *Organometallics* 2014, doi: 10.1021/om500479q].

It was further postulated that the product alcohol might also react with the amido complex 13a, in a manner similar to the methanol, as shown in FIG. 16. It was considered that thus trapping the amido complex 13a by dihydrogen or alcohol may protect it from a reductive elimination pathway, or a bimolecular carbonyl exchange pathway that may lead to catalytic degradation into dicarbonyl 9 and other species.

DFT Studies

Structural optimization of each intermediate and transition state involved in the catalytic cycle using 7b was done using a functional M11-L with a 6-31++G(d,p) basis set with a THF solvation model. Important structures and transition states are shown in FIG. 17; a reaction coordinate diagram for the catalytic process is shown in FIG. 18. All energies were referenced to that of dihydride 11a. The dihydride had a distorted octahedral structure with Fe—H distances of 1.55 Å (H trans to H), longer than 1.54 (C trans to H) and 1.53 Å (N trans to H) bond lengths calculated for 12a due to higher trans influence of the hydride ligand compared to carbonyl and amine ligands, respectively [Abdur-Rashid, K.; Clapham, S. E.; Hadzovic, A.; Harvey, J. N.; Lough, A. J.; Morris, R. H. *J. Am. Chem. Soc.* 2002, 124, 15104-15118; Abbel, R.; Abdur-Rashid, K.; Faatz, M.; Hadzovic, A.; Lough, A. J.; Morris, R. H. *J. Am. Chem. Soc.* 2005, 127, 1870-1882; Bau, R.; Chiang, M. Y.; Ho, D. M.; Gibbins, S. G.; Emge, T. J.; Koetzle, T. F. *Inorg. Chem.* 1984, 23, 2823; Rybtchinski, B.; Ben-David, Y.; Milstein, D. *Organometallics* 1997, 16, 3786-3793; Lin, Z.; Hall, M. B. *Coord. Chem. Rev.* 1994, 135/136, 845-879]. These values were consistent with those determined in other iron hydride structures using single crystal neutron diffraction [Bau, R.; Chiang, M. Y.; Ho, D. M.; Gibbins, S. G.; Emge, T. J.; Koetzle, T. F. *Inorg. Chem.* 1984, 23, 2823; Ho, N. N.; Bau, R.; Mason, S. A. *J. Organomet. Chem.* 2003, 676, 85; Ricci, J. S.; Koetzle, T. F.; Bautista, M. T.; Hofstede, H.; Morris, R. H.; Sawyer, J. F. *J. Am. Chem. Soc.* 1989, 111, 8823; Sluys, L. S. V. D.; Eckert, J.; Eisenstein, O.; Hall, J. H.; Huffman, J. C.; Jackson, S. A.; Koetzle, T. F.; Kubas, G. J.; Vergamini, P. J.; Caulton, K. G. *J. Am. Chem. Soc.* 1990, 112, 4831]. Following the reaction as depicted in FIG. 18, the dihydride formed a weak adduct with acetophenone (17a) via an NH—O hydrogen bond with a modest increase in energy to G°=5.1 kcal/mol.

Transfer of the metal hydride to the ketone in transition state structure TS17a,18a (FIGS. 17 and 18, full structure calculation) had a free energy of activation of 20.9 kcal/mol, consistent with a process occurring in a temperature range of 25-50° C. It was considered that said energy barrier, due to sterics, was higher than 13.5 kcal/mol calculated for TS$_{P,Q}$ of a simplified system, wherein phenyl groups were replaced by hydrogens and isopropyl groups with methyls (see FIG. 19). The calculated 20.9 kcal/mol barrier was similar to that of the dihydrogen splitting step (TS21a,11a of FIG. 18), and was expected to be rate determining for bulkier ketone substrates. This transfer produced an alkoxide adduct (Q, FIG. 19 of the simplified system, not yet located for the full system), which received a proton from the NH group to produce the phenylethanol adduct 19a (see similar simplified structures Q and R in FIG. 20). A proton transfer transition state was located using a simplified ligand structure (FIG. 20), but not for the full structure. A slow hydride transfer to a ketone followed by a fast proton transfer step [Prokopchuk, D. E.; Morris, R. H. *Organometallics* 2012, 31, 7375-7385; Zweifel, T.; Naubron, J.-V.; Bittner, T.; Ott, T.; Grützmacher, H. *Angew. Chem. Int. Ed.* 2008, 47, 3245-3249; Zweifel, T.; Naubron, J.-V.; Gritzmacher, H. *Angew. Chem. Int. Ed.* 2009, 48, 559-563; Bertoli, M.; Choualeb, A.; Gusev, D. G.; Lough, A. J.; Major, Q.; Moore, B. *Dalton Trans.* 2011, 40, 8941-8949], or an asynchronous hydride-proton transfer [Guo, X.; Tang, Y.; Zhang, X.; Lei, M. *J. Phys. Chem. A.* 2011, 115, 12321-12330; b) Chen, Y.; Liu, S.; Lei, M. *J. Phys. Chem. C* 2008, 112, 13524-13527] has been considered common for similar metal-amido ketone hydrogenation catalysts (Fe, Ru or Os).

Liberation of alcohol product from 19a generated the diamagnetic iron hydridoamido complex 13a (G"=−0.3 kcal/mol with acetophenone and $H_2$). This amido complex was almost square pyramidal with a hydride in an apical position, and a planar amido nitrogen (FIG. 17) having a C—Fe—N angle of 168°, a C—Fe—H angle of 90° an N—Fe—H angle of 103°; the sum of the angles around nitrogen was 358°. By contrast, the crystal structure of hydridoamido complex N (FIG. 14) had a distortion towards trigonal bipyramidal with corresponding angles of 156°, 83° and 90° with a sum around N of 358°. Compared to a Fe—N(amine) distance of 2.08 Å for dihydride 11a, 13a had a much shorter Fe—N(amido) distance of 1.87 Å, which was comparable to the Fe—N(amido) bond of 1.86 Å in N. The structure of a distorted 13a (S=1) trigonal bipyramidal hydridoamido structure in a triplet state was also optimized, and found to be 20.6 kcal/mol higher in energy than diamagnetic 13a (FIG. 13). It was considered that a possible route to the dicarbonyl decomposition product 9 may have been via reductive elimination of 13a to an iron(0) monocarbonylamine complex Fe(CO)(P—NH—P') 16a. However this would have had to involve a spin state change, as the resulting iron(0) complex 16a was calculated to be more stable as a distorted tetrahedral S=1 structure by 8 kcal/mol, than a distorted square planar S=0 structure (FIG. 13).

Reaction of hydridoamido complex 13a with dihydrogen led to an end-on adduct of dihydrogen with amido complex 20a having an energy of G°=4.5 kcal/mol, and then a higher energy $\eta^2$-$H_2$ structure, 21a (G°=11.0 kcal/mol). Splitting of the coordinated hydrogen across the metal and amido nitrogen, TS21a, 11a (FIG. 17, 19, G°‡=20.3 kcal/mol) was calculated to be as energetically demanding as the hydride attack on the ketone; as such, it was considered that it could be rate-determining under certain conditions. It was also considered that this could explain an experimental finding that increased pressure increased rate of hydrogenation of certain substrates such as 2-acetylpyridine; however, the system was complicated by many equilibria such as with alcohol, to give inactive alkoxide complexes, and with enolizable ketones, to give inactive enolate complexes, which influenced the amount of active catalyst and therefore rate. Further, product phenylethanol and its role in shuttling a proton in the dihydrogen splitting step, from the dihydrogen to the amido nitrogen via the alcohol, was examined [Hadzovic, A.; Song, D.; MacLaughlin, C. M.; Morris, R. H. *Organometallics* 2007, 26, 5987-5999; Ito, M.; Hirakawa, M.; Murata, K.; Ikariya, T. *Organometallics* 2001, 20, 379-381; Hasanayn, F.; Morris, R. H. *Inorg. Chem.* 2012, 51, 10808-10818]; however, it was found that the transition state (TS22a,23a, 20.3 kcal/mol, FIG. 21) was similar in energy to the transition state (TS21a,11a, 20.3 kcal/mol, FIG. 18) of the dihydrogen splitting mechanism, without the alcohol serving as a proton shuttle from dihydrogen to the amido nitrogen.

Alkoxide complex 7b was calculated to be 9.6 kcal/mol lower in energy than hydridoamido complex 13a in THF, in the absence of base (FIG. 16). When KOtBu was added to 7b, the system was calculated to be 5.5 kcal/mol more stable than the hydridoamido complex 13a plus the strongly hydrogen-bonded salt K[tBuOH—OR'] in THF (FIG. 17). In view of the foregoing, it was postulated therefore that the presence of base destabilized the alkoxide by approximately 4 kcal/mol, as proposed above. It was considered that this observed effect may be greater due to KOtBu existing as aggregates in solvents of low dielectric constant, such as THF [Chisholm, M. H.; Drake, S. R.; Naiini, A. A.; Streib, W. E. *Polyhedron* 1991, 10, 337-345; Song, D.; Morris, R. H. *Organometallics* 2004, 23, 4406-4413; Evans, W. J.; Sollberger, M. S.; Ziller, J. W. *J. Am. Chem. Soc.* 1993, 115, 4120-4127], and that breaking up these aggregates by way of alcohol hydrogen-bonding to an alkoxide would be entropically favorable. Similarly, the 1-phenylethanol product of the catalytic reaction can form an alkoxide Fe(CO)(P—NH—P')(OCHMePh) (FIG. 16, 14a), which was calculated to have relative energies of −7.1 kcal/mol without base, and −2.5 kcal/mol with KOtBu. This suggested that, during the catalytic cycle, some active species may be reverted back to the alkoxide complex, while added potassium or sodium alkoxide may help to reverse this process.

Also investigated was formation of cis-dihydride intermediate 12a, which was observed in minor concentration during the above-described NMR studies. Dihydrogen species 15a, which led to 12a, as shown in FIG. 18, was calculated to be 3.5 kcal/mol higher in energy than 21a, the corresponding dihydrogen species that led to 11a (FIG. 18). Similarly, 15a led to a heterolytic hydrogen splitting transition state TS15a, 12a that had a similar energy to TS21a, 11a (G'''‡=20.3 kcal/mol) to produce 12a (G'''‡=3.7 kcal/mol), which had a higher energy than 11a. This was consistent with an experimental observation that the cis-dihydride compound 12a was in smaller quantity compared to the trans-dihydride compound 11a.

In addition to the theoretical catalytic mechanistic study described above, full structure DFT calculations were performed using a smaller basis set (6-31 G) on an enantiodetermining step (EDS) of complex (S,S)-11b, with acetophenone as test substrate. This approach has been used successfully in other DFT investigations of outer sphere ketone asymmetric hydrogenation [Dub, P. A.; Henson, N. J.; Martin, R. L.; Gordon, J. C. *J. Am. Chem. Soc.* 2014, 136, 3505-3521; Chen, H.-Y. T.; Di Tommaso, D.; Hogarth, G.; Catlow, C. R. A. *Dalton Trans.* 2012, 41, 1867-1877; Feng, R.; Xiao, A.; Zhang, X.; Tang, Y.; Lei, M. *Dalton Trans.* 2013, 42, 2130-2145]. The hydride transfer step from iron to the ketone carbonyl was identified as the EDS (FIG. 22), and activation barriers for the S- and R-isomer were calculated to be 19.7 kcal/mol, and 22.1 kcal/mol, respectively (FIG. 24). This 2.4 kcal/mol difference represents an enantiomeric excess of 97% in the S-isomer, as calculated using transition state theory, which was considered to be fairly consistent with the experimental evidence, 89% ee at 25° C. (see above), given that a crude basis set was used. A consistent bias toward S alcohol production was observed when other functionals were employed, although predicted ee values varied 93-99% (see Table 3). After the hydride transfer, proton transfer and alcohol liberation completed conversion of prochiral acetophenone into (S)-1-phenylethanol.

Three factors were identified that contributed to the catalyst's enantioselectivity. First was size difference between the larger cyclohexyl substituents and the smaller phenyl substituents on the phosphine ligands. As depicted in FIG. 22, the more energetically favoured EDSs had the substrate's smaller methyl group oriented over the bulkier cyclohexyl groups; the more energetically demanding $EDS_R$, had the ketone's phenyl group positioned there. Secondly, in both scenarios, the phenyl and cyclohexyl substituents from the phosphine were visibly compressed away from the ketone, with the degree of compression smaller for the methyl group on the ketone than the phenyl. The phenyl groups on the ligand appeared to be more compressible because they could stack against each other. Thirdly, hydrogen-bonding strength, which was considered to have also contributed to the overall energy gap between EDSs and $EDS_R$. Calculated O—H bond distance between the oxygen in the keto-substrate, and the proton in the ligand's NH moiety in EDSs was 1.86 Å, while in $EDS_R$, it was 2.12 Å; this signalled a stronger hydrogen bond in the former structure.

CONCLUSIONS

An effective synthesis templated by iron(II) to make unsymmetrical P—N—P' ligands by condensation of phosphine-amines with phosphine-aldehydes, generated from phosphonium dimers, has been developed. A mixture of trans- and cis-iron complexes, $Fe(CO)(Br)_2(P-CH=N-P')$, 2 and 3, were initially synthesized from a one-pot reaction with phosphonium dimers (1a-c), KOtBu, $FeBr_2$ and $PhP_2C_2H_4NH_2$ in THF under a CO(g) atmosphere. Upon addition of $AgBF_4$ to said complexes under a CO atmosphere, new complexes trans-$[Fe(CO)_2(Br)(P-CHNP')]$[BF4] (4a-d) were synthesized in high yield. Complexes 4a-d were reacted with $LiAlH_4$, followed by alcohol, to generate a mixture of iron hydride complexes with proposed mer-$Fe(H)(CO)(OR)(P-CH_2NH-P')$ structures, where R=Me or tAmyl. A mixture of monohydride iron pre-catalysts 7a, 7b or (S,S)-8d that had alkyl substituents on one of the phosphorus atoms of the P—$CH_2NH$—P' ligand were active for ketone hydrogenation and aldehydes under mild basic conditions (T=50° C., p($H_2$)=5 atm). Catalytic performance reached TOF up to 2000 $h^{-1}$, TON up to 2000 and enantioselectivities up to 85% (S). Consequently, it has been shown that a variety of such iron hydride compounds can be prepared in a few steps from aldehyde and amine building blocks on Fe(II).

Further, trans dihydrido iron complexes 11a and (S,S)-11b were identified by experiment, as well as their cis-dihydride isomers 12a and (S,S)-12b. Unlike the trans dihydride $FeH_2(CO)(PNP)$ of Milstein that did not contain an NH group, complexes 11a and (S,S)-11b had inequivalent hydrides, and reacted with acetophenone at 30° C. Therefore, it has been postulated that the NH group may be important in catalytic design for ketone hydrogenation. The presence of excess base was also considered to facilitate catalytic activity, although it was demonstrated that specific use of a potassium counter-cation was not critical, as potassium-2,2,2-cryptand worked as well. Consequently, it was proposed that base may be needed for formation of an undetected hydridoamido complex, 13a, in the presence of otherwise more stable alkoxide complexes. These experimental observations, supplemented with DFT calculations, were used to propose a catalytic cycle for ketone hydrogenation. The hydridoamido complex 13a reacts with dihydrogen to form a reactive trans-dihydride complex, which attacks a ketone in an outer coordination sphere, much like related ruthenium metal-ligand bifunctional systems. A hydride and then a proton are transferred stepwise to produce the product alcohol, and an hydridoamido intermediate 13a or (S,S)-13b. Relative energies of the (S,S)-11b system's pro-S and pro-R transition states were calculated using DFT, and were consistent with the observed enantioselectivity favouring the (S) alcohol. Calculations suggested that the energy barriers for hydride attack on the ketone, and dihydrogen splitting at the amido complex were similar, and that either step could be turn-over limiting depending on conditions. In the absence of dihydrogen, the hydridoamido intermediates (13a or (S,S)-13b) decomposed to iron(0) species.

TABLE 1

Hydrogenation of acetophenone catalyzed by achiral complexes 4a-b once activated by reaction with $LiAlH_4$ and then alcohol.[a]

| Entry | Pre-catalyst | Base[b] | Temperature (° C.) | Alcohol[a] | C/S ratio | Time (min, 99% conv) | TOF[c] ($h^{-1}$) |
|---|---|---|---|---|---|---|---|
| 1 | 4a | KOtBu | 50 | tAmylOH | 1/500 | 15 | 1980 |
| 2 | 4b | KOtBu | 50 | tAmylOH | 1/500 | 15 | 1980 |
| 3 | 4b | KOtBu | 25 | tAmylOH | 1/500 | 30 | 990 |
| 4 | 4b[d] | KOtBu | 50 | tAmylOH | 1/500 | 30 | 990 |
| 5 | 4b | KOtBu | 50 | MeOH | 1/500 | 55 | 550 |
| 6 | 4b | KOtBu | 50 | EtOH | 1/500 | 30 | 990 |
| 7 | 4b | None | 50 | tAmylOH | 1/500 | No conversion | — |
| 8 | 4a | KOtBu | 50 | tAmylOH | 1/2000 | 60 | 1980 |
| 9 | 4c | KOtBu | 50 | tAmylOH | 1/500 | No conversion | — |

[a]Pre-catalyst activated in situ: 5 mg (4a, b or c), 4 equiv $LiAlH_4$ (0.05 mL 1M in THF), followed by 0.5 mL alcohol; 6 mL THF.
[b]Base (C/B = 1/10) dissolved in 4 mL THF and added into reactor preloaded with THF solution with pre-catalyst and substrate to commence catalysis.
[c] Calculated at 99% conversion.
[d]$NaAlH_4$ used instead.

TABLE 2

Reactivity of various ketones in the asymmetric hydrogenation reaction using an in situ generated catalyst derived from (S,S)-4d.[a]

$$R'\text{-CO-}R'' \xrightarrow[\text{THF, 50° C.}]{\substack{0.1 \text{ mol \% (S,S)-4d,} \\ \text{LiAlH}_4, \text{tAmylOH} \\ 1 \text{ mol \% KOtBu} \\ 5 \text{ atm H}_2}} R'\text{-CH(OH)-}R''\text{*}$$

(S,S)-4d catalyst: [Fe complex with PCy$_2$, CO, Br, N, OC, PPh$_2$, Ph ligands][BF$_4$]

| Entry | Substrate | Time (h) | % conv.[b] | e.e.[b] (%) | TOF (h$^{-1}$) | TON |
|---|---|---|---|---|---|---|
| 1 | acetophenone | 0.5 | 99 | 80 (S) | 1980 | 990 |
| 2 | 2'-chloroacetophenone | 1.5 | 95 | 80 (S) | 630 | 950 |
| 3 | 3'-chloroacetophenone | 1.3 | 95 | 80 (S) | 730 | 950 |
| 4 | 4'-chloroacetophenone | 1 | 99 | 76 (S) | 990 | 990 |
| 5 | 4'-bromoacetophenone | 1.5 | 95 | 77 (S) | 630 | 950 |
| 6 | 4'-methoxyacetophenone | 0.8 | 96 | 82 (S) | 1200 | 960 |
| 7 | 4'-methylacetophenone | 0.6 | 96 | 79 (S) | 1600 | 960 |
| 8 | propiophenone | 0.8 | 90 | 83 (S) | 1500 | 900 |
| 9 | isobutyrophenone | 6 | 90 | 60 (S) | 150 | 900 |
| 10 | cyclohexyl phenyl ketone | 12 | 90 | 37 (S) | 65 | 800 |
| 11 | benzophenone | 2 | 95 | n/a | 500 | 950 |
| 12 | 1-indanone | 18 | 92 | 22 (S) | 50 | 920 |
| 13 | 2'-acetonaphthone | 0.5 | 99 | 80 (S) | 1980 | 990 |

TABLE 2-continued

Reactivity of various ketones in the asymmetric hydrogenation reaction using an in situ generated catalyst derived from (S,S)-4d.[a]

R'C(O)R'' + H₂ →(0.1 mol % (S,S)-4d, LiAlH₄, tAmylOH, 1 mol % KOtBu, 5 atm H₂, THF, 50° C.)→ R'*CH(OH)R''

(S,S)-4d catalyst: [N=CH-CH₂-PCy₂; Fe with CO, Br, OC, PPh₂, Ph ligand][BF₄]

| Entry | Substrate | Time (h) | % conv.[b] | e.e.[b] (%) | TOF (h⁻¹) | TON |
|---|---|---|---|---|---|---|
| 14 | 1-acetonaphthone | 0.8 | 99 | 85 (S) | 1230 | 990 |
| 15 | 4-phenyl-2-butanone | 1 | 97 | 5 (S) | 970 | 970 |
| 16 | 1-phenyl-2-butanone | 11 | 97 | 30 (S) | 90 | 970 |
| 17 | 3-methyl-2-butanone | 3 | 91 | 46 (S) | 300 | 910 |
| 18 | 2-acetylthiophene | 4 | 95 | 82 (S) | 240 | 950 |
| 19 | 2-acetylfuran | 5 | 90 | 85 (S) | 220 | 900 |
| 20 | 2-acetylpyridine | 1 | 20[c] | 74 (S)[d] | 200 | 200 |
| 21 | benzalacetone | 24 | 0 | n/a | 0 | 0 |
| 22 | 5-hexen-2-one | 4 | 95 | 0 | 240 | 950 |

[a]Catalyst prepared in situ: (S,S)-4d (5 mg, 0.007 mmol) mixed with 6 equiv LiAlH₄ (0.05 mL of 1M LiAlH₄ in THF) followed by 0.5 mL tAmylOH in 6 mL THF.
[b]Determined by GC.
[c]Determined by ¹H NMR spectroscopy.
[d]Determined by HPLC.

TABLE 2a

Asymmetric hydrogenation of acetophenone using an in situ generated chiral catalyst.[a]

PhC(O)Me + H₂ →(0.1 mol % "Fe", LiAlH₄, tAmylOH, 1 mol % KOtBu, 5 atm H₂, THF, 50° C.)→ Ph*CH(OH)Me "Fe" catalyst: [N=CH-CH(R¹)-CH(R²)-NH-... PCy₂, CO, Br, OC, PPh₂][BF₄]

(S,S)-4d: R¹ = Me, R² = Ph
(S)-4e: R¹ = iPr, R² = H
(S)-4f: R¹ = Ph, R² = H
(S)-4g: R¹ = CH₂Ph, R² = H

| Entry | "Fe" | Time (h) | % conv.[b] | e.e.[b] (%) | TOF (h⁻¹) | TON |
|---|---|---|---|---|---|---|
| 1 | (S,S)-4d | 0.5 | 99 | 80 (S) | 1980 | 990 |
| 2 | (S)-4e | 1 | 40 | 63 (S) | 400 | 400 |
| 3 | (S)-4f | 1 | 99 | 55 (S) | 990 | 990 |
| 4 | (S)-4g | 2 | 99 | 13 (S) | 495 | 990 |

[a]Catalyst prepared in situ: "Fe" (0.007 mmol) mixed with 6 equiv LiAlH₄ (0.05 mL of 1M LiAlH₄ in THF) followed by 0.5 mL tAmylOH in 6 mL THF.
[b]Determined by GC.

TABLE 3

Enantio-determining step (EDS) transition state energies calculated using different functionals[a]

| Functional | $\Delta G_S^{\neq}$ (kcal/mol) | $\Delta G_R^{\neq}$ (kcal/mol) | $\Delta G_{(R-S)}^{\neq}$ (kcal/mol) | ee % |
|---|---|---|---|---|
| M11-L | 19.65 | 22.14 | 2.49 | 97 |
| M06 | 15.18 | 17.17 | 1.99 | 93 |
| mPW1PW91 | 25.58 | 28.09 | 2.51 | 97 |
| PBE0 | 22.25 | 25.41 | 3.15 | 99 |
| ωB97X-D | 12.01 | 14.23 | 2.22 | 95 |

[a]All of the EDS transition states were calculated using the Berny algorithm method provided in Gaussian (opt = (CalcFC, ts)). Initial guess geometries were located by optimizing a restricted model where the iron-hydride and hydride-carbonyl carbon distances were fixed; these distances came from the corresponding transition state located with a simplified structure or from the EDS TS found using one of the other functionals.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A complex of formula (I)

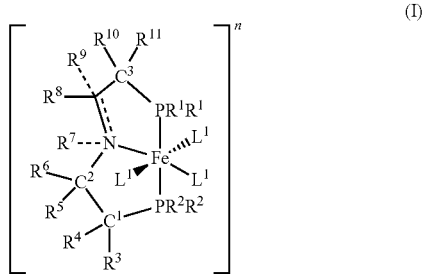

(I)

wherein:
a dashed line indicates that a bond may or may not be present;
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;
$R^7$ is absent, H, $AlH_3$, or $AlH_5$;
each $L^1$ is independently H, $BH_4$, $AlH_4$, a halide, CO, an N-heterocyclic carbene, $OR^{12}$, or $NCR^{13}$, wherein $R^{12}$ and $R^{13}$ are independently $C_1$-$C_{10}$ alkyl, $C_2$-$C_{10}$ alkenyl, aryl, heteroaryl, or $C_3$-$C_{10}$ cycloalkyl, each of which may be substituted; or, one of $L^1$ may be absent;
when $R^7$ is $AlH_3$ or $AlH_5$, at least one of the H may bridge with Fe to form a cycle together with the atoms to which they are attached;
n is 0, +1, or −1, wherein, when n is +1, the complex further comprises at least one non-coordinating anion, Y; and, when n is −1, the complex further comprises at least one non-coordinating cation, Z; such that the total charge of the complex is 0;
with the proviso that, when the nitrogen is singly bound to the carbon attached to $R^9$, each of $R^3$ to $R^{11}$ are H, one $L^1$ is CO, and the other two $L^1$,s are Br, or Br and H, or $BH_4$ and H, then the $R^1$ and $R^2$ substituents cannot all be isopropyl; and
with the proviso that, when the nitrogen is singly bound to the carbon attached to $R^9$, each of $R^3$ to $R^{11}$ are H, $R^7$ is absent, one $L^1$ is absent, one of $L^1$ is CO, and one of $L^1$ is H, then the $R^1$ and $R^2$ substituents cannot all be isopropyl.

2. The complex of claim 1, wherein the complex has the structure of one of the following formulae:
(i) the complex has the structure of formula (Ia)

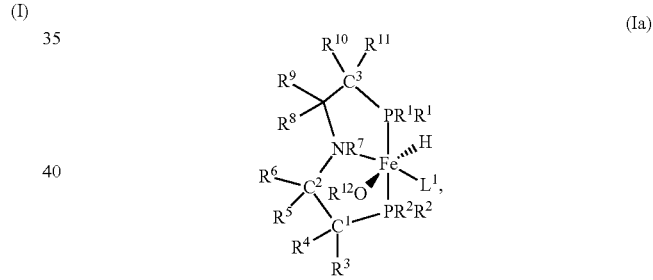

(Ia)

wherein:
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;
$R^7$ is H;
$R^{12}$ is independently $C_1$-$C_{10}$ alkyl, $C_2$-$C_{10}$ alkenyl, aryl, heteroaryl, or $C_3$-$C_{10}$ cycloalkyl, each of which may be substituted; and
$L^1$ is CO, N-heterocyclic carbene, or $NCR^{13}$, wherein $R^{13}$ is independently $C_1$-$C_{10}$ alkyl, $C_2$-$C_{10}$ alkenyl, aryl, heteroaryl, or $C_3$-$C_{10}$ cycloalkyl, each of which may be substituted;

(ii) the complex has the structure of formula (Ib) or (Ic)

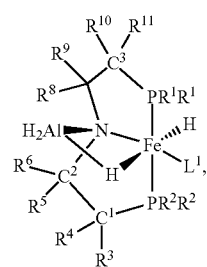

(Ib)

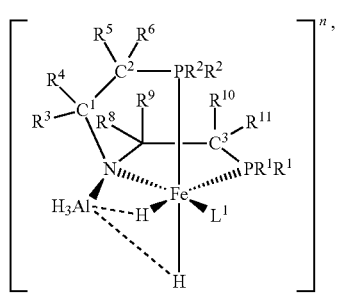

(Ic)

wherein
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ $R^{11}$, together with the carbon atoms to which they are attached, form a substituted $C_5$-$C_{10}$ cycloalkyl ring;
$L^1$ is CO, N-heterocyclic carbene, or $NCR^{13}$, wherein $R^{13}$ is independently $C_1$-$C_{10}$ alkyl, $C_2$-$C_{10}$ alkenyl, aryl, heteroaryl, or $C_3$-$C_{10}$ cycloalkyl, each of which may be substituted; and
n is −1, wherein the complex further comprises at least one non-coordinating cation Z, and the total charge of the complex is 0;

(iii) the complex has the structure of formula (Id)

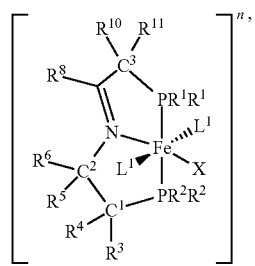

(Id)

wherein:
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;
X is a halide;
$L^1$ is CO; and
n is +1, wherein the complex further comprises a non-coordinating anion Y, and the total charge of the complex is 0;

(iv) the complex has the structure of formula (Ie) or (If)

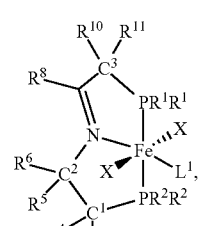

(Ie)

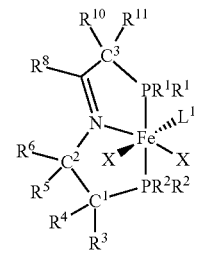

(If)

wherein:
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;
X is a halide; and
$L^1$ is CO, N-heterocyclic carbene, or $NCR^{13}$, wherein $R^{13}$ is independently $C_1$-$C_{10}$ alkyl, $C_2$-$C_{10}$ alkenyl, aryl, heteroaryl, or $C_3$-$C_{10}$ cycloalkyl, each of which may be substituted;
(v) the complex has the structure of formula (Ig) or (Ih)

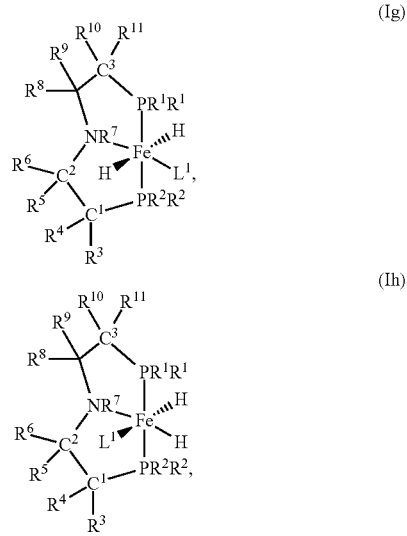

wherein:
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;
$R^7$ is H; and
$L^1$ is CO, N-heterocyclic carbene, or $NCR^{13}$, wherein $R^{13}$ is independently $C_1$-$C_{10}$ alkyl, $C_2$-$C_{10}$ alkenyl, aryl, heteroaryl, or $C_3$-$C_{10}$ cycloalkyl, each of which may be substituted; or
(vi) the complex has the structure of formula (Ii)

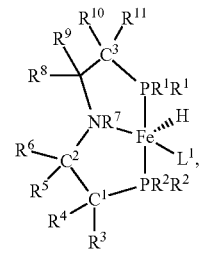

wherein:
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;
each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;
$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;
$R^7$ is H or absent; and
$L^1$ is CO, N-heterocyclic carbene, or $NCR^{13}$, wherein $R^{13}$ is independently $C_1$-$C_{10}$ alkyl, $C_2$-$C_{10}$ alkenyl, aryl, heteroaryl, or $C_3$-$C_{10}$ cycloalkyl, each of which may be substituted.

3. The complex of claim 1, wherein:
(i) each $R^1$ is independently $C_1$-$C_8$ alkyl or $C_3$-$C_8$ cycloalkyl; or, alternatively $C_1$-$C_4$ alkyl or $C_3$-$C_6$ cycloalkyl; and, each $R^2$ is independently aryl, or heteroaryl;

(ii) $R^3$ and $R^6$ are each independently H, $C_1$-$C_8$ alkyl, aryl, or heteroaryl; or, alternatively H, $C_1$-$C_4$ alkyl, aryl, or heteroaryl; and, each $R^4$, $R^5$, $R^8$, $R^{10}$ and $R^{11}$ is H; and/or (iii) $R^{12}$ is $C_1$-$C_8$ alkyl, $C_2$-$C_8$ alkenyl, $C_3$-$C_{10}$ cycloalkyl, aryl, or heteroaryl; or, alternatively, $R^{12}$ is $C_1$-$C_4$ alkyl, $C_2$-$C_4$ alkenyl, $C_3$-$C_6$ cycloalkyl, aryl, or heteroaryl.

4. The complex of claim 3, wherein:
(i) each $R^1$ is independently isopropyl or cyclohexyl; and, each $R^2$ is phenyl;
(ii) $R^3$ and $R^6$ are each independently H, methyl, isopropyl, phenyl, or benzyl; and/or
(iii) $R^{12}$ is methyl, ethyl, t-butyl, or t-amyl.

5. The complex of claim 1, wherein Z is an alkali metal cation.

6. The complex of claim 1, wherein Y is a conjugate base of a strong acid.

7. The complex of claim 6, wherein Y is a halide, $BF_4^-$, $PF_6^-$, $SbF_6^-$, $NO_3^-$, $ClO_4^-$, $CF_3COO^-$, $R^{14}SO_3^-$, $CF_3SO_3^-$, $C_6H_5SO_3^-$, p-$CH_3C_6H_4SO_3^-$, phosphates, TRISPHAT(Δ- or Λ-$P(OC_6Cl_4O)_3^-$), carboranes, $B(R^{14})_4^-$ or $Al(R^{14})_4^-$, each of which may be substituted, wherein each $R^{14}$ is independently an optionally substituted $C_1$-$C_6$ alkyl, aryl, heteroaryl, $C_6H_3(CF_3)_2$ and $C_6F_5$, halogen, pseudohalogen, $C_1$-$C_8$ alkoxide, or aryloxide.

8. The complex of claim 1, wherein carbon $C^1$, $C^2$ or $C^3$, or any combination thereof, is chiral, and the complex is enantiomerically enriched, or a racemate.

9. The complex of claim 8, wherein the complex has the structure of formula:

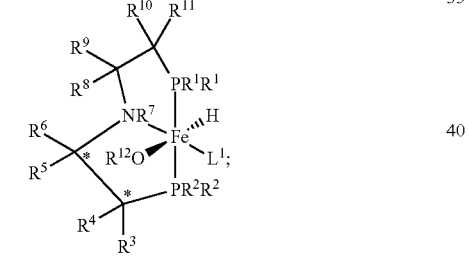
(Ia')

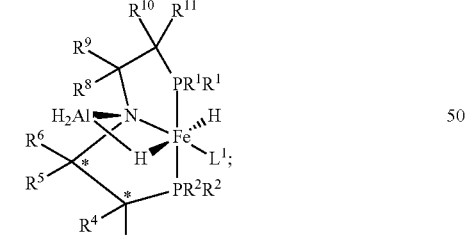
(Ib')

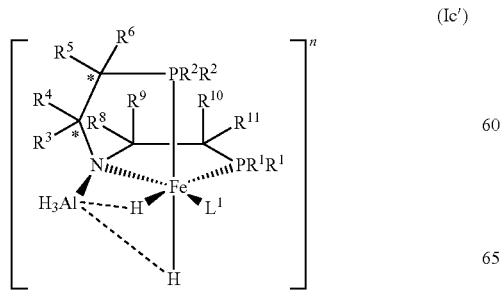
(Ic')

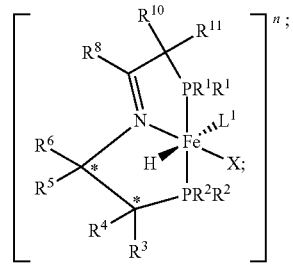
(Id')

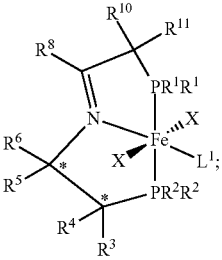
(Ie')

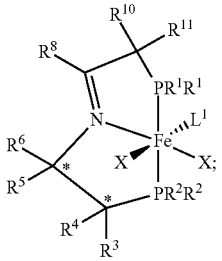
(If')

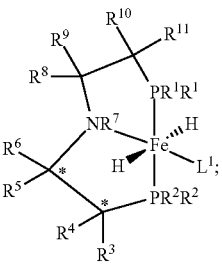
(Ig')

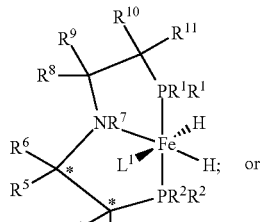
(Ih')

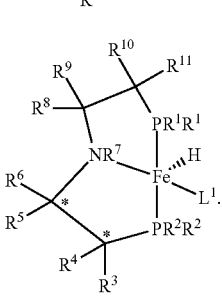
(Ii')

10. A process for the preparation of a complex of claim 1, the process comprising:

(i) reacting a phosphine-aldehyde precursor of formula (II)

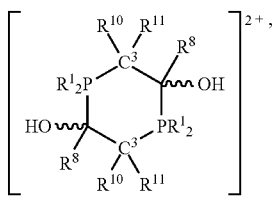
(II)

wherein $R^1$, $R^8$, $R^{10}$, and $R^{11}$ are as defined in claim 1, with a phosphine-amine of formula (III)

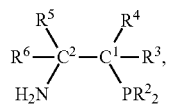
(III)

wherein $R^2$, $R^3$, $R^4$, $R^5$, and $R^6$ are as defined in claim 1, in the presence of
an iron(II) compound,
a CO atmosphere, and
a strong base,
to form a complex of formula (Ie), or to form a mixture of complexes of formula (Ie) and formula (If),

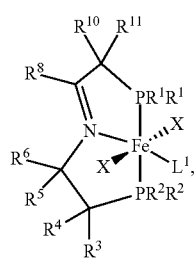
(Ie)

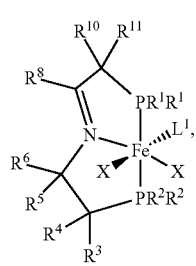
(If)

wherein X is a halide, and
$L^1$ is CO;

the complex of formula (Ie), or the mixture of complexes of formula (Ie) and formula (If), is further reacted in the presence of
a silver salt, and
a CO atmosphere, to form a complex of formula (Id)

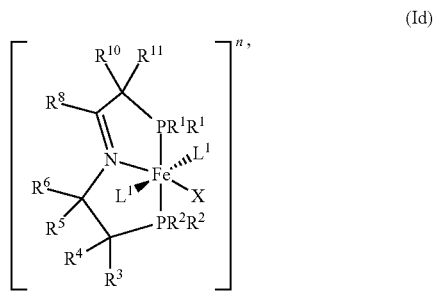
(Id)

wherein n is +1,
which is further reacted in the presence of a reducing agent to form the complex of formula (Ib) and/or (Ic)

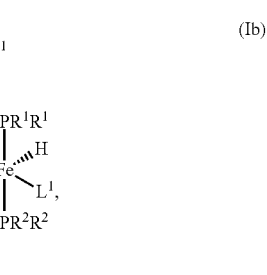
(Ib)

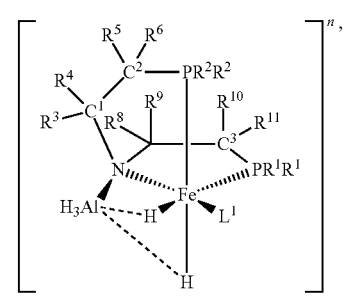
(Ic)

wherein $R^9$ is H, and n is −1,
which are further reacted with an excess of a primary, secondary, or tertiary alcohol, to form the complex of formula (Ia)

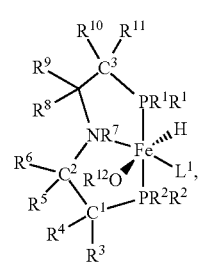
(Ia)

wherein $R^7$ is H and $R^{12}$ is selected from $C_1$-$C_{10}$ alkyl, $C_2$-$C_{10}$ alkenyl, aryl, heteroaryl, or $C_3$-$C_{10}$ cycloalkyl, each of which may be substituted; and/or (ii) reacting a complex of formula (Ia)

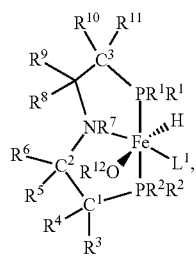
(Ia)

wherein $R^1$, $R^2$, $R^3$, $R^4$, $R^5$, $R^6$, $R^7$, $R^8$, $R^9$, $R_{10}$, $R^{11}$, $R^{12}$ and $L^1$ are as defined in (i) above,
in the presence of
a base, and
a $H_2$ atmosphere
to form a complex of formula (Ig) and/or a complex of formula (Ih),

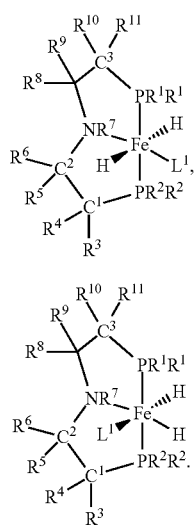
(Ig)

(Ih)

11. The process of claim 10, wherein carbon $C^1$ and/or $C^2$ of the phosphine-amine of formula (III) is chiral; and/or carbon $C^3$ of the phosphine-aldehyde precursor of formula (II) is chiral; and, the compound of which they are a part is enantiomerically enriched, or a racemate.

12. The process of claim 10, wherein the iron(II) compound is an iron(II) salt; or, an iron(II) complex.

13. The process of claim 12, wherein:
(i) the iron(II) salt is $FeBr_2$ or $FeCl_2$;
(ii) the iron(II) complex is $Fe(CO)_4Br_2$; or
(iii) the iron(II) complex is $Fe(CO)_4Br_2$, and $Fe(CO)_4Br_2$ is additionally reacted in the presence of UV radiation to aid in formation of the complex of formula (Ie); or, to form a mixture of complexes of formula (Ie) and formula (If).

14. The process of claim 10, wherein:
(i) the strong base is $KO^tBu$;
(ii) the silver salt is $AgBF_4$, and the $BF_4^-$ anion acts as a non-coordinating counter-ion for the complex of formula (Id);
(iii) the reducing agent is $LiAlH_4$ or $NaAlH_4$; and/or
(iv) the alcohol is MeOH, EtOH, $^tBuOH$ or $^tAmylOH$.

15. The process of claim 10, wherein carbon $C^1$, $C^2$ or $C^3$, or any combination thereof, of complexes of formula (Ia), (1g), or (1h) is chiral, and the complex is enantiomerically enriched, or a racemate.

16. The process of claim 10, wherein the base referenced in (ii) is KOtBu, NaOtBu, Ph-CH(OK)CH$_3$, or NaOMe.

17. A method for hydrogenation of a substrate comprising contacting the substrate with a hydrogen source in the presence of a complex of claim 1, under conditions suitable for hydrogenation.

18. The method of claim 17, wherein the substrate is a ketone, aldehyde, or imine.

19. The method of claim 17, wherein the hydrogen source is hydrogen gas at a pressure >0 atm and <70 atm.

20. The complex of claim 1, wherein the complex has the structure of one of the following formulae:
(i) the complex has the structure of formula (Ig) or (Ih)

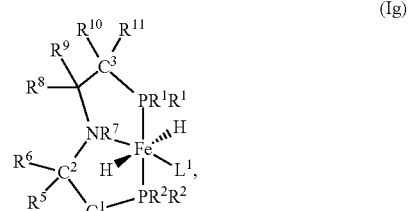
(Ig)

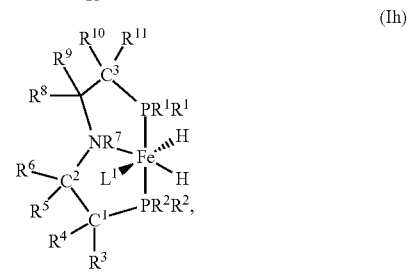
(Ih)

wherein:
each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;

each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;

$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;

$R^7$ is H; and $L^1$ is CO, N-heterocyclic carbene, or $NCR^{13}$, wherein $R^{13}$ is independently $C_1$-$C_{10}$ alkyl, $C_2$-$C_{10}$ alkenyl, aryl, heteroaryl, or $C_3$-$C_{10}$ cycloalkyl, each of which may be substituted;

(ii) the complex has the structure of formula (Ii)

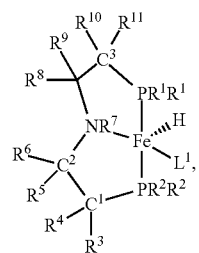

(Ii)

wherein:

each $R^1$ is independently $C_1$-$C_{10}$ alkyl, $C_2$-$C_{10}$ alkenyl, $C_1$-$C_8$ alkoxy, $C_3$-$C_{10}$ cycloalkyl, aryl, or heteroaryl, each of which may be optionally substituted; or the two geminal $R^1$ substituents combine to form a $C_2$-$C_4$ linear alkyl diradical or $C_3$-$C_{10}$ branched alkyl diradical, each of which may be optionally substituted, such that the two $R^1$ substituents, together with the phosphorus atom to which they are attached, form a ring;

each $R^2$ is independently aryl, heteroaryl, $C_1$-$C_{10}$ alkyl, $C_2$-$C_{10}$ alkenyl, $C_1$-$C_{10}$ alkoxy, aryloxy, or $C_3$-$C_{10}$ cycloalkyl, each of which may be optionally substituted; or the two geminal $R^2$ groups combine to form a $C_2$-$C_4$ linear alkyl diradical or $C_3$-$C_{10}$ branched alkyl diradical, each of which may be optionally substituted, such that the two $R^2$ substituents, together with the phosphorus atom to which they are attached, form a ring;

$R^3$, $R^4$, $R^5$, $R^6$, $R^8$, $R^9$, $R^{10}$ and $R^{11}$ are each independently H, or $C_1$-$C_{10}$ alkyl, $C_2$-$C_{10}$ alkenyl, aryl, heteroaryl, or $C_3$-$C_{10}$ cycloalkyl, each of which may be optionally substituted; or, $R^3$ and $R^4$, $R^5$ and $R^6$, and/or $R^{10}$ and $R^{11}$, together with the carbon atoms to which they are attached, form a substituted $C_5$-$C_{10}$ cycloalkyl ring;

$R^7$ is absent; and $L^1$ is CO, N-heterocyclic carbene, or $NCR^{13}$, wherein $R^{13}$ is independently $C_1$-$C_{10}$ alkyl, $C_2$-$C_{10}$ alkenyl, aryl, heteroaryl, or $C_3$-$C_{10}$ cycloalkyl, each of which may be substituted; or (iii)

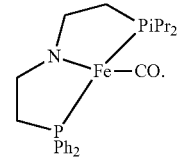

* * * * *